US012778477B2

(12) United States Patent
Zhu et al.

(10) Patent No.: US 12,778,477 B2
(45) Date of Patent: Nov. 3, 2026

(54) CARDIAC INFORMATION DYNAMIC DISPLAY SYSTEM AND METHOD

(71) Applicant: ENCHANNEL MEDICAL, LTD., Irvine, CA (US)

(72) Inventors: Min Zhu, San Marcos, CA (US); Derrick R. Chou, San Diego, CA (US); Graydon E. Beatty, Carlsbad, CA (US); Xinwei Shi, San Diego, CA (US); Ahmad Falahatpisheh, San Marcos, CA (US)

(73) Assignee: ENCHANNEL MEDICAL, LTD., Irvine, CA (US)

(*) Notice: Subject to any disclaimer, the term of this patent is extended or adjusted under 35 U.S.C. 154(b) by 0 days.

(21) Appl. No.: 16/097,955

(22) PCT Filed: May 3, 2017

(86) PCT No.: PCT/US2017/030915
§ 371 (c)(1),
(2) Date: Oct. 31, 2018

(87) PCT Pub. No.: WO2017/192769
PCT Pub. Date: Nov. 9, 2017

(65) Prior Publication Data

US 2019/0246930 A1 Aug. 15, 2019

Related U.S. Application Data

(60) Provisional application No. 62/331,351, filed on May 3, 2016.

(51) Int. Cl.

*A61B 5/287* (2021.01)
*A61B 5/00* (2006.01)
(Continued)

(52) U.S. Cl.
CPC .............. *A61B 5/287* (2021.01); *A61B 5/343* (2021.01); *A61B 5/6853* (2013.01);
(Continued)

(58) Field of Classification Search
CPC ..... A61B 5/0422; A61B 5/044; A61B 5/6853; A61B 5/6858; A61B 5/6859; A61B 5/743;
(Continued)

(56) References Cited

U.S. PATENT DOCUMENTS

| | | | |
|---|---|---|---|
| 4,173,228 | A | 11/1979 | Van Steenwyk et al. |
| 4,841,977 | A | 6/1989 | Griffith et al. |

(Continued)

FOREIGN PATENT DOCUMENTS

| | | |
|---|---|---|
| CA | 2825736 | 5/2008 |
| CA | 2829626 | 9/2012 |

(Continued)

OTHER PUBLICATIONS

Extended European Search Report dated Oct. 23, 2019 issued in corresponding European Application No. 17793291.0.

(Continued)

*Primary Examiner* — Rex R Holmes
(74) *Attorney, Agent, or Firm* — Onello & Mello P.C.

(57) ABSTRACT

Provided are a localization system and method useful in the acquisition and analysis of cardiac information. The localization system and method can be used with systems that perform cardiac mapping, diagnosis and treatment of cardiac abnormalities, as examples, and in the retrieval, processing, and interpretation of such types of information. The localization system and method use high impedance inputs, improved isolation, and relatively high drive currents for
(Continued)

pairs of electrodes used to establish a multi-axis coordinate system. The axes can be rotated and scaled to improve localization.

29 Claims, 22 Drawing Sheets

(51) Int. Cl.

| | |
|---|---|
| ***A61B 5/343*** | (2021.01) |
| *A61B 5/06* | (2006.01) |
| *A61B 8/12* | (2006.01) |
| *A61B 18/00* | (2006.01) |
| *A61B 18/14* | (2006.01) |

(52) U.S. Cl.

CPC .......... *A61B 5/6858* (2013.01); *A61B 5/6859* (2013.01); *A61B 5/743* (2013.01); *A61B 5/061* (2013.01); *A61B 5/7214* (2013.01); *A61B 8/12* (2013.01); *A61B 2018/00267* (2013.01); *A61B 2018/00357* (2013.01); *A61B 2018/00577* (2013.01); *A61B 2018/00839* (2013.01); *A61B 2018/00875* (2013.01); *A61B 18/1492* (2013.01)

(58) Field of Classification Search

CPC . A61B 2018/00839; A61B 8/12; A61B 5/061; A61B 5/7214; A61B 2018/00267; A61B 18/1492; A61B 2018/00357; A61B 2018/00577; A61B 2018/00875

See application file for complete search history.

(56) References Cited

U.S. PATENT DOCUMENTS 5,020,540 A 6/1991 Chamoun
5,041,973 A 8/1991 Lebron et al.
5,156,151 A 10/1992 Imran
5,293,868 A 3/1994 Nardella
5,482,472 A 1/1996 Garoni et al.
5,499,981 A 3/1996 Kordis
5,555,883 A 9/1996 Avitall
5,595,183 A 1/1997 Swanson et al.
5,601,084 A 2/1997 Sheehan et al.
5,622,174 A 4/1997 Yamazaki
5,647,367 A 7/1997 Lum et al.
5,662,108 A 9/1997 Budd et al.
5,687,737 A 11/1997 Branham et al.
5,722,402 A 3/1998 Swanson et al.
5,722,416 A 3/1998 Swanson et al.
5,740,808 A 4/1998 Panescu et al.
5,749,833 A 5/1998 Hakki et al.
5,759,158 A 6/1998 Swanson
5,782,239 A 7/1998 Webster, Jr.
5,795,298 A 8/1998 Vesley et al.
5,795,299 A 8/1998 Eaton et al.
5,820,568 A 10/1998 Willis
5,830,144 A 11/1998 Vesely
5,846,198 A 12/1998 Killmann
5,876,336 A 3/1999 Swanson et al.
5,928,228 A 7/1999 Kordis et al.
5,944,022 A 8/1999 Nardella et al.
5,968,040 A 10/1999 Swanson et al.
6,014,590 A 1/2000 Whayne et al.
6,024,703 A 2/2000 Zanelli et al.
6,066,096 A 5/2000 Smith et al.
6,086,532 A 7/2000 Panescu et al.
6,107,699 A 8/2000 Swanson
6,115,626 A 9/2000 Whayne et al.
6,187,032 B1 2/2001 Ohyu et al.
6,188,928 B1 2/2001 Noren et al.
6,216,027 B1 4/2001 Willis et al.
6,216,043 B1 4/2001 Swanson et al.
6,223,072 B1 4/2001 Mika et al.
6,240,307 B1 5/2001 Beatty et al.
6,277,077 B1 8/2001 Brisken et al.
6,301,496 B1 10/2001 Reisfeld
6,396,198 B1 5/2002 Okimura et al.
6,400,981 B1 6/2002 Govari
6,490,474 B1 12/2002 Willis et al.
6,514,249 B1 2/2003 Maguire et al.
6,556,695 B1 4/2003 Packer et al.
6,574,492 B1 6/2003 Ben-Haim et al.
6,640,119 B1 10/2003 Budd et al.
6,695,785 B2 2/2004 Brisken et al.
6,716,166 B2 4/2004 Govari
6,728,562 B1 4/2004 Budd et al.
6,772,004 B2 8/2004 Rudy
6,773,402 B2 8/2004 Govari et al.
6,824,515 B2 11/2004 Suorsa et al.
6,826,420 B1 11/2004 Beatty et al.
6,826,421 B1 11/2004 Beatty et al.
6,839,588 B1 1/2005 Rudy
6,869,403 B2 3/2005 Narimatsu et al.
6,895,267 B2 5/2005 Panescu et al.
6,939,309 B1 9/2005 Beatty et al.
6,950,689 B1 9/2005 Willis et al.
6,957,101 B2 10/2005 Porath et al.
6,970,733 B2 11/2005 Willis et al.
6,978,168 B2 12/2005 Beatty et al.
6,990,370 B1 1/2006 Beatty et al.
6,993,388 B2 1/2006 Bullinga
7,187,964 B2 3/2007 Khoury
7,187,973 B2 3/2007 Hauck
7,258,674 B2 8/2007 Hillstead et al.
7,263,397 B2 8/2007 Hauck et al.
7,263,399 B2 8/2007 Carlson
7,285,094 B2 10/2007 Nohara et al.
7,285,119 B2 10/2007 Stewart et al.
7,289,841 B2 10/2007 Johnson et al.
7,289,843 B2 10/2007 Beatty et al.
7,291,146 B2 11/2007 Steinke et al.
7,351,914 B2 4/2008 Kaneto et al.
7,433,730 B1 10/2008 Berrier
7,479,141 B2 1/2009 Kleen et al.
7,505,810 B2 3/2009 Harlev et al.
7,515,954 B2 4/2009 Harlev et al.
7,536,218 B2 5/2009 Govari et al.
7,573,182 B2 8/2009 Savage
7,689,261 B2 3/2010 Mohr et al.
7,715,907 B2 5/2010 Koertge et al.
7,729,752 B2 6/2010 Harlev et al.
7,766,838 B2 8/2010 Yagi et al.
7,806,825 B2 10/2010 Heim
7,841,986 B2 * 11/2010 He ........................ A61B 6/503
600/508
7,848,789 B2 12/2010 Govari et al.
7,905,838 B2 3/2011 Hirota
7,918,793 B2 4/2011 Altmann et al.
7,930,018 B2 4/2011 Harlev et al.
7,953,475 B2 5/2011 Harlev et al.
7,957,791 B2 6/2011 Harlev et al.
8,038,625 B2 10/2011 Afonso et al.
8,086,303 B2 12/2011 Zhang et al.
8,103,327 B2 1/2012 Harlev et al.
8,103,338 B2 1/2012 Harlev et al.
8,147,486 B2 4/2012 Honour et al.
8,150,499 B2 4/2012 Gelbart et al.
8,155,756 B2 4/2012 Yang et al.
8,175,680 B2 5/2012 Panescu
8,200,314 B2 6/2012 Bladen et al.
8,208,998 B2 6/2012 Beatty et al.
8,221,411 B2 7/2012 Francischelli et al.
8,233,972 B2 7/2012 Zhang
8,290,575 B2 10/2012 Tarassenko et al.
8,311,613 B2 11/2012 Danehorn
8,320,711 B2 11/2012 Altmann et al.
8,326,419 B2 12/2012 Rosenberg et al.
8,346,339 B2 1/2013 Kordis et al.
8,360,786 B2 1/2013 Duryea
8,364,234 B2 1/2013 Kordis et al.
8,380,294 B2 2/2013 Messier et al.

(56) References Cited

U.S. PATENT DOCUMENTS 8,388,547 B2 3/2013 Revishvili et al.
8,400,164 B2 3/2013 Osadchy et al.
8,401,625 B2 3/2013 Harlev et al.
8,412,307 B2 4/2013 Willis et al.
8,417,313 B2 4/2013 Scharf et al.
8,428,690 B2 4/2013 Li et al.
8,447,377 B2 5/2013 Harlev et al.
8,449,535 B2 5/2013 Deno et al.
8,454,596 B2 6/2013 Ma et al.
8,463,368 B2 6/2013 Harlev et al.
8,465,433 B2 6/2013 Zwirn
8,467,853 B2 6/2013 Hunter et al.
8,478,388 B2 7/2013 Nguyen et al.
8,512,255 B2 8/2013 Scharf et al.
8,532,753 B2 9/2013 Makdissi
8,565,851 B2 10/2013 Lau et al.
8,571,647 B2 10/2013 Harlev et al.
8,583,228 B2 11/2013 Li et al.
8,597,193 B2 12/2013 Grunwald et al.
8,641,705 B2 2/2014 Leo et al.
8,700,119 B2 4/2014 Scharf et al.
8,712,507 B2 4/2014 Cazares et al.
8,740,840 B2 6/2014 Foley et al.
8,755,861 B2 6/2014 Harlev et al.
8,825,130 B2 9/2014 Just et al.
8,825,134 B2 9/2014 Danehorn
8,852,103 B2 10/2014 Rothberg et al.
8,903,488 B2 12/2014 Callas et al.
8,903,510 B2 12/2014 Rosenberg et al.
8,918,158 B2 12/2014 Scharf et al.
8,923,956 B2 12/2014 Clark et al.
8,929,975 B2 1/2015 Zhang et al.
8,934,988 B2 1/2015 Persson et al.
8,948,837 B2 2/2015 Harlev et al.
8,968,299 B2 3/2015 Kauphusman et al.
8,972,228 B2 3/2015 Ghosh et al.
8,979,839 B2 3/2015 De La Rama et al.
8,986,207 B2 3/2015 Li et al.
8,989,842 B2 3/2015 Li et al.
9,002,442 B2 4/2015 Harley et al.
9,005,198 B2 4/2015 Long et al.
9,011,423 B2 4/2015 Brewster et al.
9,023,027 B2 5/2015 Bar-Tal et al.
9,026,196 B2 5/2015 Curran et al.
9,031,642 B2 5/2015 Ghosh
9,037,259 B2 5/2015 Mathur
9,044,245 B2 6/2015 Condie et al.
9,060,756 B2 6/2015 Bencini et al.
9,113,807 B2 8/2015 Koyrakh et al.
9,113,910 B2 8/2015 Pachon Mateos et al.
9,155,590 B2 10/2015 Mathur
9,167,982 B2 10/2015 Scharf et al.
9,173,638 B2 11/2015 Govari et al.
9,186,081 B2 11/2015 Afonso et al.
9,186,212 B2 11/2015 Nabutovsky et al.
9,192,318 B2 11/2015 Scharf et al.
9,220,425 B2 12/2015 Shachar et al.
9,220,432 B2 12/2015 Bukhman
9,241,687 B2 1/2016 Mcgee
9,259,165 B2 2/2016 Rubinstein et al.
9,259,166 B2 2/2016 Rudy et al.
9,271,680 B2 3/2016 Dubois et al.
9,314,620 B2 4/2016 Long et al.
9,339,207 B2 5/2016 Grunwald et al.
9,351,789 B2 5/2016 Novichenok et al.
D758,596 S 6/2016 Perryman et al.
9,358,398 B2 6/2016 Moffitt et al.
9,380,953 B2 7/2016 Houben et al.
9,414,880 B2 8/2016 Monson et al.
9,456,759 B2 10/2016 Lian et al.
9,474,486 B2 10/2016 Eliason et al.
9,474,491 B2 10/2016 Li et al.
9,480,525 B2 11/2016 Lopes et al.
9,486,282 B2 11/2016 Solis
9,486,355 B2 11/2016 Gustus et al.
9,492,227 B2 11/2016 Lopes et al.
9,492,228 B2 11/2016 Lopes et al.
9,498,192 B2 11/2016 Hashimshony et al.
9,504,395 B2 11/2016 Scharf et al.
9,510,763 B2 12/2016 Ghosh et al.
9,510,901 B2 12/2016 Steinke et al.
9,526,573 B2 12/2016 Lopes et al.
9,549,708 B2 1/2017 Mercanzini et al.
9,560,982 B2 2/2017 Kordis et al.
9,579,149 B2 2/2017 Kelly et al.
D782,626 S 3/2017 Werneth et al.
D782,686 S 3/2017 Werneth et al.
9,585,588 B2 3/2017 Marecki et al.
9,591,990 B2 3/2017 Chen et al.
9,597,148 B2 3/2017 Olson
9,603,651 B2 3/2017 Ghosh
9,610,024 B2 4/2017 Scharf et al.
9,662,033 B2 5/2017 Severino
9,687,167 B2 6/2017 Laughner et al.
9,689,759 B2 6/2017 Fandrey et al.
9,693,699 B2 7/2017 Spector et al.
9,713,730 B2 7/2017 Mathur et al.
9,717,555 B2 8/2017 Chan et al.
9,717,559 B2 8/2017 Ditter et al.
9,730,602 B2 8/2017 Harlev et al.
9,757,044 B2 9/2017 Scharf et al.
9,775,578 B2 10/2017 Katz
9,801,681 B2 10/2017 Laske et al.
9,808,171 B2 11/2017 Balachandran et al.
9,827,039 B2 11/2017 Dandler et al.
9,833,161 B2 12/2017 Govari
9,848,795 B2 12/2017 Marecki et al.
9,872,653 B2 1/2018 Li et al.
9,888,862 B2 2/2018 Harlev et al.
9,901,303 B2 2/2018 Olson
9,913,589 B2 3/2018 Scharf et al.
9,918,652 B2 3/2018 Zeng et al.
9,955,917 B2 5/2018 Bitzer
9,962,097 B2 5/2018 Ghosh et al.
9,968,268 B2 5/2018 Scharf et al.
9,974,457 B2 5/2018 Ghosh et al.
9,986,950 B2 6/2018 Eliason et al.
10,004,459 B2 6/2018 Werneth et al.
10,010,368 B2 7/2018 Laske et al.
10,028,706 B2 7/2018 Brockway et al.
10,039,464 B2 8/2018 Dubois et al.
10,045,706 B2 8/2018 Geistert et al.
10,045,707 B2 8/2018 Govari
10,049,771 B2 8/2018 Voth et al.
10,052,153 B2 8/2018 Olson
10,080,602 B2 9/2018 Wittkampf
10,082,395 B2 9/2018 Koyrakh et al.
10,135,815 B2 11/2018 Lecun et al.
10,137,297 B2 11/2018 Gunderson
10,163,252 B2 12/2018 Harlev et al.
10,201,288 B2 2/2019 Harlev et al.
10,201,311 B2 2/2019 Chou et al.
10,258,249 B2 4/2019 Talkachova et al.
10,296,707 B2 5/2019 Passerini et al.
10,299,692 B2 5/2019 Kalinin et al.
D851,774 S 6/2019 Werneth et al.
10,314,497 B2 6/2019 Scharf et al.
10,314,649 B2 6/2019 Bakos et al.
10,335,051 B2 7/2019 Harlev et al.
10,362,955 B2 7/2019 Arunachalam et al.
10,398,337 B2 9/2019 Zigelman et al.
10,405,766 B2 9/2019 Stewart et al.
10,405,828 B2 9/2019 Deladi et al.
10,413,206 B2 9/2019 Scharf et al.
10,424,045 B2 9/2019 Park et al.
10,441,187 B2 10/2019 Afonso et al.
10,441,188 B2 10/2019 Katz et al.
10,456,056 B2 10/2019 Govari et al.
10,463,267 B2 11/2019 Scharf et al.
10,467,801 B2 11/2019 Harlev et al.
10,470,743 B2 11/2019 Grunwald et al.
10,499,826 B2 12/2019 Balachandran et al.
10,506,948 B2 12/2019 Wodlinger et al.
10,512,435 B2 12/2019 Li et al.

(56) References Cited

U.S. PATENT DOCUMENTS

| | | | |
|---|---|---|---|
| 10,517,670 | B2 | 12/2019 | Bar-Tal et al. |
| 10,593,234 | B2 | 3/2020 | Zhu et al. |
| 10,617,317 | B2 | 4/2020 | Cohen et al. |
| 10,621,790 | B2 | 4/2020 | Perlman et al. |
| 10,631,913 | B2 | 4/2020 | Hull et al. |
| 10,639,106 | B1 | 5/2020 | Sheiner et al. |
| 10,653,318 | B2 | 5/2020 | Welsh et al. |
| 10,667,753 | B2 | 6/2020 | Werneth et al. |
| 10,687,765 | B1 | 6/2020 | Benaroya et al. |
| 10,728,242 | B2 | 7/2020 | Lecun et al. |
| 10,736,693 | B2 | 8/2020 | Lepak et al. |
| 10,796,801 | B2 | 10/2020 | Silverman |
| 10,842,561 | B2 | 11/2020 | Viswanathan et al. |
| 10,856,827 | B2 | 12/2020 | Katz |
| 10,874,320 | B2 | 12/2020 | Klebanov et al. |
| 10,888,236 | B2 | 1/2021 | Ruppersberg |
| 10,888,379 | B2 | 1/2021 | Pappone et al. |
| 10,932,723 | B2 | 3/2021 | Eliason et al. |
| 10,945,633 | B2 | 3/2021 | Chen et al. |
| 11,000,206 | B2 | 5/2021 | Govari et al. |
| 11,006,853 | B2 | 5/2021 | Ludwin et al. |
| 11,013,444 | B2 | 5/2021 | Scharf et al. |
| 11,033,329 | B2 | 6/2021 | Stewart et al. |
| 11,064,930 | B2 | 7/2021 | Zigelman et al. |
| 11,096,617 | B2 | 8/2021 | Han et al. |
| 11,096,741 | B2 | 8/2021 | Govari et al. |
| 11,134,975 | B2 | 10/2021 | Nicolaescu et al. |
| 11,141,216 | B2 | 10/2021 | Onik et al. |
| 11,147,617 | B1 | 10/2021 | Koblish |
| 11,179,112 | B2 | 11/2021 | Li et al. |
| 11,179,199 | B2 | 11/2021 | Everling |
| 11,278,209 | B2 | 3/2022 | Scharf et al. |
| 11,291,398 | B2 | 4/2022 | Deno et al. |
| D954,970 | S | 6/2022 | Werneth et al. |
| 11,357,437 | B2 | 6/2022 | Katz et al. |
| 11,399,759 | B2 | 8/2022 | Welsh et al. |
| 11,564,607 | B2 | 1/2023 | Berenfeld et al. |
| 11,622,713 | B2 | 4/2023 | Ben-Haim et al. |
| 11,664,125 | B2 | 5/2023 | Tuysuzoglu et al. |
| 11,701,021 | B2 | 7/2023 | Schmidt et al. |
| 11,839,481 | B2 | 12/2023 | Severino |
| 11,931,157 | B2 | 3/2024 | Scharf et al. |
| 11,998,357 | B2 | 6/2024 | Diep et al. |
| 12,048,479 | B2 | 7/2024 | Govari et al. |
| 12,048,546 | B2 | 7/2024 | Nguyen et al. |
| 12,059,535 | B2 | 8/2024 | Osadchy et al. |
| 12,070,264 | B2 | 8/2024 | Buchnik et al. |
| 12,082,881 | B2 | 9/2024 | Cohen et al. |
| 12,082,936 | B2 | 9/2024 | Olson |
| 12,133,984 | B2 | 11/2024 | Ghosh et al. |
| 12,144,636 | B2 | 11/2024 | Ziv-Ari et al. |
| 12,167,917 | B2 | 12/2024 | Relan et al. |
| 12,249,040 | B2 | 3/2025 | Harlev et al. |
| 12,324,619 | B2 | 6/2025 | Cohen et al. |
| 12,357,364 | B2 | 7/2025 | Sliwa et al. |
| 12,383,328 | B2 | 8/2025 | Howard et al. |
| 12,426,799 | B2 | 9/2025 | Papini |
| 12,446,955 | B2 | 10/2025 | Howard et al. |
| 12,507,937 | B2 | 12/2025 | Deno et al. |
| 2001/0007070 | A1 | 7/2001 | Stewart et al. |
| 2002/0026118 | A1 | 2/2002 | Govari |
| 2002/0045810 | A1 | 4/2002 | Ben-Haim |
| 2002/0128565 | A1 | 9/2002 | Rudy |
| 2002/0165441 | A1 | 11/2002 | Coleman et al. |
| 2003/0036696 | A1 | 2/2003 | Willis et al. |
| 2003/0065271 | A1 | 4/2003 | Khoury |
| 2003/0078494 | A1 | 4/2003 | Panescu et al. |
| 2003/0153907 | A1 | 8/2003 | Suorsa et al. |
| 2003/0158477 | A1 | 8/2003 | Panescu |
| 2003/0176799 | A1 | 9/2003 | Beatty et al. |
| 2003/0231789 | A1 | 12/2003 | Willis et al. |
| 2003/0236465 | A1 | 12/2003 | Narimatsu et al. |
| 2003/0236466 | A1 | 12/2003 | Tarjan et al. |
| 2004/0039293 | A1 | 2/2004 | Porath et al. |
| 2004/0039312 | A1 | 2/2004 | Hillstead et al. |
| 2004/0082846 | A1 | 4/2004 | Johnson et al. |
| 2004/0082870 | A1 | 4/2004 | Rudy et al. |
| 2004/0082948 | A1 | 4/2004 | Stewart et al. |
| 2004/0113498 | A1 | 6/2004 | Kroenke |
| 2004/0122317 | A1 | 6/2004 | Heim |
| 2004/0254437 | A1 | 12/2004 | Hauck et al. |
| 2005/0059880 | A1 | 3/2005 | Mathias et al. |
| 2005/0096647 | A1 | 5/2005 | Steinke et al. |
| 2005/0101874 | A1 | 5/2005 | Beatty et al. |
| 2005/0113665 | A1 | 5/2005 | Mohr et al. |
| 2005/0148836 | A1 | 7/2005 | Kleen et al. |
| 2005/0203375 | A1 | 9/2005 | Willis et al. |
| 2005/0267453 | A1 | 12/2005 | Wong et al. |
| 2006/0052716 | A1 | 3/2006 | Beatty et al. |
| 2006/0058663 | A1 | 3/2006 | Willis et al. |
| 2006/0058676 | A1 | 3/2006 | Yagi et al. |
| 2006/0058692 | A1 | 3/2006 | Beatty et al. |
| 2006/0058693 | A1 | 3/2006 | Beatty et al. |
| 2006/0084884 | A1 | 4/2006 | Beatty et al. |
| 2006/0084970 | A1 | 4/2006 | Beatty et al. |
| 2006/0084971 | A1 | 4/2006 | Beatty et al. |
| 2006/0084972 | A1 | 4/2006 | Beatty et al. |
| 2006/0116576 | A1 | 6/2006 | Mcgee et al. |
| 2006/0184163 | A1 | 8/2006 | Breen |
| 2007/0049817 | A1 | 3/2007 | Preiss et al. |
| 2007/0053482 | A1* | 3/2007 | Kohler ...................... G06T 7/20 378/8 |
| 2007/0055150 | A1 | 3/2007 | Donaldson et al. |
| 2007/0055167 | A1 | 3/2007 | Bullinga |
| 2007/0060832 | A1 | 3/2007 | Levin |
| 2007/0083194 | A1 | 4/2007 | Kunis et al. |
| 2007/0106146 | A1 | 5/2007 | Altmann et al. |
| 2007/0177770 | A1 | 8/2007 | Derchak et al. |
| 2007/0219551 | A1 | 9/2007 | Honour |
| 2007/0232949 | A1 | 10/2007 | Saksena |
| 2007/0244479 | A1 | 10/2007 | Beatty et al. |
| 2007/0270703 | A1 | 11/2007 | He et al. |
| 2007/0299351 | A1 | 12/2007 | Harlev et al. |
| 2007/0299352 | A1 | 12/2007 | Harlev et al. |
| 2007/0299353 | A1 | 12/2007 | Harlev et al. |
| 2008/0009758 | A1 | 1/2008 | Voth |
| 2008/0033312 | A1 | 2/2008 | Nakai et al. |
| 2008/0146937 | A1 | 6/2008 | Lee et al. |
| 2008/0287777 | A1 | 11/2008 | Li et al. |
| 2009/0005675 | A1 | 1/2009 | Grunwald et al. |
| 2009/0024086 | A1 | 1/2009 | Zhang et al. |
| 2009/0076483 | A1 | 3/2009 | Danehorn |
| 2009/0082691 | A1 | 3/2009 | Denison et al. |
| 2009/0131930 | A1 | 5/2009 | Gelbart et al. |
| 2009/0143651 | A1 | 6/2009 | Kallback et al. |
| 2009/0171274 | A1 | 7/2009 | Harlev et al. |
| 2009/0264781 | A1 | 10/2009 | Scharf |
| 2010/0067753 | A1 | 3/2010 | Visser |
| 2010/0076426 | A1 | 3/2010 | de la Rama et al. |
| 2010/0094279 | A1 | 4/2010 | Kauphusman et al. |
| 2010/0168578 | A1 | 7/2010 | Garson, Jr. et al. |
| 2010/0191131 | A1 | 7/2010 | Revishvili et al. |
| 2010/0198041 | A1 | 8/2010 | Christian et al. |
| 2010/0249623 | A1 | 9/2010 | Makdissi |
| 2010/0256627 | A1 | 10/2010 | Ma et al. |
| 2010/0286550 | A1 | 11/2010 | Harlev et al. |
| 2010/0298690 | A1 | 11/2010 | Scharf |
| 2011/0045130 | A1 | 2/2011 | Edens et al. |
| 2011/0077526 | A1 | 3/2011 | Zwirn |
| 2011/0082378 | A1 | 4/2011 | Messier et al. |
| 2011/0118726 | A1 | 5/2011 | De La Rama et al. |
| 2011/0125172 | A1 | 5/2011 | Gelbart et al. |
| 2011/0144510 | A1 | 6/2011 | Ryu et al. |
| 2011/0172658 | A1 | 7/2011 | Gelbart et al. |
| 2011/0190649 | A1 | 8/2011 | Rudy et al. |
| 2011/0213231 | A1 | 9/2011 | Hall et al. |
| 2011/0224540 | A1 | 9/2011 | Hauck et al. |
| 2011/0230775 | A1 | 9/2011 | Barley et al. |
| 2011/0245702 | A1 | 10/2011 | Clark et al. |
| 2011/0270237 | A1 | 11/2011 | Werneth et al. |
| 2011/0275949 | A1 | 11/2011 | Harlev et al. |
| 2012/0004540 | A1 | 1/2012 | Liu et al. |
| 2012/0078077 | A1 | 3/2012 | Harlev et al. |
| 2012/0082969 | A1 | 4/2012 | Schwartz et al. |

(56) References Cited

U.S. PATENT DOCUMENTS

2012/0136231 A1 5/2012 Markel
2012/0143298 A1 6/2012 Just et al.
2012/0165667 A1 6/2012 Altmann et al.
2012/0172859 A1 7/2012 Condie et al.
2012/0184863 A1 7/2012 Harlev et al.
2012/0197117 A1 8/2012 Picot et al.
2012/0197141 A1 8/2012 Vanney et al.
2012/0271138 A1 10/2012 Kordis et al.
2012/0271139 A1 10/2012 Kordis et al.
2012/0277567 A1 11/2012 Harlev et al.
2012/0277574 A1 11/2012 Panescu
2012/0283587 A1 11/2012 Ghosh et al.
2012/0284003 A1 11/2012 Ghosh et al.
2012/0310064 A1 12/2012 Mcgee
2013/0006238 A1 1/2013 Ditter et al.
2013/0066316 A1 3/2013 Steinke et al.
2013/0085361 A1 4/2013 Mercanzini et al.
2013/0096432 A1 4/2013 Hauck
2013/0116561 A1 5/2013 Rothberg et al.
2013/0158537 A1 6/2013 Deladi et al.
2013/0165916 A1 6/2013 Mathur
2013/0172715 A1 7/2013 Just et al.
2013/0190587 A1 7/2013 Lopes et al.
2013/0197614 A1 8/2013 Gustus et al.
2013/0204311 A1 8/2013 Kunis
2013/0225983 A1 8/2013 Willis et al.
2013/0226017 A1 8/2013 Scharf et al.
2013/0241929 A1 9/2013 Massarwa et al.
2013/0245621 A1 9/2013 Persson et al.
2013/0253298 A1 9/2013 Harlev et al.
2013/0267853 A1 10/2013 Dausch et al.
2013/0274582 A1* 10/2013 Afonso ................ A61B 5/6852 600/374
2013/0282084 A1 10/2013 Mathur et al.
2013/0289417 A1 10/2013 Grunwald et al.
2013/0304062 A1 11/2013 Chan et al.
2013/0304065 A1 11/2013 Lopes et al.
2013/0310827 A1 11/2013 Brewster et al.
2013/0330701 A1 12/2013 Rubinstein et al.
2014/0024910 A1 1/2014 Scharf et al.
2014/0068740 A1 3/2014 LeCun et al.
2014/0121470 A1* 5/2014 Scharf .................. A61B 5/0036 600/301
2014/0148677 A1 5/2014 Liempde et al.
2014/0180051 A1 6/2014 Thakur et al.
2014/0180150 A1 6/2014 Scharf et al.
2014/0200489 A1 7/2014 Behar et al.
2014/0200822 A1 7/2014 Dubois et al.
2014/0235988 A1 8/2014 Ghosh
2014/0257069 A1 9/2014 Eliason et al.
2014/0275921 A1 9/2014 Harlev et al.
2014/0276733 A1 9/2014 VanScoy et al.
2014/0276746 A1 9/2014 Nabutovsky et al.
2014/0276789 A1 9/2014 Dandler et al.
2014/0278129 A1 9/2014 Voth et al.
2014/0350400 A1 11/2014 Hill
2014/0358143 A1 12/2014 Novichenok et al.
2015/0011886 A1 1/2015 Radulescu et al.
2015/0038862 A1 2/2015 Gijsbers et al.
2015/0057522 A1 2/2015 Nguyen
2015/0164357 A1 6/2015 Zeng et al.
2015/0196219 A1 7/2015 Scharf et al.
2015/0208938 A1 7/2015 Houben et al.
2015/0216434 A1 8/2015 Ghosh et al.
2015/0216438 A1* 8/2015 Bokan .................. A61B 5/0452 600/515
2015/0223757 A1 8/2015 Werneth et al.
2015/0223863 A1 8/2015 Ghosh
2015/0257732 A1 9/2015 Ryan
2015/0257825 A1 9/2015 Kelly et al.
2015/0342491 A1 12/2015 Marecki et al.
2015/0351652 A1 12/2015 Marecki et al.
2015/0351701 A1 12/2015 Moxon et al.
2015/0366508 A1 12/2015 Chou et al.
2015/0374252 A1 12/2015 de la Rama et al.
2016/0007869 A1 1/2016 Scharf et al.
2016/0038051 A1 2/2016 Scharf et al.
2016/0051321 A1 2/2016 Salahieh et al.
2016/0100770 A1 4/2016 Afonso et al.
2016/0128771 A1 5/2016 Ditter et al.
2016/0128772 A1 5/2016 Reinders et al.
2016/0166310 A1 6/2016 Stewart et al.
2016/0192902 A1 7/2016 Werneth et al.
2016/0228019 A1 8/2016 Grunwald et al.
2016/0270709 A1 9/2016 Maccabee et al.
2016/0317093 A1 11/2016 Berenfeld et al.
2017/0035486 A1 2/2017 Lopes et al.
2017/0049347 A1 2/2017 Ghosh et al.
2017/0100049 A1 4/2017 Scharf et al.
2017/0128119 A1 5/2017 Lambert et al.
2017/0202469 A1 7/2017 Scharf et al.
2017/0202521 A1 7/2017 Urman et al.
2017/0258347 A1 9/2017 Scharf et al.
2017/0274204 A1 9/2017 Gunderson
2017/0311833 A1 11/2017 Afonso et al.
2017/0319180 A1 11/2017 Henneken et al.
2017/0319279 A1 11/2017 Fish et al.
2017/0360319 A1* 12/2017 Hagfors ................. A61B 5/743
2017/0367580 A1 12/2017 DiMaio et al.
2018/0055374 A1 3/2018 Scharf et al.
2018/0085160 A1 3/2018 Viswanathan et al.
2018/0146948 A1 5/2018 Chou et al.
2018/0242871 A1 8/2018 Ghosh et al.
2019/0021673 A1 1/2019 Werneth et al.
2019/0046113 A1 2/2019 Nikolic
2019/0053728 A1 2/2019 Yang et al.
2019/0159729 A1 5/2019 Chou et al.
2019/0200886 A1 7/2019 Welsh et al.
2019/0246930 A1 8/2019 Zhu et al.
2019/0313910 A1 10/2019 Vignon et al.
2019/0314083 A1 10/2019 Herrera et al.
2019/0350477 A1 11/2019 Han et al.
2019/0350489 A1 11/2019 Ludwin et al.
2020/0000355 A1 1/2020 Khair
2020/0015876 A1 1/2020 Chou et al.
2020/0022649 A1 1/2020 Rodriguez
2020/0077981 A1 3/2020 Grunwald et al.
2020/0138317 A1 5/2020 Scharf et al.
2020/0138525 A1 5/2020 Hill et al.
2020/0352439 A1 11/2020 Welsh et al.
2021/0000423 A1 1/2021 Werneth et al.
2021/0068694 A1 3/2021 Chou et al.
2021/0085386 A1 3/2021 Rao et al.
2021/0153843 A1 5/2021 Werneth et al.
2021/0161472 A1 6/2021 Eliason et al.
2021/0169394 A1 6/2021 Chou et al.
2021/0290960 A1 9/2021 Ghosh et al.
2022/0054192 A1 2/2022 Beeckler et al.
2022/0095980 A1 3/2022 Scharf et al.
2022/0202338 A1 6/2022 Zhu et al.
2022/0226046 A1 7/2022 Mariappan et al.
2022/0226637 A1 7/2022 Nanthakumar
2022/0401146 A1 12/2022 Asconeguy et al.
2023/0000361 A1 1/2023 Scharf et al.
2023/0048656 A1 2/2023 Chou et al.
2023/0218231 A1 7/2023 Chou et al.
2024/0050009 A1 2/2024 Welsh et al.
2024/0115314 A1 4/2024 Falahatpisheh et al.
2024/0156504 A1 5/2024 Chou et al.
2024/0206797 A1 6/2024 Chou et al.
2025/0010080 A1 1/2025 Ghosh et al.
2025/0017508 A1 1/2025 Scharf et al.
2025/0143781 A1 5/2025 Falahatpisheh et al.
2025/0160646 A1 5/2025 Welsh et al.
2025/0160657 A1 5/2025 Scharf et al.
2025/0281233 A1 9/2025 Chou et al.
2025/0302357 A1 10/2025 Scharf et al.
2025/0318784 A1 10/2025 Eliason et al.
2025/0325224 A1 10/2025 Werneth et al.
2026/0007325 A1 1/2026 Papini
2026/0053570 A1 2/2026 Mariappan et al.
2026/0096779 A1 4/2026 Werneth et al.

(56) References Cited

U.S. PATENT DOCUMENTS

| | | | |
|---|---|---|---|
| 2026/0144474 | A1 | 5/2026 | Chou et al. |
| 2026/0182894 | A1 | 7/2026 | Scharf et al. |

FOREIGN PATENT DOCUMENTS

| | | | |
|---|---|---|---|
| CN | 1856213 | | 11/2006 |
| CN | 1981710 | | 6/2007 |
| CN | 101048100 | | 10/2007 |
| CN | 201033076 | | 3/2008 |
| CN | 101254096 | | 9/2008 |
| CN | 201223445 | | 4/2009 |
| CN | 201275144 | | 7/2009 |
| CN | 100589775 | | 2/2010 |
| CN | 101657153 | | 2/2010 |
| CN | 1903122 | B | 4/2010 |
| CN | 101854853 | | 10/2010 |
| CN | 101912265 | | 12/2010 |
| CN | 101243975 | B | 1/2011 |
| CN | 102481108 | | 5/2012 |
| CN | 102770085 | | 11/2012 |
| CN | 103354730 | | 10/2013 |
| CN | 103561642 | | 2/2014 |
| CN | 101836862 | | 3/2014 |
| CN | 103687533 | | 3/2014 |
| CN | 103829941 | | 6/2014 |
| CN | 104462650 | | 3/2015 |
| CN | 104812297 | | 7/2015 |
| CN | 105025783 | | 11/2015 |
| CN | 105307565 | | 2/2016 |
| CN | 105358070 | | 2/2016 |
| CN | 104582614 | | 2/2018 |
| CN | 105073051 | | 4/2018 |
| CN | 111870341 | | 11/2020 |
| CN | 106963367 | | 9/2021 |
| CN | 216908099 | | 7/2022 |
| CN | 216933442 | | 7/2022 |
| CN | 217938884 | | 12/2022 |
| CN | 218106029 | | 12/2022 |
| CN | 111163685 | | 1/2023 |
| CN | 219022870 | | 5/2023 |
| CN | 108498090 | | 1/2024 |
| CN | 110507408 | | 7/2024 |
| CN | 114423481 | | 10/2024 |
| CN | 222091806 | | 12/2024 |
| CN | 222192326 | | 12/2024 |
| CN | 115426941 | | 8/2025 |
| CN | 223183547 | | 8/2025 |
| CN | 224166393 | | 4/2026 |
| EP | 1125549 | | 8/2001 |
| EP | 1166714 | | 1/2002 |
| EP | 1415608 | | 10/2004 |
| EP | 1760661 | | 3/2007 |
| EP | 1779787 | | 5/2007 |
| EP | 1852824 | | 11/2007 |
| EP | 2051625 | | 4/2009 |
| EP | 1743575 | | 1/2010 |
| EP | 2252203 | | 11/2010 |
| EP | 2491883 | | 8/2012 |
| EP | 2683293 | | 1/2014 |
| EP | 2711676 | | 3/2014 |
| EP | 2818104 | | 12/2014 |
| EP | 2848191 | | 3/2015 |
| EP | 2954867 | | 12/2015 |
| EP | 2953550 | | 8/2016 |
| EP | 3060150 | | 12/2017 |
| EP | 2884931 | | 1/2018 |
| EP | 1906821 | | 1/2020 |
| EP | 2912997 | | 5/2020 |
| EP | 3452992 | | 6/2021 |
| EP | 3551056 | | 6/2022 |
| EP | 3571989 | | 7/2022 |
| EP | 3923796 | | 12/2022 |
| EP | 3649931 | | 8/2023 |
| EP | 3831324 | | 8/2023 |
| EP | 3973906 | | 8/2023 |
| EP | 3838151 | | 2/2024 |
| EP | 3395277 | | 3/2024 |
| EP | 4014870 | | 7/2024 |
| EP | 4140428 | | 7/2024 |
| EP | 3808273 | | 8/2024 |
| EP | 3669772 | | 10/2024 |
| EP | 4186454 | | 11/2024 |
| EP | 4193947 | | 11/2024 |
| EP | 3933852 | | 3/2025 |
| EP | 3939529 | | 3/2025 |
| EP | 4093274 | | 7/2025 |
| EP | 3834730 | | 12/2025 |
| EP | 4389033 | | 12/2025 |
| EP | 4076240 | | 4/2026 |
| JP | 08501477 | | 2/1996 |
| JP | 08504333 | | 5/1996 |
| JP | 08164140 | | 6/1996 |
| JP | 10137207 | | 5/1998 |
| JP | 11504541 | | 4/1999 |
| JP | 2000510030 | | 8/2000 |
| JP | 2000510250 | | 8/2000 |
| JP | 2000358299 | | 12/2000 |
| JP | 2001070269 | | 3/2001 |
| JP | 2001522288 | | 11/2001 |
| JP | 2002051998 | | 2/2002 |
| JP | 2002113004 | | 4/2002 |
| JP | 2002522106 | | 7/2002 |
| JP | 2003509145 | | 3/2003 |
| JP | 2003511098 | | 3/2003 |
| JP | 2004305704 | | 11/2004 |
| JP | 2004350702 | | 12/2004 |
| JP | 2005131367 | | 5/2005 |
| JP | 2005536313 | | 12/2005 |
| JP | 2006511296 | | 4/2006 |
| JP | 2006525072 | | 11/2006 |
| JP | 2007021218 | | 2/2007 |
| JP | 2007530080 | | 11/2007 |
| JP | 2008149132 | | 7/2008 |
| JP | 2009505737 | | 2/2009 |
| JP | 2009135109 | | 6/2009 |
| JP | 2009136679 | | 6/2009 |
| JP | 2009539566 | | 11/2009 |
| JP | 2010082446 | | 4/2010 |
| JP | 2010510851 | | 4/2010 |
| JP | 2011504363 | | 2/2011 |
| JP | 2011507656 | | 3/2011 |
| JP | 2012509701 | | 4/2012 |
| JP | 2013188476 | | 9/2013 |
| JP | 2014503319 | | 2/2014 |
| JP | 2014506171 | | 3/2014 |
| JP | 2014511737 | | 5/2014 |
| JP | 2014514031 | | 6/2014 |
| JP | 2014516723 | | 7/2014 |
| JP | 2015036124 | | 2/2015 |
| JP | 2015524310 | | 8/2015 |
| JP | 2015528352 | | 9/2015 |
| JP | 2016510683 | | 4/2016 |
| JP | 2016511026 | | 4/2016 |
| JP | 2016123870 | | 7/2016 |
| JP | 2016144642 | | 8/2016 |
| JP | 2017023283 | | 2/2017 |
| JP | 2017047213 | | 3/2017 |
| JP | 2017514553 | | 6/2017 |
| JP | 2017532140 | | 11/2017 |
| JP | 2018501874 | | 1/2018 |
| JP | 2018534957 | | 11/2018 |
| JP | 2018200716 | | 12/2018 |
| JP | 2019005566 | | 1/2019 |
| JP | 2019005572 | | 1/2019 |
| JP | 2019530529 | | 10/2019 |
| JP | 2020032185 | | 3/2020 |
| JP | 2021512665 | | 5/2021 |
| WO | 9406349 | | 3/1994 |
| WO | 9905971 | | 2/1999 |
| WO | 200007501 | | 2/2000 |
| WO | 0040166 | | 7/2000 |
| WO | 0245608 | | 6/2002 |
| WO | 200245608 | | 6/2002 |
| WO | 2002045608 | | 6/2002 |

(56) References Cited

FOREIGN PATENT DOCUMENTS

| | | |
|---|---|---|
| WO | 03026722 | 4/2003 |
| WO | 2003026722 | 4/2003 |
| WO | 2004026134 | 4/2004 |
| WO | 2006060613 | 6/2006 |
| WO | 2007015199 | 2/2007 |
| WO | 2007024920 | 3/2007 |
| WO | 2007146864 | 12/2007 |
| WO | 2008014629 | 2/2008 |
| WO | 2009065042 | 5/2009 |
| WO | 2009090547 | 7/2009 |
| WO | 2011136867 | 11/2011 |
| WO | 2012068471 | 5/2012 |
| WO | 2012087899 | 6/2012 |
| WO | 2012092016 | 7/2012 |
| WO | 2012097067 | 7/2012 |
| WO | 2012100184 | 7/2012 |
| WO | 2012100185 | 7/2012 |
| WO | 2012110942 | 8/2012 |
| WO | 2012122517 | 9/2012 |
| WO | 2014124231 | 2/2013 |
| WO | 2013101257 | 7/2013 |
| WO | 2013123549 | 8/2013 |
| WO | 2014036439 | 3/2014 |
| WO | 2014059308 | 4/2014 |
| WO | 2014130169 | 8/2014 |
| WO | 2014137897 | 9/2014 |
| WO | 2015038607 | 3/2015 |
| WO | 2015061530 | 4/2015 |
| WO | 2015073962 | 5/2015 |
| WO | 2015148470 | 10/2015 |
| WO | 2015171393 | 11/2015 |
| WO | 2016020800 | 2/2016 |
| WO | 2016061384 | 4/2016 |
| WO | 2016068923 | 5/2016 |
| WO | 2016183179 | 11/2016 |
| WO | 2016183285 | 11/2016 |
| WO | 2016183468 | 11/2016 |
| WO | 2017040581 | 3/2017 |
| WO | 2017053921 | 3/2017 |
| WO | 2017125794 | 7/2017 |
| WO | 2017192769 | 11/2017 |
| WO | 2017192775 | 11/2017 |
| WO | 2018010659 | 1/2018 |
| WO | 2018071490 | 4/2018 |
| WO | 2018130976 | 7/2018 |
| WO | 2018144765 | 8/2018 |
| WO | 2019040458 | 2/2019 |
| WO | 2019083982 | 5/2019 |
| WO | 2019144103 | 7/2019 |
| WO | 2019152986 | 8/2019 |
| WO | 2019195354 | 10/2019 |
| WO | 2019217430 | 11/2019 |
| WO | 2020097438 | 5/2020 |
| WO | 2020142539 | 7/2020 |
| WO | 2020214962 | 10/2020 |
| WO | 2020247619 | 12/2020 |
| WO | 2021102230 | 5/2021 |
| WO | 2022178077 | 8/2022 |
| WO | 2023009586 | 2/2023 |
| WO | 2023009589 | 2/2023 |
| WO | 2023018937 | 2/2023 |
| WO | 2024238905 | 11/2024 |

OTHER PUBLICATIONS

Gulrajani, Ramesh M. "The Forward and Inverse Problems of Electrocardiography", IEEE Engineering In Medicine And Biology Magazine, IEEE Service Center, Piscataway, NJ, U.S., vol. 17, No. 5, Sep. 1, 1998, pp. 84-101, 122.

Liu, Zhongming et al. "Noninvasive Reconstruction of Three-Dimensional Ventricular Activation Sequence From the Inverse Solution of Distributed Equivalent Current Density", IEEE Transactions On Medical Imaging, IEEE Service Center, Piscataway, NJ, U.S., vol. 25, No. 10, Oct. 1, 2006, pp. 1307-1318.

Martin, David R. et al. "Projected Tikhonov Regularization of Large-Scale Discrete Ill-Posed Problems", Journal of Scientific Computing, Springer U.S., Boston, MA vol. 56, No. 3, Feb. 10, 2013, pp. 471-493.

Ramanathan, Charulatha et al. "Noninvasive Electrocardiogramaging (ECGI): Application of the Generalized Minimal Residual (GMRes) Method", Annals of Biomedical Engineering, vol. 31, No. 8, Sep. 1, 2003, pp. 981-994.

Extended European Search Report dated Sep. 13, 2019 issued in corresponding European Application No. 17793286.0.

Office Action issued on Apr. 27, 2016 in corresponding Canadian Application No. 2,747,859.

Anoop Kumar Gupta, et al., "Point of View Cardiac Mapping: Utility or Futility?", Non-contact Endocardial Mapping Indian Pacing and Electrophysiology Journal, vol. 2, No. 1, Jan. 1, 2002, pp. 20-32 XP055128732.

Christoph Scharft et al. Declaration under 37 C.F.R. 1.132, Nov. 15, 2012.

Australian Examination Report dated Jun. 28, 2018, issued in corresponding Australian Patent Application No. 2014318872.

Australian Office Action dated Feb. 26, 2018 issued in Australian Application No. 2017201560.

Australian Office Action dated Jun. 14, 2018 issued in Australian Application No. 2014214756.

Australian Office Action dated Mar. 17, 2018 issued in corresponding Australian Application No. 2013308531.

Canadian Office Action dated Apr. 26, 2017 issued in corresponding Canadian Application No. 2932956.

Canadian Office Action dated Jan. 22, 2018 issued in corresponding Canadian Application No. 2932956.

Canadian Office Action dated Mar. 30, 2017 issued in corresponding Canadian Application No. 2747859.

Canadian Office Action dated Nov. 27, 2017 issued in corresponding Canadian Application No. 2829626.

Chinese Office Action dated Apr. 17, 2017 issued in corresponding Chinese Application No. 201480018328.4.

Decision dated Jan. 16, 2018 issued for European Patent Application No. 09702094.5.

Decision dated Jan. 18, 2018 issued for European Patent Application No. 13176658.6.

Canadian Office Action dated Oct. 29, 2018 issued in corresponding Canadian Application No. 2829626.

European Office Action dated Apr. 23, 2018 issued in corresponding European Application No. 07785075.8.

European Office Action dated Apr. 28, 2014, issued in corresponding European Application No. 09 702 094.5-1660.

European Office Action dated Feb. 29, 2016 issued in corresponding European Application No. 07 785 075.8-1657.

European Office Action dated Jan. 31, 2018, issued in corresponding European Application No. 13763151.1.

European Office Action dated Mar. 21, 2017 issued in corresponding European Application No. 07785075.8.

Extended European Search Report dated Mar. 14, 2017 issued in corresponding European Application No. EP14843283.4.

Extended European Search Report dated Oct. 18, 2017, issued in European Application No. 15768711.

International Search Report and Written Opinion dated Aug. 4, 2017 issued in corresponding International Application No. PCT/US17/30915.

International Search Report and Written Opinion dated Dec. 12, 2017 issued in corresponding International Application No. PCT/US2017/056064.

International Search Report and Written Opinion dated Jun. 26, 2015 issued in International Application No. PCT/US2015/022187.

International Search Report and Written Opinion dated Sep. 25, 2017, issued in corresponding Application No. PCT/US17/30922.

International Search Report dated Mar. 10, 2015 issued in corresponding International Application No. PCT/US14/54942.

International Search Report issued Apr. 14, 2008 in related International Application No. PCT/CH2007/000380.

Invitation to Pay Additional Fees issued on Jan. 8, 2014 in corresponding International Application No. PCT/US2013/057579.

(56) References Cited

OTHER PUBLICATIONS

ISRWO dated Aug. 8, 2016 issued in corresponding European Application No. PCT/US2016/031823.
ISRWO dated Aug. 11, 2016 issued in corresponding International Application No. PCT/US2016/032017.
ISRWO dated Aug. 18, 2016 issued in corresponding International Application No. PCT/US16/32420.
ISRWO issued on May 20, 2014 in International application No. PCT/US14/15261.
Japanese Notice of Allowance dated Feb. 27, 2018 issued in corresponding Japanese Application No. 2015-530101, with English language translation.
Japanese Notice of Allowance dated Jul. 11, 2017 issued in corresponding Japanese Application No. 2013-557-926, with English language summary.
Japanese Notice of Allowance dated Sep. 18, 2018 issued in corresponding Japanese Application No. 2015-557091, with English language translation.
Japanese Office Action dated Aug. 28, 2018 issued in corresponding Japanese Application No. 2016-542062, with machine translation to English.
Japanese Office Action dated Feb. 16, 2016 issued in corresponding Japanese Application No. 2013-557-926, with English language summary.
Japanese Office Action dated Jan. 31, 2017 issued in corresponding Japanese Application No. 2013-557-926, with English language summary.
Japanese Office Action dated Jun. 27, 2017 issued in corresponding Japanese Application No. 2015-530101, with English language translation.
Japanese Office Action dated Sep. 26, 2017 issued in corresponding Japanese Application No. 2017-155346, with English translation.
Office Action dated Nov. 7, 2017, issued in European Application No. 15768711.
Japanese Office Action dated Oct. 10, 2017, issued in Japanese Application No. 2015-557091 with machine translation to English.
Office Action issued on Mar. 9, 2016 in corresponding European Patent Application No. 13176658.6.
Office Action issued on May 30, 2016 in related Australian Patent Application No. 2012225250.
Office Action issued on Oct. 4, 2013 in corresponding Canadian Patent Application No. 2,659,898.
PCT ISRWO dated Jun. 5, 2014, issued in corresponding PCT Application No. PCT/US2013/057579.
Della Bella et al. "Non-contact mapping to guide catheter ablation of untolerated ventrical tachycardia" European Heart Journal, May 2002, 23(9)742-752.
Examination report dated Jul. 6, 2017 issued in Australian Patent Application No. 2014214756.
Examination Report dated Jun. 27, 2017 issued in Australian Application No. 2013308531.
Examiner's Report Dated Dec. 22, 2015 in related Canadian Application No. 2656898.
Extended European Search Report for related Application No. 13176658 dated Sep. 29, 2014.
Extended European Search Report issued Jul. 8, 2016 in related European Application No. 14748567.6.
Gupta et al. "Point of view cardiac mapping; utility or futility? Non-contact endocardial mapping" Indian Pacing and Electrophysiology Journal2:2Q-32 (2002).
He et al. "An equivalent body surface charge model representing three-dimensional bioelectrical activity" IEEE Transactions on Biomedical Engineering, 42.7 (Jul. 7, 1995) pp. 637-646.
International Search Report and Written Opinion in related Application No. PCT/US2012/028593 dated Mar. 5, 2013.
International Search Report in related Application No. PCT/IB2009/000071 dated Oct. 7, 2009.
Extended European Search Report dated Oct. 4, 2018 issued in corresponding European Application No. 16793503.0.
Jackson, JD, "Surface Distributions of Charges and Dipoles and Discontinuities in the Electric Field and Potential", Classical Electrodynamics, 3rd edition, Dec. 1998, pp. 31-34.
Leif et al., "Geometric modeling based on polygonal meshes". Eurographics 2000 Tutorial, Aug. 21, 2000.
Office Action issued on Mar. 9, 2016 in corresponding European Patent Application No. 09702094.5.
Partial European Search Report dated Apr. 29, 2014 in corresponding European Application No. 13176658.
Patent Examination Report No 3 issued on Sep. 21, 2016 in related Australian Application No. 2012225250.
Pullan et al. "The inverse problem of electrocardiology" Northeastern University Electrical and Computer Engineering, Feb. 23, 2007.
Van Oosterom A: "Solidifying the solid angle." 2002 Journal of Electrocardiology 2002 vol. 35 Suppl pp. 181-192 ISSN: 0022-0736.
William G. Stevenson et al: "Recording Techniques for Clinical Electrophysiology" Journal of Cardiovascular Electrophysiology. vol. 16 No. 91, Sep. 2005, pp. 1017-1022.
Wolfgang Nolting: Elektrodynamik—Grundkurs Theoretische Physik 3, Springer Spectrum, p. 89-91, XP009188752.
Japanese Notice of Allowance dated Jan. 16, 2018 issued in corresponding Japanese Application No. 2017-155346, with English translation.
Ramanathan, C. et al. "Noninvasive Electrocardiogramaging (ECGI): Application of the Generalized Minimal Residual (GMRes) Method", Annals Of Biomedical Engineering, vol. 31 No. 8 (2003), pp. 981-994.
European Office Action dated Jul. 21, 2020 issued in corresponding European Application No. 17793291.0.
Chinese Office Action dated Mar. 3, 2021 issued in corresponding Chinese Application No. 201780040472.1.
Coll-Font et al. "New Additions to the Toolkit for Forward/Inverse Problems in Electrocardiogramathin the SCIRun Problem Solving Environment", Computing in Cardiology, 2014, vol. 41, pp. 213-216.
Japanese Office Action dated Apr. 6, 2021 issued in corresponding Japanese Application No. 2018-557371, with machine translation to English.
Australian Examination Report Dated Jul. 26, 2021 issued in related Australian Application No. 2017260453.
Japanese Notice of Allowance dated Aug. 3, 2021 issued in corresponding Japanese Application No. 2018-557371, with machine translation to English.
Israel Office Action dated Oct. 21, 2021 issued in corresponding Israel Application No. 262730, with English translation.
Extended European Search Report dated Feb. 25, 2022 issued in related European Application No. 21192952.6.
Japanese Office Action dated Aug. 23, 2022 issued in corresponding Japanese Application No. 2018-557371, with machine translation to English.
Chinese Office Action dated Feb. 27, 2025 issued in Chinese Application No. 202111503914.6, with machine translation to English.
European Office Action dated Apr. 15, 2025 issued in European Application No. 17793286.0.
Gepstein et al. "Electroanatomical Mapping of the Heart: Basic Concepts and Implications for the Treatment of Cardiac Arrhythmias", PACE—Pacing and Clinical Electrophysiology, vol. 21, No. 6, Jun. 1, 1998, pp. 1268-1278, XP093268784, US ISSN: 0147-8389, DOI: 10.1111/j.1540-8159.1998.tb00187.x.
Sy et al. "Modern Electrophysiology Mapping Techniques", Heart, Lung and Circulation, vol. 21, No. 6 , pp. 364-375, XP028429030, ISSN: 1443-9506, DOI: 10.1016/J.HLC.2012.04.007, retrieved on Apr. 20, 2012.
European Office Action dated Jul. 20, 2022 issued in European Application No. 17793286.0.
European Office Action dated Jan. 13, 2025 issued in European Application No. 21192952.6.
European Office Action dated Apr. 2, 2026 issued in European Application No. 17793286.0.

(56) References Cited

OTHER PUBLICATIONS

Anatomy Warehouse, "Axis Heart Model", 2014, pp. 1-3, at http://www.anatomywarehouse.com/axis-scientific-2-part-deluxe-life-size-human-heart-a-104269. (Year: 2014).
International Search Report and Written Opinion dated Jan. 14, 2020 issued in International Application No. PCT/US2019/060433.
Cuesta-Frau et al. "Unsupervised classification of ventricular extrasystoles using bounded clustering algorithms and morphology matching", Medical & Biological Engineering & Computing, vol. 45, No. 3, Nov. 9, 2006, pp. 229-239, XP019486699, ISSN: 1741-0444.
Ravelli et al. "Wave Similarity Mapping Shows the Spatiotemporal Distribution of Fibrillatory Wave Complexity in the Human Right Atrium During Paroxysmal and Chronic Atrial Fibrillation", Journal of Cardiovascular Electrophysiology, vol. 16, No. 10 (Oct. 2005) pp. 1071-1076.
Acharya et al. "Heart rate variability: a review," Med Bio Eng Comput (2006) 44:1031-1051; DOI 10.1007/s11517-006-0119-0. ( Year: 2006).
Bhat V R et al: "Construction of Dynamic Lead Fields from Vectorcardiography to Solve the Forward and the Inverse Problems in Magnetocardiography", IRBM, Elsevier, Amsterdam, NL, vol. 42, No. 5, Oct. 26, 2020, pp. 313-323, XP086788833, ISSN: 1959-0318, DOI: 10.1016/J.IRBM.2020.10.004.
International Preliminary Report on Patentability dated Dec. 4, 2025 issued in International Application No. PCT/US2024/030585.
International Preliminary Report on Patentability dated May 7, 2026 issued in International Application No. PCT/US2024/052379.
International Search Report and Written Opinion dated Apr. 8, 2019 issued in International Application No. PCT/US19/14498.
International Search Report and Written Opinion dated Aug. 27, 2024 issued in International Application No. PCT/US2024/029904.
International Search Report and Written Opinion dated Aug. 8, 2016 issued in International Application No. PCT/US2016/031823.
International Search Report and Written Opinion dated Jan. 31, 2025 issued in International Application No. PCT/US2024/052379.
International Search Report and Written Opinion dated Jul. 21, 2020 issued in International Application No. PCT/US2020/028779.
International Search Report and Written Opinion dated Jul. 23, 2019 issued in International Application No. PCT/US2019/031131.
International Search Report and Written Opinion dated Jul. 7, 2022 issued in International Application No. PCT/US22/16722.
International Search Report and Written Opinion dated Mar. 26, 2021 issued in International Application No. PCT/US20/61458.
International Search Report and Written Opinion dated May 20, 2014 issued in International Application No. PCT/US14/15261.
International Search Report and Written Opinion dated Nov. 18, 2022 issued in International Application No. PCT/US2022/040163.
International Search Report and Written Opinion dated Oct. 25, 2022 issued in International Application No. PCT/US2022/038464.
International Search Report and Written Opinion dated Oct. 31, 2022 issued in International Application No. PCT/US2022/038461.
International Search Report and Written Opinion dated Sep. 14, 2020 issued in International Application No. PCT/US2020/036110.
International Search Report and Written Opinion dated Sep. 18, 2024 issued in International Application No. PCT/US2024/030585.
International Search Report issued Apr. 21, 2008 in International Application No. PCT/CH2007/000380.
Latchamsetty et al., "Complex Fractionated Atrial Electrograms: A Worthwhile Target for Ablation of Atrial Fibrillation?" Circulation: Arrhythmia and Electrophysiology, vol. 4, Issue 2, Apr. 1, 2011, pp. 117-118.
Nakano Yuki et al: "ECG Localization Method Based on Volume Conductor Model and Kalman Filtering", Sensors, vol. 21, No. 13, Jun. 22, 2021, p. 4275, XP093239191, CH, ISSN: 1424-8220, DOI: 10.3390/s21134275.
Ravon Gwladys et al: "A Parameter Optimization to Solve the Inverse Problem in Electrocardiogramay", May 23, 2017, SAT 2015 18th International Conference, Austin, TX, USA, Sep. 24-27, 2015; [Lecture Notes in Computer Science; Lect.Notes Computer], Springer, Berlin, Heidelberg, p. 219-229, XP047414937, ISBN: 978-3-540-74549-5.
Simitev et al. "Asymptotics of Conduction Velocity Restitution in Models of Electrical Excitation in the Heart", Bulletin of Mathematical Biology, vol. 73, No. 1 (Mar. 5, 2010), pp. 72-115. ISSN: 0092-8240, DOI: 10.1007/s11538-010-9523-6 URL: https://link.springer.com/article/10.1 007/s11538-010-9523-6>.
The Hutchinson Unabridged Encyclopedia With Atlas and Weather Guide. "What Is A Database?" Accessed on the internet: http://search.credoreference.com/content/entry/heliconhe/what_is_a_database/O?institutionld=743 (Year: 2018).
Van Oosterom A et al.: "A Parameterized Description of Transmembrane Potentials Used in Forward and Inverse Procedures", Int. Conf. Electrocardiol. 6, Aug. 1, 2005, pp. 5-8, XP093239356.
Weber et al. "Conduction Velocity Restitution of the Human Atrium-An Efficient Measurement Protocol for Clinical Electrophysiological Studies," IEEE Transactions On Biomedical Engineering, vol. 58, No. 9, Sep. 2011; Digital Object Identifier 10.1109/TBME.2011.2160453. (Year: 2011).

* cited by examiner

Images Simulated 50ms after focal activation with varying Propagation History Time Widows Propagation History Map during AF Propagation History=50ms Time T = 9ms
After Activation
at Point X Time T = 12ms
After Activation
at Point X Time T = 47ms
After Activation
at Point X Activation Time At Point X

CARDIAC INFORMATION DYNAMIC DISPLAY SYSTEM AND METHOD

RELATED APPLICATIONS

The present application claims priority under 35 USC 119(e) to U.S. Provisional Patent Application Ser. No. 62/331,351, entitled "Cardiac Information Dynamic Display System And Method", filed May 3, 2016, which is incorporated herein by reference in its entirety.

The present application, while not claiming priority to, may be related to U.S. patent application Ser. No. 14/865,435, entitled "Method and Device for Determining and Presenting Surface Charge and Dipole Densities on Cardiac Walls", filed Sep. 25, 2015, which is a continuation of U.S. Pat. No. 9,167,982, entitled "Method and Device for Determining and Presenting Surface Charge and Dipole Densities on Cardiac Walls", filed Nov. 19, 2014, which is a continuation of U.S. Pat. No. 8,918,158 (hereinafter the '158 patent), entitled "Method and Device for Determining and Presenting Surface Charge and Dipole Densities on Cardiac Walls", issued Dec. 23, 2014, which is a continuation of U.S. Pat. No. 8,700,119 (hereinafter the '119 patent), entitled "Method and Device for Determining and Presenting Surface Charge and Dipole Densities on Cardiac Walls", issued Apr. 15, 2014, which is a continuation of U.S. Pat. No. 8,417,313 (hereinafter the '313 patent), entitled "Method and Device for Determining and Presenting Surface Charge and Dipole Densities on Cardiac Walls", issued Apr. 9, 2013, which was a 35 USC 371 national stage filing of PCT Application No. CH2007/000380, entitled "Method and Device for Determining and Presenting Surface Charge and Dipole Densities on Cardiac Walls", filed Aug. 3, 2007, published as WO 2008/014629, which claimed priority to Swiss Patent Application No. 1251/06 filed Aug. 3, 2006, each of which is hereby incorporated by reference.

The present application, while not claiming priority to, may be related to U.S. patent application Ser. No. 14/886,449, entitled "Device and Method for the Geometric Determination of Electrical Dipole Densities on the Cardiac Wall", filed Oct. 19, 2015, which is a continuation of U.S. Pat. No. 9,192,318, entitled "Device and Method for the Geometric Determination of Electrical Dipole Densities on the Cardiac Wall", filed Jul. 19, 2013, which is a continuation of U.S. Pat. No. 8,512,255, entitled "Device and Method for the Geometric Determination of Electrical Dipole Densities on the Cardiac Wall", issued Aug. 20, 2013, published as US2010/0298690 (hereinafter the '690 publication), which was a 35 USC 371 national stage application of Patent Cooperation Treaty Application No. PCT/IB09/00071 filed Jan. 16, 2009, entitled "A Device and Method for the Geometric Determination of Electrical Dipole Densities on the Cardiac Wall", published as WO2009/090547, which claimed priority to Swiss Patent Application 00068/08 filed Jan. 17, 2008, each of which is hereby incorporated by reference.

The present application, while not claiming priority to, may be related to U.S. application Ser. No. 14/003,671, entitled "Device and Method for the Geometric Determination of Electrical Dipole Densities on the Cardiac Wall", filed Sep. 6, 2013, which is a 35 USC 371 national stage filing of Patent Cooperation Treaty Application No. PCT/US2012/028593, entitled "Device and Method for the Geometric Determination of Electrical Dipole Densities on the Cardiac Wall", published as WO2012/122517 (hereinafter the '517 publication), which claimed priority to U.S. Patent Provisional Application Ser. No. 61/451,357, each of which is hereby incorporated by reference.

The present application, while not claiming priority to, may be related to U.S. Design application Ser. No. 29/475,273, entitled "Catheter System and Methods of Medical Uses of Same, Including Diagnostic and Treatment Uses for the Heart", filed Dec. 2, 2013, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, which claims priority to U.S. Patent Provisional Application Ser. No. 61/695,535, entitled "System and Method for Diagnosing and Treating Heart Tissue", filed Aug. 31, 2012, which is hereby incorporated by reference.

The present application, while not claiming priority to, may be related to Patent Cooperation Treaty Application No. PCT/US2014/15261, entitled "Expandable Catheter Assembly with Flexible Printed Circuit Board (PCB) Electrical Pathways", filed Feb. 7, 2014, which claims priority to U.S. Patent Provisional Application Ser. No. 61/762,363, entitled "Expandable Catheter Assembly with Flexible Printed Circuit Board (PCB) Electrical Pathways", filed Feb. 8, 2013, which is hereby incorporated by reference.

The present application, while not claiming priority to, may be related to Patent Cooperation Treaty Application No. PCT/US2015/11312, entitled "Gas-Elimination Patient Access Device", filed Jan. 14, 2015, which claims priority to U.S. Patent Provisional Application Ser. No. 61/928,704, entitled "Gas-Elimination Patient Access Device", filed Jan. 17, 2014, which is hereby incorporated by reference.

The present application, while not claiming priority to, may be related to Patent Cooperation Treaty Application No. PCT/US2015/22187, entitled "Cardiac Analysis User Interface System and Method", filed Mar. 24, 2015, which claims priority to U.S. Patent Provisional Application Ser. No. 61/970,027, entitled "Cardiac Analysis User Interface System and Method", filed Mar. 28, 2014, which is hereby incorporated by reference.

The present application, while not claiming priority to, may be related to Patent Cooperation Treaty Application No. PCT/US2014/54942, entitled "Devices and Methods for Determination of Electrical Dipole Densities on a Cardiac Surface", filed Sep. 10, 2014, which claims priority to U.S. Patent Provisional Application Ser. No. 61/877,617, entitled "Devices and Methods for Determination of Electrical Dipole Densities on a Cardiac Surface", filed Sep. 13, 2013, which is hereby incorporated by reference.

The present application, while not claiming priority to, may be related to U.S. Patent Provisional Application Ser. No. 62/161,213, entitled "Localization System and Method Useful in the Acquisition and Analysis of Cardiac Information", filed May 13, 2015, which is hereby incorporated by reference.

The present application, while not claiming priority to, may be related to U.S. Patent Provisional Application Ser. No. 62/160,501, entitled "Cardiac Virtualization Test Tank and Testing System and Method", filed May 12, 2015, which is hereby incorporated by reference.

The present application, while not claiming priority to, may be related to U.S. Patent Provisional Application Ser. No. 62/160,529, entitled "Ultrasound Sequencing System and Method", filed May 12, 2015, which is hereby incorporated by reference.

FIELD

The present invention is generally related to systems and methods that may be useful for the diagnosis and treatment of cardiac arrhythmias or other abnormalities, in particular, the present invention is related to systems, devices, and methods useful in displaying cardiac activities associated with diagnosing and treating such arrhythmias or other abnormalities.

BACKGROUND

Cardiac signals (e.g., charge density, dipole density, voltage, etc.) vary across the endocardial surface in magnitude. The magnitude of these signals is dependent on several factors, including local tissue characteristics (e.g., healthy vs. disease/scar/fibrosis/lesion) and regional activation characteristics (e.g., "electrical mass" of activated tissue prior to activation of the local cells). A common practice is to assign a single threshold for all signals at all times across the surface. The use of a single threshold can cause low-amplitude activation to be missed or cause high-amplitude activation to dominate/saturate, leading to confusion in interpretation of the map. Failure to properly detect activation can lead to imprecise identification of regions of interest for therapy delivery or incomplete characterization of ablation efficacy (excess or lack of block).

The continuous, global mapping of atrial fibrillation yields a tremendous volume of temporally- and spatially-variable activation patterns. A limited, discrete sampling of map data may be insufficient to provide a comprehensive picture of the drivers, mechanisms, and supporting substrate for the arrhythmia. Clinician review of long durations of AF can be challenging to remember and piece together to complete the "bigger picture."

SUMMARY

In accordance with aspects of the inventive concept, provided is a cardiac information dynamic display system, comprising one or more electrodes configured to record sets of electric potential data representing cardiac activity at a plurality of time intervals and a cardiac information console. The cardiac information console comprises a signal processor, which is configured to calculate sets of cardiac activity data at the plurality of time intervals using the recorded sets of electric potential data, wherein the cardiac activity data is associated with surface locations of one or more cardiac chambers and calculate a series of activation wavefront locations for each set of cardiac activity data. The system also includes a user interface module configured to display a series of images. Each image comprises a graphical representation of a propagation of the activation wavefront locations on a graphical representation of surfaces of the one or more cardiac chambers, wherein the graphical representation of the propagation of the activation wavefront locations is based on a time window.

In various embodiments, the one or more electrodes comprise a 3D electrode array configured for insertion into the one or more cardiac chambers.

In various embodiments, the 3D array is a basket array, a spiral array, a balloon, radially deployable arms, and/or other expandable and compactible structures.

In various embodiments, the 3D array includes a plurality of splines.

In various embodiments, the 3D array includes a plurality of ultrasound transducers and the one or more electrodes disposed on the splines, wherein the plurality of ultrasound transducers is configured to generate image data used by the user interface module to generate the graphical representation of the surfaces of the one or more cardiac chambers as a 3-dimensional reconstruction of the one or more cardiac chambers.

In various embodiments, one or more of the plurality of splines include at least one electrode and at least one ultrasound transducer.

In various embodiments, one or more of the plurality of splines include at least one electrode-ultrasound transducer pair.

In various embodiments, the one or more electrodes comprise one or more skin electrodes.

In various embodiments, the signal processor is configured to calculate surface charge densities, such as cardiac activity data, from the set of electric potential data for each time interval from the plurality of time intervals and to calculate the series of activation wavefront locations for the time interval based on the surface charge densities.

In various embodiments, the signal processor is configured to calculate dipole densities, such as cardiac activity data, from the set of electric potential data for each time interval from the plurality of time intervals and to calculate the series of activation wavefront locations for the time interval based on the dipole densities.

In various embodiments, the signal processor is configured to calculate a discrete set of cardiac activity data from the electric potential data for each time interval from the plurality of time intervals, without aggregation of cardiac activity data or electric potential data from previous time intervals.

In various embodiments, each time interval is less than or equal to one cardiac cycle.

In various embodiments, each time interval is about 10 ms or less.

In various embodiments, each time interval is about 1 ms or less.

In various embodiments, each time interval is 0.3 ms±0.05 ms.

In various embodiments, the one or more electrodes are responsive to the signal processor to record the sets of electric potential data for the plurality of time intervals for at least about 100 ms.

In various embodiments, the one or more electrodes are responsive to the signal processor to record the sets of electric potential data for the plurality of time intervals for up to about 30 seconds.

In various embodiments, the cardiac information console is configured to represent the surfaces of the one or more cardiac chambers as a plurality of nodes, and the activation wavefront locations represent nodes determined to have an activated state based on the sets of cardiac activity data.

In various embodiments, the number of nodes is at least about 3,000 nodes.

In various embodiments, the number of nodes is not more than about 10,000 nodes.

In various embodiments, the propagation of the activation wavefront locations on the graphical representation of surfaces of the one or more cardiac chambers represents an activated state moving from node to node over at least a portion of the graphical representation of surfaces of the one or more cardiac chambers.

In various embodiments, for each time interval, the signal processor is configured to calculate a discrete set of cardiac activity data for the plurality of nodes.

In various embodiments, for each time interval, the signal processor is configured to determine one of a plurality of activation states of one or more nodes from the plurality of nodes based on the set of cardiac activation data calculated for the time interval, wherein the plurality of activation states includes an activated state and at least one other state.

In various embodiments, for each time interval, the signal processor is configured to determine an activation state from the plurality of activation states for each node in the plurality of nodes for the time interval.

In various embodiments, the signal processor is configured to determine the activation state for each of the one or more nodes with reference to a threshold value.

In various embodiments, the threshold value is the same for each node in a time interval.

In various embodiments, the threshold value is different for two or more nodes in a time interval.

In various embodiments, the threshold value is a non-dynamic value that does not change from time interval to time interval.

In various embodiments, the non-dynamic value is a set percentage of a max range relative to a zero value for the cardiac activity data.

In various embodiments, the threshold value is a dynamic threshold value independently calculated for different nodes or groups of nodes.

In various embodiments, the dynamic threshold value is a time-dependent dynamic threshold value determined by analysis of, or mathematical operation on, one or more cardiac activation parameters taken from a group consisting of: voltage biopotential, surface charge density, dipole density, or a combination of two or more thereof.

In various embodiments, the threshold value is a dynamic value and the signal processor is configured to change the dynamic value for at least some of the one or more nodes across two or more time intervals.

In various embodiments, the signal processor is configured to adjust the dynamic value to account for temporal, spatial, global, regional, and/or local differences at different points in time of the one or more cardiac chambers.

In various embodiments, the signal processor is configured to determine the cardiac activity data for a node in each time interval using cardiac activity data from neighboring nodes in the same time interval to smooth the graphical representation of the propagation of the activation wavefront locations.

In various embodiments, the signal processor is configured to determine the cardiac activity data for the node by taking a time derivative of the cardiac activity data of the neighboring nodes.

In various embodiments, the signal processor is configured to determine the cardiac activity data at the node using Coulombian averaging with the neighboring nodes.

In various embodiments, the signal processor is configured to calculate the cardiac activity data as the Coulombian of surface charge density, and the user interface module is configured to display the Coulombian of the surface charge density.

In various embodiments, the signal processor is configured to calculate the cardiac activity data as the Coulombian of surface dipole density and the user interface module is configured to display the Coulombian of the surface dipole density.

In various embodiments, the signal processor is configured to calculate the cardiac activity data as the Coulombian of the surface voltage and the user interface module is configured to display the Coulombian of the surface voltage.

In various embodiments, the signal processor is configured to use 2nd neighboring nodes to determine the cardiac activity data for the node.

In various embodiments, the signal processor is configured to also use 3rd neighboring nodes to determine the cardiac activity data for the node.

In various embodiments, the signal processor is configured to use more than 3rd neighboring nodes to determine the cardiac activity data for the node.

In various embodiments, the signal processor is configured to smooth the activation wavefront using a smoothing filter and/or a noise reduction filter, wherein the smoothing filter and/or a noise reduction filter is a median filter or other nonlinear filter used to remove noise from a node based set of data.

In various embodiments, the signal processor is configured to replace the value at each node with a median value of the node along with its neighbor nodes.

In various embodiments, the number of neighbor nodes is user defined, pre-determined, and/or a time varying value.

In various embodiments, the signal processor is configured to determine the activation wavefront by taking a weighted spatial derivative of the cardiac activity at each node.

In various embodiments, the weighting comprises uniform weighting.

In various embodiments, the weighting comprises distance-based weighting.

In various embodiments, the signal processor is further configured to: define a plurality of node activation states, including the activated state; define an activation display scale as a set of time increments measured from a reference time, wherein each time increment is associated with a different node activation state; and based on the cardiac activity data and the activation display scale, associate one of the plurality of node activation states with one or more nodes from the plurality of nodes relative to the reference time.

In various embodiments, the activation states include the activated state and one or more recently activated states.

In various embodiments, the one or more recently activated states is a plurality of recently activated states.

In various embodiments, the activated state and each recently activated state is associated with a different time increment of the activation display scale.

In various embodiments, the cardiac information console is configured to associate one of a plurality of graphical indicia with each activation state.

In various embodiments, the plurality of graphical indicia includes one or more of different colors, different hues, different lines, different line patterns, different sizes or forms of dots or stippling, different opacities, and/or different textures.

In various embodiments, the user interface module is configured to display the plurality of graphical indicia as a graphical key in conjunction with the graphical representation of the propagation of the activation wavefront.

In various embodiments, the user interface module is configured to display each image in the series of images to include the plurality of graphical indicia selectively associated with one or more of the plurality of nodes, wherein a graphical indicia associated with a node is chosen as a function of an activation state of the node.

In various embodiments, the user interface module is configured to display each image in the series of images to include a color from a plurality of colors selectively associated with each one or more of the plurality of nodes, wherein each color represents a different activation state, and wherein the color associated with a node is chosen as a function of an activation state of the node.

In various embodiments, the user interface module is configured to color code each node as a function of an activation state associated with the node, wherein each activation state is represented by a different color, hue, and/or opacity.

In various embodiments, the user interface module is configured to present at least one user input device configured to enable a user to select the activation display scale.

In various embodiments, the user interface module is configured to display at least a portion of the sets of cardiac activity data in conjunction with the graphical representation of the propagation of the activation wavefront.

In various embodiments, the user interface module is configured to display the at least a portion of the sets of cardiac activity data in the form of an electrocardiogram (ECG or EKG) and/or electrogram (EGM).

In various embodiments, the user interface module is configured to display the time window in conjunction with the at least a portion of the sets of cardiac activity data.

In various embodiments, the user interface module is configured to display the time window as an image moving relative to and/or over the ECG or EKG and/or EGM in synchronization with the graphical representation of the propagation of the activation wavefront.

In various embodiments, the time window image is a semitransparent window superimposed over at least a portion of the ECG or EKG and/or EGM.

In various embodiments, the user interface module is configured to present at least one user input device configured to enable a user to select a width of the time window.

In various embodiments, the user interface module is configured to present at least one user input device configured to enable a user to adjust features of the graphical representation of the propagation of the activation wavefront on the graphical representation of the surfaces of the one or more cardiac chambers.

In various embodiments, the user interface module is responsive to a user input to rotate and/or scale the graphical representation of the one or more cardiac chambers.

In various embodiments, the user interface module is responsive to a user input to pause, rewind, and play the series of images within the time window.

In various embodiments, the user interface module is responsive to a user input to adjust the display speed of the series of images within the time window.

In various embodiments, the user interface module is configured to display an origin of activation on the graphical representation of surfaces of the one or more cardiac chambers.

In various embodiments, the graphical representation of the propagation of the activation wavefront locations in the graphical representation of surfaces of the one or more cardiac chambers represents one or more of: regions of frequent activation representing major pathways; maximum local delay time as an approximation for conduction delay; max/min/threshold conduction velocity; minimum local reactivation period as an approximation of minimum refractory period; harmonic organization index as a degree of spectral energy at specific frequencies and its harmonics; peak negative signal; peak-to-peak amplitude; continuous trajectory, including continuous lines following the directional pattern of the wave front, with highlighting of areas of congestion and convergence; directional dispersion as a variance in direction of propagation; and/or angular velocity.

In accordance with various aspects of the inventive concept, provided is a cardiac information dynamic display method. The method comprises recording sets of electric potential data representing cardiac activity at a plurality of time intervals with one or more electrodes and providing a cardiac information console comprising a signal processor and a user interface module. The method further includes using the signal processor and the user interface module: calculating sets of cardiac activity data at the plurality of time intervals using the recorded sets of electric potential data, including associating the cardiac activity data with surface locations of one or more cardiac chambers; calculating a series of activation wavefront locations for each set of cardiac activity data; and displaying a series of images. Each image comprises a graphical representation of a propagation of the activation wavefront locations on a graphical representation of surfaces of the one or more cardiac chambers, wherein the graphical representation of the propagation of the activation wavefront locations is based on a time window.

In various embodiments, the one or more electrodes comprise a 3D electrode array configured for insertion into the one or more cardiac chambers.

In various embodiments, the 3D array is a basket array, a spiral array, a balloon, radially deployable arms, and/or other expandable and compactible structures.

In various embodiments, the 3D array includes a plurality of splines.

In various embodiments, the 3D array includes a plurality of ultrasound transducers and the one or more electrodes disposed on the splines, and the method includes: generating, using the plurality of ultrasound transducers, image data used by the user interface module to generate the graphical representation of the surfaces of the one or more cardiac chambers as a 3-dimensional reconstruction of the one or more cardiac chambers.

In various embodiments, one or more of the plurality of splines include at least one electrode and at least one ultrasound transducer.

In various embodiments, one or more of the plurality of splines include at least one electrode-ultrasound transducer pair.

In various embodiments, the one or more electrodes comprise one or more skin electrodes.

In various embodiments, the method further comprises calculating surface charge densities, such as cardiac activity data, from the set of electric potential data for each time interval from the plurality of time intervals and calculating the series of activation wavefront locations for the time interval based on the surface charge densities.

In various embodiments, the method further comprises calculating dipole densities, such as cardiac activity data, from the set of electric potential data for each time interval from the plurality of time intervals, and calculating the series of activation wavefront locations for the time interval based on the dipole densities.

In various embodiments, the method further comprises calculating a discrete set of cardiac activity data from the electric potential data for each time interval from the plurality of time intervals, without aggregating cardiac activity data or electric potential data from previous time intervals.

In various embodiments, each time interval is less than or equal to one cardiac cycle.

In various embodiments, each time interval is about 10 ms or less.

In various embodiments, each time interval is about 1 ms or less.

In various embodiments, each time interval is 0.3 ms±0.05 ms.

In various embodiments, the method further comprises recording the sets of electric potential data for the plurality of time intervals for at least about 100 ms.

In various embodiments, the method further comprises recording the sets of electric potential data for the plurality of time intervals for up to about 5 seconds.

In various embodiments, the method further comprises representing the surfaces of the one or more cardiac chambers as a plurality of nodes and representing the activation wavefront locations as nodes determined to have an activated state based on the sets of cardiac activity data.

In various embodiments, the number of nodes is at least about 3,000 nodes.

In various embodiments, the number of nodes is not more than about 10,000 nodes.

In various embodiments, the method further comprises representing the propagation of the activation wavefront locations on the graphical representation of surfaces of the one or more cardiac chambers as an activated state moving from node to node over at least a portion of the graphical representation of surfaces of the one or more cardiac chambers.

In various embodiments, the method further comprises calculating, for each time interval, a discrete set of cardiac activity data for the plurality of nodes.

In various embodiments, the method further comprises determining, for each time interval, one of a plurality of activation states of one or more nodes from the plurality of nodes based on the set of cardiac activation data calculated for the time interval, wherein the plurality of activation states includes an activated state and at least one other state.

In various embodiments, the method further comprises determining, for each time interval, an activation state from the plurality of activation states for each node in the plurality of nodes for the time interval.

In various embodiments, the method further comprises determining the activation state for each of the one or more nodes with reference to a threshold value.

In various embodiments, the threshold value is the same for each node in a time interval.

In various embodiments, the threshold value is different for two or more nodes in a time interval.

In various embodiments, the threshold value is a non-dynamic value that does not change from time interval to time interval.

In various embodiments, the method further comprises setting the non-dynamic value as a percentage of a max range relative to a zero value for the cardiac activity data.

In various embodiments, the threshold value is a dynamic threshold value independently calculated for different nodes or groups of nodes.

In various embodiments, the dynamic threshold value is a time-dependent dynamic threshold value and independently calculating the threshold value includes performing analysis of or mathematical operation on one or more cardiac activation parameters taken from a group consisting of: voltage biopotential, surface charge density, dipole density, or a combination of two or more thereof.

In various embodiments, the threshold value is a dynamic value and the method comprises adjusting the dynamic value for at least some of the one or more nodes across two or more time intervals.

In various embodiments, the method further comprises adjusting the dynamic value to account for temporal, spatial, global, regional, and/or local differences at different points in time of the one or more cardiac chambers.

In various embodiments, the method further comprises determining the cardiac activity data for a node in each time interval using cardiac activity data from neighboring nodes in the same time interval to smooth the graphical representation of the propagation of the activation wavefront locations.

In various embodiments, the method further comprises determining the cardiac activity data for the node by taking a time derivative of the cardiac activity data of the neighboring nodes.

In various embodiments, the method further comprises determining the cardiac activity data at the node using Coulombian averaging with the neighboring nodes.

In various embodiments, the method further comprises calculating the cardiac activity data as the Coulombian of surface charge density, and the user interface module is configured to display the Coulombian of the surface charge density.

In various embodiments, the method further comprises calculating the cardiac activity data as the Coulombian of surface dipole density and the user interface module is configured to display the Coulombian of the surface dipole density.

In various embodiments, the method further comprises calculating the cardiac activity data as the Coulombian of the surface voltage and the user interface module is configured to display the Coulombian of the surface voltage.

In various embodiments, the method further comprises using 2nd neighboring nodes to determine the cardiac activity data for the node.

In various embodiments, the method further comprises also using 3rd neighboring nodes to determine the cardiac activity data for the node.

In various embodiments, the method further comprises using more than 3rd neighboring nodes to determine the cardiac activity data for the node.

In various embodiments, the signal processor is configured to smooth the activation wavefront using a smoothing filter and/or a noise reduction filter, wherein the smoothing filter and/or a noise reduction filter is a median filter or other nonlinear filter used to remove noise from a node based set of data.

In various embodiments, the signal processor is configured to replace the value at each node with a median value of the node along with its neighbor nodes.

In various embodiments, the number of neighbor nodes is user defined, pre-determined, and/or a time varying value.

In various embodiments, the method further comprises determining the activation wavefront by taking a weighted spatial derivative of the cardiac activity at each node.

In various embodiments, the weighting comprises uniform weighting.

In various embodiments, the weighting comprises distance-based weighting.

In various embodiments, the method further comprises: defining a plurality of node activation states, including the activated state; defining an activation display scale as a set of time increments measured from a reference time, wherein each time increment is associated with a different node activation state; and associating, based on the cardiac activity data and the activation display scale, one of the plurality of node activation states with one or more nodes from the plurality of nodes relative to the reference time.

In various embodiments, the activation states include the activated state and one or more recently activated states.

In various embodiments, the one or more recently activated states is a plurality of recently activated states.

In various embodiments, the activated state and each recently activated state is associated with a different time increment of the activation display scale.

In various embodiments, the method further comprises associating one of a plurality of graphical indicia with each activation state.

In various embodiments, the plurality of graphical indicia includes one or more of different colors, different hues, different lines, different line patterns, different sizes or forms of dots or stippling, different opacities, and/or different textures.

In various embodiments, the method further comprises displaying the plurality of graphical indicia as a graphical key in conjunction with the graphical representation of the propagation of the activation wavefront.

In various embodiments, the method further comprises displaying each image in the series of images to include the plurality of graphical indicia selectively associated with one or more of the plurality of nodes, including associating a graphical indicia with a node as a function of an activation state of the node.

In various embodiments, the method further comprises displaying each image in the series of images to include a color from a plurality of colors selectively associated with each one or more of the plurality of nodes, wherein each color represents a different activation state, including associating the color with a node as a function of an activation state of the node.

In various embodiments, the method further comprises color coding each node as a function of an activation state associated with the node, wherein each activation state is represented by a different color, hue, and/or opacity.

In various embodiments, the method further comprises presenting at least one user input device that enables a user to select the activation display scale.

In various embodiments, the method further comprises displaying at least a portion of the sets of cardiac activity data in conjunction with the graphical representation of the propagation of the activation wavefront.

In various embodiments, the method further comprises displaying the at least a portion of the sets of cardiac activity data in the form of an ECG or EKG and/or EGM.

In various embodiments, the method further comprises displaying the time window in conjunction with the at least a portion of the sets of cardiac activity data.

In various embodiments, the method further comprises displaying the time window as an image moving relative to and/or over the ECG or EKG and/or EGM in synchronization with the graphical representation of the propagation of the activation wavefront.

In various embodiments, the method further comprises displaying the time window image as a semitransparent window superimposed over at least a portion of the ECG or EKG and/or EGM.

In various embodiments, the method further comprises presenting at least one user input device that enables a user to select a width of the time window.

In various embodiments, the method further comprises presenting at least one user input device that enables a user to adjust features of the graphical representation of the propagation of the activation wavefront on the graphical representation of the surfaces of the one or more cardiac chambers.

In various embodiments, the method further comprises providing a user input device that enables a user to rotate and/or scale the graphical representation of the one or more cardiac chambers.

In various embodiments, the method further comprises providing a user input device that enables a user to a user input to pause, rewind, and play the series of images within the time window.

In various embodiments, the method further comprises providing a user input device that enables a user to adjust the display speed of the series of images within the time window.

In various embodiments, the method further comprises displaying an origin of activation on the graphical representation of surfaces of the one or more cardiac chambers.

In various embodiments, the graphical representation of the propagation of the activation wavefront locations in the graphical representation of surfaces of the one or more cardiac chambers represents one or more of: regions of frequent activation representing major pathways; maximum local delay time as an approximation for conduction delay; max/min/threshold conduction velocity; minimum local reactivation period as an approximation of minimum refractory period; harmonic organization index as a degree of spectral energy at specific frequencies and its harmonics; peak negative signal; peak-to-peak amplitude; continuous trajectory, including continuous lines following the directional pattern of the wave front, with highlighting of areas of congestion and convergence; directional dispersion as a variance in direction of propagation; and/or angular velocity.

In accordance with aspects of the inventive concept, provided is a cardiac information dynamic display system, having a cardiac information console, comprising: a single processor and a user interface module. The signal processor is configured to: represent one or more cardiac chambers with a plurality of nodes; determine cardiac activity data associated with the plurality of nodes from biopotential data recorded from the one or more cardiac chambers for a plurality of time intervals; and determine activated nodes from among the plurality of nodes for each of the time intervals. The user interface module is configured to display the activated nodes as an activation wavefront propagating over a graphical representation of surfaces of the one or more cardiac chambers, wherein the graphical representation of the propagation of the activation wavefront locations is based on a time window.

In accordance with aspects of the inventive concept, provided is a cardiac information dynamic display method, comprising: representing one or more cardiac chambers with a plurality of nodes; determining cardiac activity data associated with the plurality of nodes from biopotential data recorded from the one or more cardiac chambers for a plurality of time intervals; determining activated nodes from among the plurality of nodes for each of the time intervals; and displaying the activated nodes as an activation wavefront propagating over a graphical representation of surfaces of the one or more cardiac chambers, wherein the graphical representation of the propagation of the activation wavefront locations is based on a time window.

In accordance with aspects of the inventive concept, provided is a cardiac information dynamic display system as shown and/or described.

In accordance with aspects of the inventive concept, provided is a cardiac information dynamic display system as shown and/or described.

DETAILED DESCRIPTION

Figure 1:
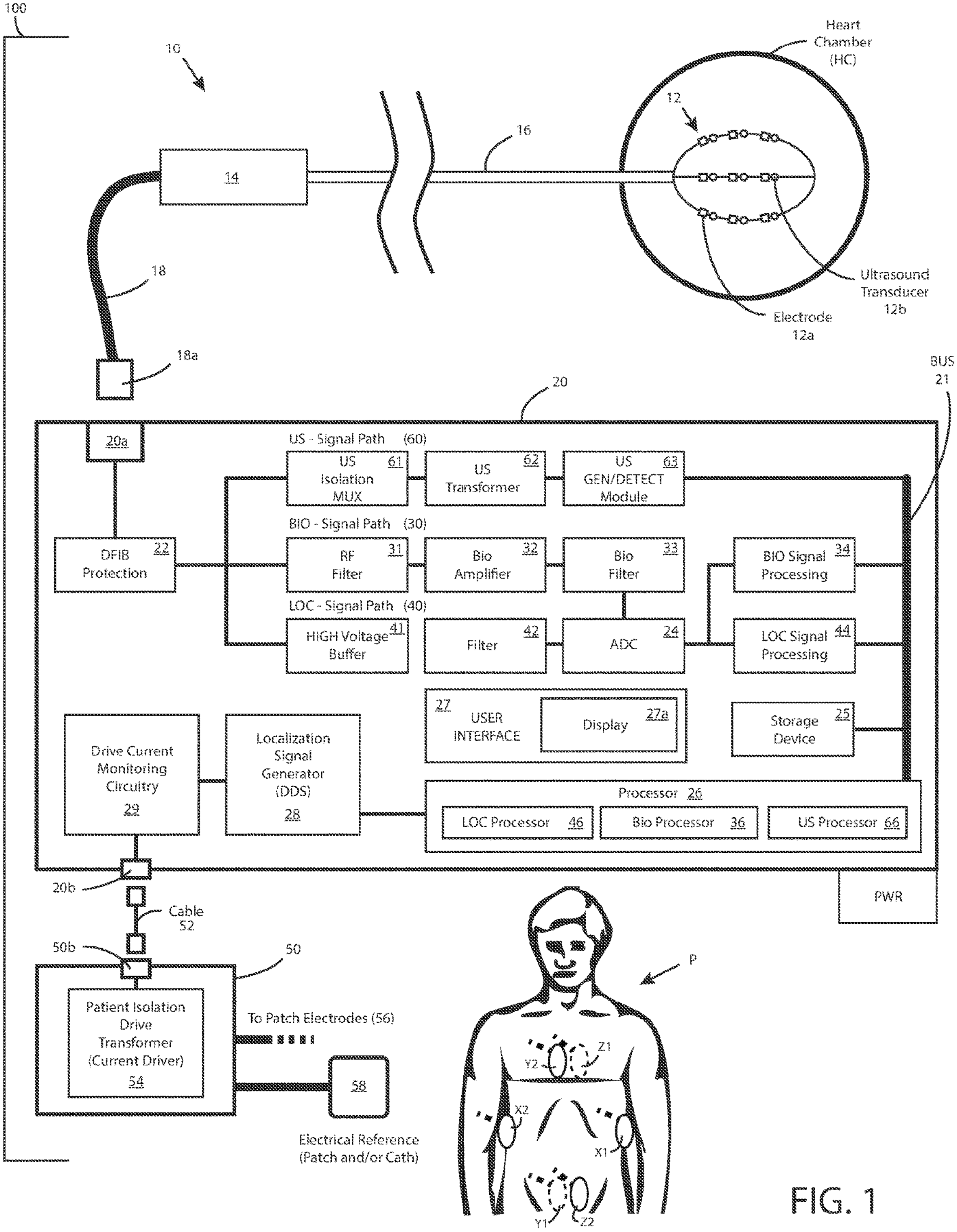
FIG. 1 provides a block diagram of an embodiment of a cardiac information processing system, in accordance with aspects of the inventive concept.

Various exemplary embodiments will be described more fully hereinafter with reference to the accompanying drawings, in which some exemplary embodiments are shown. The present inventive concept can, however, be embodied in many different forms and should not be construed as limited to the exemplary embodiments set forth herein.

It will be understood that, although the terms first, second, etc. are used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items. And a "combination" of associated listed items need not include all of the items listed, but can include all of the items listed.

It will be understood that when an element is referred to as being "on" or "attached", "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like can be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

Localization describes the process of establishing a coordinate system, and using one or more signals, such as electronic signals, to determine the position of one or more objects within that system. In some embodiments, the process of localization incorporates one or more signals generated from one or more sources that change as a function of space and/or time and a sensor, detector, or other transducer that measures the generated signal from a location. The location of the sensor can be on the object being localized or can be separate from the object being localized. Analysis of and/or calculation on the measured signal can be used to determine a positional relationship of the sensor and/or the object to the one or more sources of the generated signal. The method of localization can incorporate two or more generated signals to increase the number or accuracy of positional relationships between the sensor and the source. The source, sensor, and/or object can be co-located or can be the same device. In some embodiments, the change as a function of time and/or space includes the interaction of the generated signal with the measurement environment. In other embodiments, the process of localization measures an intrinsic or existing property or characteristic of the object, sensor, or environment, such as measuring a signal from an accelerometer positioned on the object or sensor.

Various exemplary embodiments are described herein with reference illustrations of idealized or representative structures and intermediate structures. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

To the extent that functional features, operations, and/or steps are described herein, or otherwise understood to be included within various embodiments of the inventive concept, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

Referring now to FIG. 1, provided is a block diagram of an embodiment of a cardiac information processing system 100, in accordance with aspects of the inventive concept. The cardiac information processing system 100 can be or include a system configured to perform cardiac mapping, diagnosis, and/or treatment, such as for treating abnormalities such as arrhythmia. Additionally or alternatively, the system can be a system configured for teaching and/or validating devices and methods of diagnosing and/or treating cardiac abnormalities or disease of a patient P. The system can further be used for generating displays of cardiac activity, such as dynamic displays of active wave fronts propagating across surfaces of the heart.

The cardiac information processing system 100 includes a catheter 10, a cardiac information console 20, and a patient interface module 50 that can be configured to cooperate to accomplish the various functions of the cardiac information processing system 100. The cardiac information processing system 100 can include a single power supply (PWR), which can be shared by the cardiac information console 20 and the patient interface module 50. Use of a single power supply in this way can greatly reduce the chance for leakage currents to propagate, such as to propagate into the patient interface module 50 and cause errors in localization, i.e., the process of determining the location of one or more electrodes within the body of patient P.

The catheter 10 includes an electrode array 12 that can be percutaneously delivered to a heart chamber (HC). In this embodiment, the array of electrodes 12 has a known spatial configuration in three-dimensional (3D) space. For example, in an expanded state the physical relationship of the electrode array 12 can be known or reliably assumed. Diagnostic catheter 10 also includes a handle 14, and an elongate flexible shaft 16 extending from handle 14. Attached to a distal end of shaft 16 is the electrode array 12, such as a radially expandable and/or compactable assembly. In this embodiment, the electrode array 12 is shown as a basket array, but the electrode array could take other forms in other embodiments. In some embodiments, expandable electrode array 12 can be constructed and arranged as described in reference to applicant's International PCT Patent Application Serial Number PCT/US2013/057579, titled "System and Method for Diagnosing and Treating Heart Tissue," filed Aug. 30, 2013, and International PCT Patent Application Serial Number PCT/US2014/015261, titled "EXPANDABLE CATHETER ASSEMBLY WITH FLEXIBLE PRINTED CIRCUIT BOARD," filed Feb. 7, 2014, the content of which are incorporated herein by reference in their entirety. In other embodiments, expandable electrode array 12 can comprise a balloon, radially deployable arms, spiral array, and/or other expandable and compactible structure.

Shaft 16 and expandable electrode array 12 are constructed and arranged to be inserted into a body (e.g. an animal body or a human body, such as the body of Patient P), and advanced through a body vessel, such as a femoral vein or other blood vessel. Shaft 16 and electrode array 12 can be constructed and arranged to be inserted through an introducer (not shown), such as when electrode array 12 is in a compacted state, and slidingly advanced through a lumen of a shaft 16 into a body space, such as a chamber of the heart (HC), such as the right atrium or the left atrium, as examples.

Expandable electrode array 12 can comprise multiple splines, each spline having a plurality of biopotential electrodes **12*a* and/or a plurality of ultrasound transducers 12*b*. Three splines are visible in FIG. 1, but the basket array is not limited to three splines, more or less splines can be included in the basket array. Each electrode 12*a* can be configured to record a biopotential (or voltage), such as the voltage determined, e.g., measured or sensed, at a point on a surface of the heart or at a location within a heart chamber HC. Each US transducer 12*b*** can be configured to transmit an ultrasound signal and receive ultrasound reflections to determine the range to a reflecting target, e.g., a point on the surface of a heart chamber (HC), used in the digital model creation of the anatomy.

As a non-limiting example, the three electrodes **12*a* and three US transducers 12*b* are shown on each spline in this embodiment. However, in other embodiments, the basket array can include more or less electrodes and/or more or less US transducers. Furthermore, the electrodes 12*a* and transducers 12*b* are arranged in pairs. Here, one electrode 12*a* is paired with one transducer 12*b*, with multiple electrode-transducer pairs per spline. The inventive concept is not, however, limited to this particular electrode-transducer arrangement. In other embodiments, not all electrodes and transducers need to be arranged in pairs, some could be arranged in pairs while others are not arranged in pairs. Also, in some embodiments, not all splines need to have the same arrangement of electrodes 12*a* and transducers 12*b*. Additionally, in some embodiments, electrodes 12*a* could be arranged on some splines, while transducers 12*b*** could be arranged on other splines.

Catheter 10 can comprise a cable or other conduit, such as cable 18, configured to electrically, optically, and/or electro-optically connect catheter 10 to the cardiac information console 20 via connectors **18*a* and 20*a*, respectively. In some embodiments, cable 18** comprises a mechanism selected from the group consisting of: a cable such as a steering cable; a mechanical linkage; a hydraulic tube; a pneumatic tube; and combinations of one or more of these.

The patient interface module 50 can be configured to electrically isolate one or more components of the cardiac information console 20 from patient P (e.g., to prevent undesired delivery of a shock or other undesired electrical energy to patient P). The patient interface module 50 can be integral with cardiac information console 20 and/or it can comprise a separate discrete component (e.g. separate housing), as is shown. The cardiac information console 20 comprises one or more connectors **20*b*, each comprising a jack, plug, terminal, port, or other custom or standard electrical, optical, and/or mechanical connector. Similarly, the patient interface module 50 includes one or more connectors 50*b*. At least one cable 52 connects the patient interface module 50 with the cardiac information console 20, via connectors 20*b* and 50*b***.

In this embodiment, the patient interface module 50 includes an isolated localization drive system 54, a set of patch electrodes 56, and one or more reference electrodes 58. The isolated localization drive system 54 isolates localization signals from the rest of system to prevent current leakage, for example current leakage caused by a low input impedance and/or a high capacitance between the localization drive system 54 and the rest of system 100. Signal loss from current leakage could result in performance degradation, and minimizing signal loss prevents such degradation. The isolation of the localization drive system 54 can minimize drift in localization positions and maintain a high degree of isolation between axes. The localization drive system 54 can operate as a current, voltage, magnetic, acoustic, or other type of energy modality drive. The set of patch electrodes 56 and/or one or more reference electrodes 58 can consist of conductive electrodes, magnetic coils, acoustic transducers, and/or other type of transducer or sensor based on the energy modality employed by the localization drive system 54. Additionally, the isolated localization drive system 54 maintains simultaneous output on all axes, e.g., a localization signal is present on each axis electrode pair, while also increasing the effective sampling rate at each electrode position. In some embodiments, the localization sampling rate comprises a rate between 10 kHz and 20 MHz, such as a sampling rate of approximately 625 kHz.

In this embodiment, the set of patch electrodes 56 include three (3) pairs of patch electrodes: an "X" pair having two patch electrodes placed on opposite sides of the ribs (X1, X2); a "Y" pair having one patch electrode placed on the lower back (Y1) and one patch electrode placed on the upper chest (Y2); and a "Z" pair having one patch electrode placed on the upper back (Z1) and one patch electrode placed on the lower abdomen (Z2). The patch electrode 56 pairs can be placed on any orthogonal and/or non-orthogonal sets of axes. In the embodiment of FIG. 1, the placement of electrodes is shown on patient P, where electrodes on the back are shown in dashed lines. (See also FIG. 2)

Figure 2:
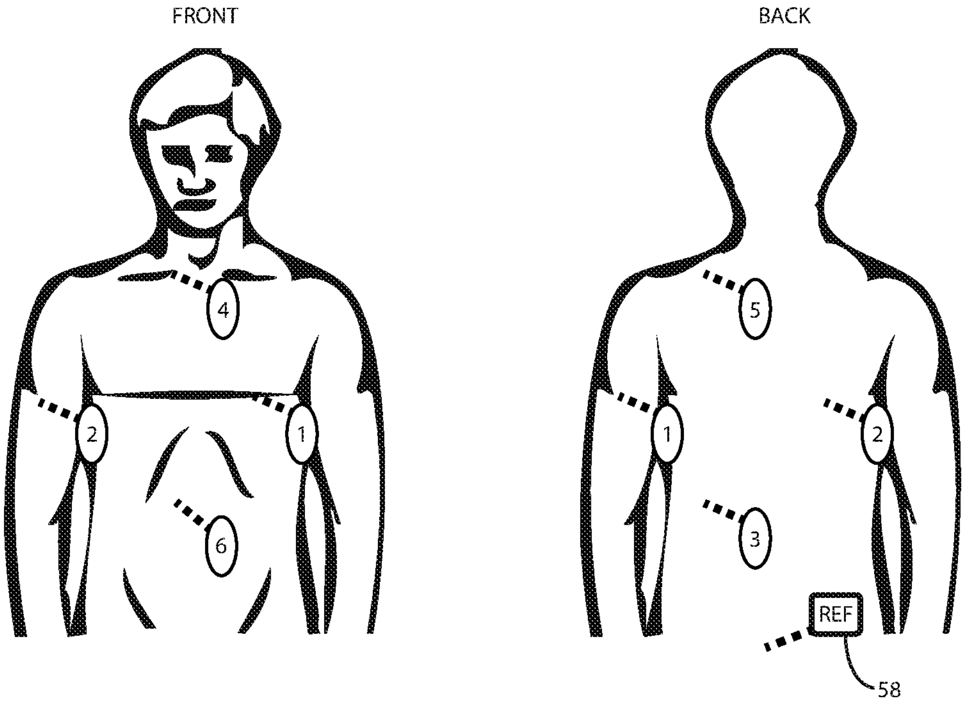
FIG. 2 is a drawing providing a front view and a back view of a patient and relative electrode placement, in accordance with aspects of the inventive concept.

FIG. 2 is a drawing providing a front view and a back view of a patient P and relative electrode placement, in accordance with aspects of the inventive concept. This figure demonstrates a preferred patch electrode placement, as discussed above. In FIG. 1, for example, the X electrodes X1 and X2 are shown as patch electrodes 1 and 2, respectively; the Z electrodes Z1 and Z2 are shown as patch electrodes 3 and 4, respectively; and the Y electrodes Y1 and Y2 are shown as patch electrodes 5 and 6, respectively. Thus, patches 1 and 2 are placed on the ribs, forming the X axis within the body; patches 3 and 4 are placed on the lower back and upper chest (respectively), forming the Z axis; and patches 5 and 6 are placed on the upper back and lower abdomen (torso), respectively, forming the Y axis. The three axes are of similar length, and not aligned with the "natural" axis of the body (i.e., head to toe, chest to back, and side to side).

The reference patch electrode 58 can be placed on the lower back and/or buttocks. Additionally, or alternatively, a reference catheter can be placed within a body vessel, such as a blood vessel in and/or proximate the lower back/buttocks.

The placement of electrodes 56 defines a coordinate system made up of three axes, one axis per pair of patch electrodes 56. In some embodiments, e.g., as shown in FIG. 2, the axes are non-orthogonal to a natural axis of the body, i.e., non-orthogonal to head-to-toe, chest-to-back, and side-to-side (i.e., rib-to-rib). The electrodes can be placed such that the axes intersect at an origin, such as an origin located in the heart. For instance, the origin of the three intersecting axes can be centered in an atrial volume. System 100 can be configured to provide an "electrical zero" that is positioned outside of the heart, such as by locating a reference electrode 58 such that the resultant electrical zero is outside of the heart (e.g. to avoid crossing from a positive voltage to a negative voltage at a one or more locations being localized).

As described hereabove, a patch pair can operate differentially, i.e. neither patch 56 in a pair operates as a reference electrode, and are both driven by system 100 to generate the electrical field between the two. Alternatively or additionally, one or more of the patch electrodes 56 can serve as the reference electrode 58, such that they operate in a single ended mode. One of any pair of patch electrodes 56 can serve as the reference electrode 58 for that patch pair, forming a single-ended patch pair. One or more patch pairs can be configured to be independently single-ended. One or more of the patch pairs can share a patch as a single-ended reference or can have the reference patches of more than one patch pair electrically connected.

Through processing performed by the cardiac information console 20, the axes can be transformed, e.g., rotated, from a first orientation, e.g., a non-physiological orientation based on the placement of electrodes 56, to a second orientation. The second orientation can comprise a standard Left-Posterior-Superior (LPS) anatomical orientation, i.e., the "x" axis is oriented from right to left of the patient, the "y" axis is oriented from the anterior to posterior of the patient, and the "z" axis is oriented from caudal to cranial of the patient. Placement of patch electrodes 56 and the non-standard axes defined thereby can be selected to provide improved spatial resolution when compared to patch electrode placement resulting in a normal physiological orientation of the resulting axes, e.g. due to preferred tissue characteristics between electrodes 56 in the non-standard orientation. For example, non-standard electrode placement can result in diminished influence of the low-impedance volume of the lungs on the localization field. Furthermore, electrode placement can be selected to create axes which pass through the body of the patient along paths of similar or equivalent lengths. Axes of similar length will possess more similar energy density per unit distance within the body, yielding a more uniform spatial resolution along such axes. Transforming the non-standard axes into a standard orientation can provide a more straightforward display environment for the user. Once the desired rotation is achieved, each axis can be scaled, i.e., made longer or shorter, as needed. The rotation and scaling are performed based on comparing pre-determined, e.g., expected or known, electrode array 12 shape and relative dimensions, with measured values that correspond to the shape and relative dimensions of the electrode array in the patch electrode established coordinate system. For example, rotation and scaling can be performed to transform a relatively inaccurate, e.g., uncalibrated, representation into a more accurate representation. Shaping and scaling the representation of the electrode array 12 can adjust, align, and/or otherwise improve the orientation and relative sizes of the axes for far more accurate localization.

The reference electrode(s) 58 can be or include a patch electrode and/or an electrical reference catheter, as a patient reference. A reference electrode 58 can be placed on the skin, and will act as a return for current for defibrillation. An electrical reference catheter can include a unipolar reference electrode used to enable common mode rejection. The unipolar reference electrode, or other electrodes on a reference catheter, can be used to measure, track, correct, or calibrate environmental, physiological, mechanical, electrical, or computational artifacts in a cardiac signal. In some embodiments, these artifacts may be due to respiration, cardiac motion, electrical noise from lab equipment, or artifacts induced by applied signal processing, such as filters. Another form of electrical reference catheter can be an internal analog reference electrode, which can act as a low noise "analog ground" for all internal catheter electrodes. Each of these types of reference electrodes can be placed in relatively similar locations, such as an electrode positioned on a catheter placed in an internal vessel (e.g. a vessel proximate the lower back and/or the apex of the heart) and/or a patch electrode placed on the lower back (as a patch). In some embodiments, system 100 comprises a reference catheter 58 including a fixation mechanism (e.g. a user activated fixation mechanism), which can be constructed and arranged to reduce displacement (e.g. accidental or otherwise unintended movement) of one or more electrodes of the reference catheter 58. The fixation mechanism can comprise a mechanism selected from the group consisting of: spiral expander; spherical expander; circumferential expander; axially actuated expander; rotationally actuated expander; and combinations of two or more of these.

In FIG. 1, aspects of the receiver components of the cardiac information console 20 are depicted. The cardiac information console 20 includes a defibrillation protection module 22 connected to connector 20*a*, which is configured to receive cardiac information from the catheter 10. The DFIB protection module 22 is configured to have a precise clamping voltage and a minimum capacitance. Functionally, the DFIB protection module 22 acts a surge protector, configured to protect the circuitry of console 20 during application of high energy to the patient, such as during defibrillation.

The DFIB protection module 22 is coupled to three signal paths, a biopotential (BIO) signal path 30, a localization (LOC) signal path 40, and an ultrasound (US) signal path 60. Generally, the BIO signal path 30 filters noise and preserves the measured biopotential data, and also enables the biopotential signals to be read while ablating, which is not the case in other systems. Generally, the LOC signal path 40 allows high voltage inputs, while filtering noise from received localization data. Generally, the US signal path 60 acquires range data from the physical structure of the anatomy using the ultrasound transducers 12*b* for generation of a 2D or 3D digital model of the heart chamber HC, which can be stored in memory.

The BIO signal path 30 includes an RF filter 31 coupled to the DFIB protection module 22. In this embodiment, the RF filter 31 operates as a low-pass filter having a high input impedance. The high input impedance is preferred in this embodiment because it minimizes the loss of voltage from the source, e.g., catheter 10, thereby better preserving the received signals, e.g., during RF ablation. The RF filter 31 is configured to allow biopotential signals from the electrodes 12*a* on catheter 10 to pass through RF filter 31, e.g., frequencies less than 500 Hz, such as frequencies in the range of 0.5 Hz to 500 Hz. However, high frequencies, such as high voltage signals used in RF ablation, are filtered out from the biopotential signal path 30. RF filter 31 can comprise a corner frequency between 10 kHz and 50 kHz, in some embodiments.

A BIO amplifier 32 is preferably a low noise single-ended input amplifier that amplifies the RF filtered signal. A BIO filter 33 filters noise out of the amplified signal. BIO filter 33 can comprise an approximately 3 kHz filter. In some embodiments, BIO filter 33 comprises an approximately 7.5 kHz filter, such as when system 100 is configured to accommodate pacing of the heart (e.g. avoid significant signal loss and/or degradation during pacing of the heart).

BIO filter 33 can include differential amplifier stages used to remove common mode power line signals from the biopotential data. This differential amplifier can implement a baseline restore function which removes DC offsets and/or low frequency artifacts from the biopotential signals. In some embodiments, this baseline restore function comprises a programmable filter which can comprise one or more filter stages. In some embodiments the filter can include a state dependent filter. Characteristics of the state dependent filter can be based on threshold and/or voltage with the filter rate varied based on filter state. Components of the baseline restore function can incorporate noise reduction techniques such as dithering or pulse width modulation of the baseline restore voltage. The baseline restore function may also determine by measurement, feedback, and/or characterization the filter response of one or more stages. The baseline restore function may also determine and/or discriminate the portions of the signal representing a physiological signal morphology from an artifact of the filter response and computationally restore the original morphology, or portion thereof. In some embodiments, the restoration of the original morphology can include subtraction of the filter response directly or after additional signal processing of the filter response, e.g., static, temporally-dependent, and/or spatially-dependent weighting, multiplication, filtering, inversion, and combinations of these. In some embodiments, the baseline restore function can be implemented in BIO filter 33, BIO processor 36, or both.

The LOC signal path 40 includes a high voltage buffer 41 coupled to the DFIB protection module 22. In this embodiment, the high voltage buffer 41 is configured to accommodate the relatively high voltages used in treatment techniques, such as RF ablation voltages. For example, the high voltage buffer can have ±100V power-supply rails. The high voltage buffer 41 also has a high input impedance, such as when the high voltage buffer 41 does not include a pre-filter stage, and has good performance at high frequencies. A high frequency bandpass filter 42 is coupled to the high voltage buffer 41, and has a passband frequency range of about 20 kHz to 80 kHz for use in localization. Preferably, the filter 42 has low noise with unity gain, e.g., a gain of 1 or about 1.

The US signal path 60 comprises an US isolation multiplexer, MUX 61, a US transformer with a Tx/Rx switch, US transformer 62, a US generation and detection module 63, and an US signal processor 66. The US isolation MUX 61 is connected to the DFIB protection module 22, and is used for turning on/off the US transducers 12*b*, such as in a predetermined order or pattern. The US isolation MUX 61 can be a set of high input impedance switches that, when open, isolate the US system and remaining US signal path elements, decoupling the impedance to ground (through the transducers and the US signal path 60) from the input of the LOC and BIO paths. The US isolation MUX 61 also multiplexes one transmit/receive circuit to one or more multiple transducers 12*b* on the catheter 10. The US transformer 62 operates in both directions between the US isolation MUX 61 and the US generation and detection module 63. US transformer 62 isolates the patient from the current generated by the US transmit and receive circuitry in module 63 during ultrasound transmission and receiving by the US transducers 12*b*. The switches of US transformer 62 selectively engage the transmit and/or receive electronics of module 63 based on the mode of operation of the transducers 12*b*, such as to activate one or more of the associated transducers 12*b*, such as in a predetermined order or pattern. That is, in a transmit mode, the module 63 receives a control signal from a US processor 66 (within a data processor 26) that activates the US signal generation and connects an output of the Tx amplifier to US transformer 62. The US transformer 62 couples the signal to the US isolation MUX 61 which selectively activates the US transducers 12*b*. In a receive mode, the US isolation MUX 61 receives reflection signals from one or more of the transducers 12*b*, which are passed to the US transformer 62. The US transformer 62 couples signals into receive electronics of the US generation and detection module 63, which in-turn transfers reflection data signals to the US processor 66 for processing and use by the user interface system 27 and display 27*a*.

An AD (analog-to-digital) converter ADC 24 is coupled to the BIO filter 33 of the BIO signal path 30 and to the high frequency filter 42 of the LOC signal path 40. Received by the ADC 24 is a set of individual time-varying analog biopotential voltage signals, one for each electrode 12*a*. These biopotential signals have been differentially referenced to a unipolar electrode for enhanced common mode rejection, filtered, and gain-calibrated on an individual channel-by-channel basis, via BIO signal path 30. Received by the ADC is also a set of individual time-varying analog localization voltage signals for each axis of each patch electrode 56, via LOC signal path 40, which are output to the ADC 24 as a collection of 48 (in this embodiment) localization voltages measured at a single time for the electrodes 12*a*. The ADC 24 has high oversampling to allow noise shaping and filtering, e.g., with an oversampling rate of about 625 kHz. In some embodiments, sampling is performed at or above the Nyquist frequency of system 100. The ADC 24 is a multi-channel circuit that can combine BIO and LOC signals or keep them separate. In one embodiment, as a multi-channel circuit, the ADC 24 can be configured to accommodate 48 localization electrodes 12*a* and 32 auxiliary electrodes (e.g., for ablation or other processes), for a total of 80 channels. In other embodiments, more or less channels can be provided. In FIG. 1, for example, almost all of the elements of the cardiac information console 20 can be duplicated for each channel, e.g., except for the UI system 27. For example, the cardiac information console 20 can include a separate ADC for each channel, or an 80 channel ADC. In this embodiment, signal information from the BIO signal path 30 and the LOC signal path 40 are input to and output from the various channels of the ADC 24. Outputs from the channels of the ADC 24 are coupled to either the BIO signal processing module 34 or the LOC signal processing module 44, which pre-process their respective signals for subsequent processing as described herein below. In each case, the preprocessing prepares the received signals for the processing by their respective dedicated processors discussed below. The BIO signal processing module 34 and the LOC signal processing module 44 can be implemented in firmware, in whole or in part, in some embodiments.

The biopotential signal processing module 34 can provide gain and offset adjustment and/or digital RF filtering having a non-dispersive low pass filter and an intermediate frequency band. The intermediate frequency band can eliminate ablation and localization signals. The biopotential signal processing module 34 can also include digital biopotential filtering, which can optimize the output sample rate.

Additionally, the biopotential signal processing module 34 can also include pace blanking, which is the blanking of received information during a time frame when, for example, a physician is "pacing" the heart. Temporary cardiac pacing can be implemented via the insertion or application of intracardiac, intraesophageal, or transcutaneous leads, as examples. The goal in temporary cardiac pacing is to interactively test or improve cardiac rhythm and/or hemodynamics until the underlying problem resolves or a permanent pacing strategy is applied. To accomplish the foregoing, active and passive pacing trigger and input algorithmic trigger determinations can be performed, e.g., by system 100. The algorithmic trigger determination can use subsets of channels, edge detection and/or pulse width detection to determine if pacing has occurred. Optionally, pace blanking may be applied on all channels or subsets of channels including channels on which detection did not occur.

Additionally, the biopotential signal processing module 34 can also include specialized filters that remove ultrasound signals and/or other unwanted signals, e.g., artifacts, from the biopotential data. In some embodiments, to perform this filtering, edge detection, threshold detection and/or timing correlations can be used.

The localization signal processing module 44 can provide individual channel/frequency gain calibration, IQ demodulation with tuned demodulation phase, synchronous and continuous demodulation (without MUXing), narrow band IIR filtering, and/or time filtering (e.g. interleaving, blanking, etc.), as discussed herein below. The localization signal processing module can also include digital localization filtering, which optimizes the output sample rate and/or frequency response.

In this embodiment, the algorithmic computations for the BIO signal path 30, LOC signal path 40, and US signal path 60 are done in the cardiac information console 20, including: processing multiple channels at one time, measuring propagation delays between channels, turning x, y, z data into a spatial distribution of electrode locations, including computing and applying corrections to the collection of positions, combining individual ultrasound distances with electrode locations to calculate detected endocardial surface points, and constructing a surface mesh from the surface points. The number of channels processed by the cardiac information console 20 can be between 1 and 500, such as between 24 and 256, such as 48, 80, or 96 channels.

A data processor 26, which may include one or more of a plurality of types of processing circuits (e.g., a microprocessor) and memory circuitry, executes computer instructions necessary to perform the processing of the pre-processed signals from the BIO signal processing module 34, localization signal processing module 44, and US TX/RX MUX 61. The data processor 26 can be configured to perform calculations, as well as perform data storage and retrieval, necessary to perform the functions of the cardiac information processing system 100. The US GEN/DETECT module 63, BIO signal processing module 34, LOC signal processing module 34, storage device 25, and the data processor 26 can be coupled together by one or more bus 21.

In this embodiment, data processor 26 includes a biopotential (BIO) processor 36, a localization (LOC) processor 46, and an ultrasound (US) processor 66. The biopotential processor 36 can perform processing of recorded, measured, or sensed biopotentials, e.g., from electrodes 12*a*. The LOC processor 46 can perform processing of localization signals. And the US processor 66 can perform image processing of the reflected US signals, e.g., from transducers 12*b*.

The biopotential processor 36 can be configured to perform various calculations. For example, the BIO processor 36 can include an enhanced common mode rejection filter, which can be bidirectional to minimize distortion and which may be seeded with a common mode signal. The BIO processor 36 can also include an optimized ultrasound rejection filter and be configured for selectable bandwidth filtering. Processing steps for data in signal path 60 can be performed by bio signal processor 34 and/or BIO processor 36.

The localization processor 46 can be configured to perform various calculations. As discussed in more detail below, the LOC processor 46 can electronically make (calculate) corrections to an axis based on the known shape of electrode array 12, make corrections to the scaling or skew of one or more axes based on the known shape of the electrode array 12, and perform "fitting" to align measured electrode positions with known possible configurations, which can be optimized with one or more constraints (e.g. physical constraints, such as distance between two electrodes 12*a* on a single spline, distance between two electrodes 12*a* on two different splines, maximum distance between two electrodes 12*a*, minimum distance between two electrodes 12*a*, and/or minimum and/or maximum curvature of a spine, and the like).

The US processor 66 can be configured to perform various calculations associated with generation of the US signal via the US transducers 12*b* and processing US signal reflections received by the US transducers 12*b*. The US processor 66, can be configured to interact with the US signal path 60 to selectively transmit and receive US signals to and from the US transducers 12*b*. The US transducers 12*b* can each be put in a transmit mode or a receive mode under control of the US processor 66. The US processor 66 can be configured to construct a 2D and/or 3D image of the heart chamber (HC) within which the electrode array 12 is disposed, using reflected US signals received from the US transducers 12*b* via the US path 60.

The cardiac information console 20 also includes localization driving circuitry, including a localization signal generator 28 and a localization drive current monitor circuit 29. The localization driving circuitry provides high frequency localization drive signals (e.g., 10 kHz-1 MHz, such as 10 kHz-100 kHz). Localization using drive signals at these high frequencies reduce the cellular response effect on the localization data, e.g., from blood cell deformation, and/or allow higher drive currents, e.g., to achieve a better signal-to-noise ratio. The signal generator 28 produces a high resolution digital synthesis of a drive signal, e.g., sine wave, with ultra-low phase noise timing. The drive current monitoring circuitry provides a high voltage, wide bandwidth current source, which is monitored to measure impedance of the patient P.

The cardiac information console can also include at least one data storage device 25, for storing various types of recorded, measured, sensed, and/or calculated information and data, as well as program code embodying functionality available from the cardiac information console 20.

The cardiac information console 20 can also include a user interface (UI) system 27 configured to output results of the localization, biopotential, and US processing. The UI system 27 can include at least one display 27*a* to graphically render such results in 2D, 3D, or a combination thereof.

Figure 3:
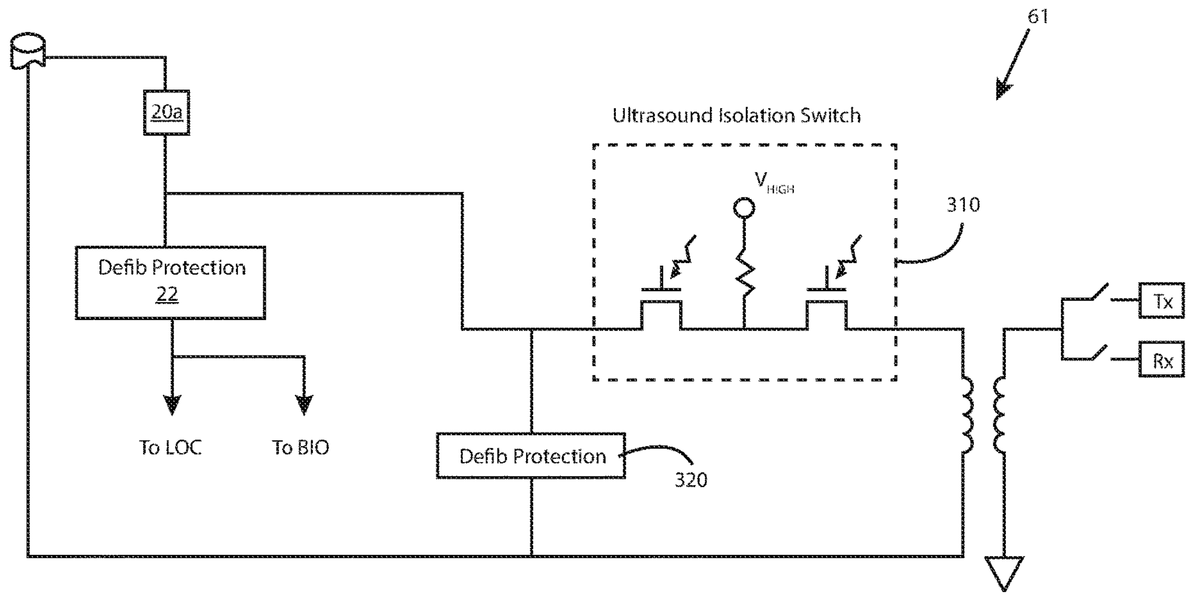
FIG. 3 is a schematic diagram of an ultrasound high input impedance switch, in accordance with aspects of the inventive concept.

FIG. 3 is a schematic diagram of an embodiment of ultrasound circuitry including an ultrasound high input impedance MUX 61, in accordance with aspects of the inventive concept. The ultrasound high input impedance MUX 61 includes ultrasound isolation switches 310 (single switch shown). Ultrasound isolation switch 310 connects in front of defibrillation (Defib) protection module 22 discussed above, and has a separate Defib protection circuit 320 which connects to a port to which the localization, mapping, and auxiliary catheters (e.g., an ablation catheter) are connected (see, e.g., connector 20*a* FIG. 1).

This approach provides isolation of ultrasound signals from the BIO and LOC signals. It is a minimum capacitance implementation, in which high voltage bias reduces capacitance and a symmetric switch minimizes charge injection. The high voltage also shortens the time for which the switch reaches an "on" state, and minimizes time of distortion for biopotential and localization signals. In one embodiment, OptoFETs isolate the control electronics from Defib protection circuit 320.

Figure 4:
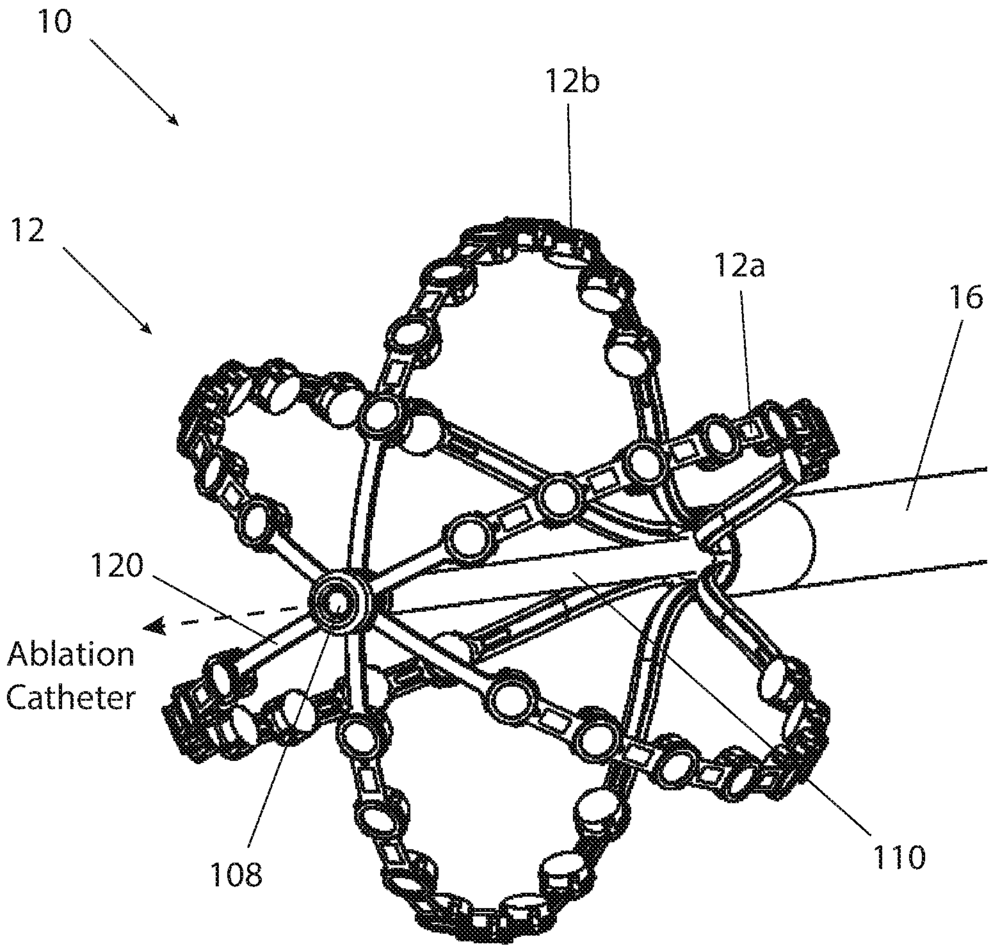
FIG. 4 provides a perspective view of an embodiment of a catheter of FIG. 1, in accordance with aspects of the inventive concept.

FIG. 4 is a perspective view of an embodiment of the electrode array 12 of FIG. 1, in accordance with aspects of the inventive concept. In the embodiment of FIG. 4, the electrode array 12 includes a plurality of splines 120, with the biopotential electrodes 12*a* and ultrasound transducers 12*b* coupled to, disposed on, or formed in the splines 120. For example, the ultrasound transducers 12*b* can be coupled to one or more splines 120 using a housing (not shown). However, in other embodiments, the ultrasound transducers 12*b* could be coupled to the splines 120 in different manners and/or different electronic elements could be included.

In this embodiment, an array of ultrasound transducers 12*b* and biopotential electrodes 12*a* are substantially equally distributed across a number of splines 120—shown in an expanded state. Proximal ends (nearest the shaft 16) of the splines 120 are attached to a distal end of the shaft 16, such as at a location on or within shaft 16, or between shaft 16 and an inner, translatable (i.e., advanceable and retractable) shaft 110. Distal ends of the splines 120 can be connected to distal end of inner shaft 110, which is retracted and advanced to expand and collapse, respectively, the electrode array 12. Inner shaft 110 can be advanced and retracted via a control on a proximal handle (not shown in FIG. 4). Inner shaft 110 can include a lumen 108.

The electrode array 12 includes ultrasound transducers 12*b* located in or on the splines of the electrode array 12. In this embodiment, a single electrode 12*a* (e.g., for localization) is paired with an ultrasound transducer 12*b* (e.g., for anatomical representation). In one embodiment, there are 48 of such pairs on the electrode array 12. In other embodiments, the system can also localize electrodes not paired with transducers, such as with an AUX catheter and/or a catheter with only electrodes on the array. The catheter 10 also connects to cardiac information console 20 as described in FIG. 1.

With respect to the multiple "pairs" of electrical components, for example, at least one pair comprises an electrode 12*a* and an ultrasound transducer 12*b*. Each electrode 12*a* can be configured to determine, record, measure, or sense a voltage (a biopotential voltage or a localization voltage), such as the voltage present on a surface of the heart or at a location within a heart chamber HC. Each ultrasound transducer 12*b* can be configured to send and/or receive ultrasound signals, such as to produce a digital model of the tissue, including at least a portion of the heart and/or other patient anatomical location. When such information is accumulated for multiple pairs 12*a*, 12*b*, a digital model of the heart with a superimposed map of cardiac activity can be produced for display via user interface 27.

In some embodiments, shaft 110 can comprise one or more conduits and/or passageways, such as lumen 108. Lumen 108 can be configured to allow for electrode array 12 to be inserted over a guidewire, such as when lumen 108 is sized to slidingly receive a guidewire, and lumen 108 continues to a proximal portion of catheter 10, such as when lumen 108 exits handle 14 of catheter 10. Additionally or alternatively, lumen 108 can be sized to slidingly receive one or more devices, such as a device selected from the group consisting of: an ablation catheter; a mapping catheter; a cryo-ablation catheter; a tip ablation catheter; a diagnostic catheter; and combinations of two or more of these. In some embodiments, lumen 108 can be configured to allow for the delivery of one or more drugs or other agents during a diagnostic or other procedure.

Figure 5:
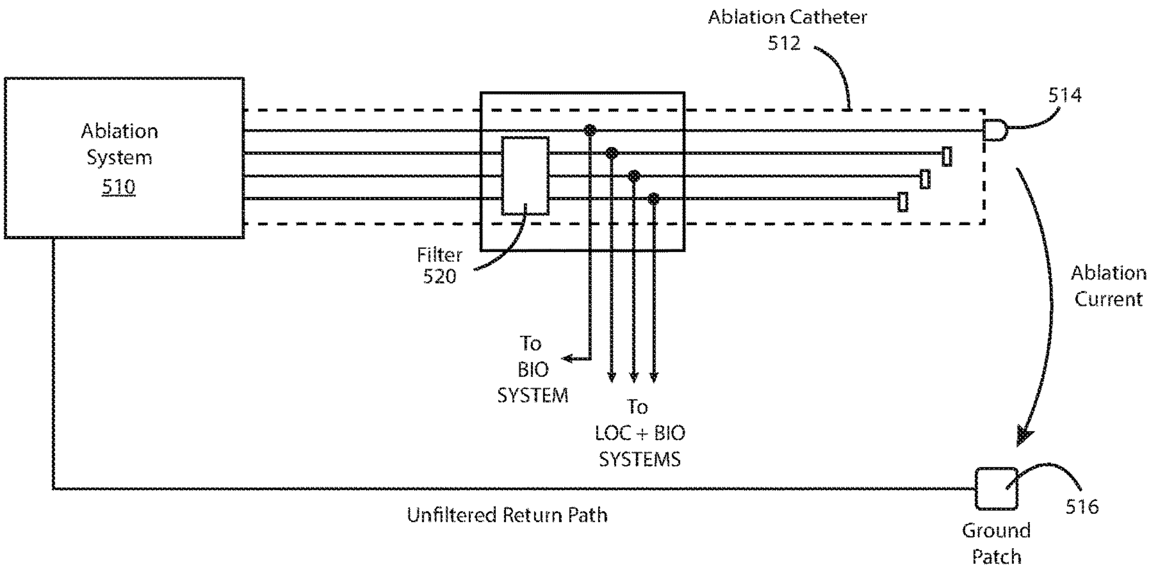
FIG. 5 is a schematic diagram of an ablation catheter, in accordance with aspects of the inventive concept.

FIG. 5 is a schematic diagram of an embodiment of an ablation system and an ablation catheter, in accordance with aspects of the inventive concept. There is an ablation system 510 coupled to an ablation catheter 512. An ablation tip 514 is located on a distal end of the ablation catheter 512. The ablation tip 514 delivers ablation energy to the tissue, e.g., RF ablation energy.

In this embodiment, there is no alteration to the "power path", e.g., no filtering of the power path, so no impedances are added to the chain and no ablation power is wasted in filters. There are filters 520 connected to non-ablation electrodes, e.g., electrodes used as part of a localization system. A high input impedance is maintained for the localization system, which allows localization during delivery of ablation energy. Additionally, in this embodiment, less ablation noise or artifact is coupled into the BIO and/or LOC signals than in the alternate configuration of a filter in the return path between the ablation system 510 and the ground patch 516.

Figure 6:
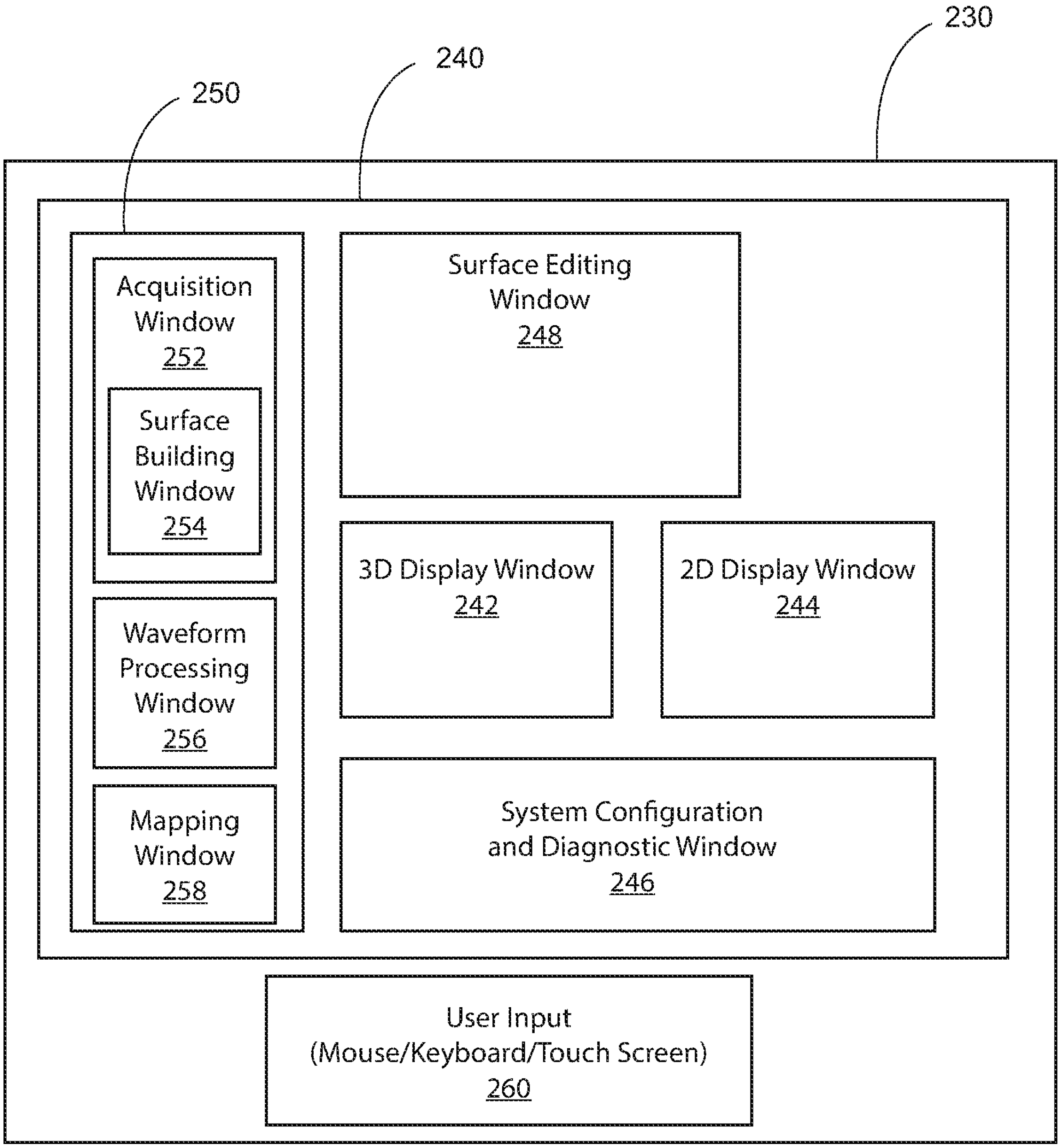
FIG. 6 provides a block diagram of an embodiment of a user interface system that can be used with a diagnostic catheter as described herein, for example, in accordance with the present inventive concept.

FIG. 6 provides a block diagram of an embodiment of a user interface (UI) system 230 that can be used with a diagnostic catheter as described herein, for example catheter 10, in accordance with the present inventive concepts. The user interface system 230 can be an embodiment of user interface system 27 of FIG. 1, or a portion thereof.

The UI system 230 includes a display area 240, which can include one or more windows, screens, and/or monitors on which information and graphics can be rendered/shown, e.g., as 2D or 3D displays. The windows in the display area 240 need not be arranged nor relatively sized as shown in FIG. 6. And not all windows shown in display area 240 must be included. The depiction in FIG. 6 represents an illustrative embodiment, but a UI system in accordance with the inventive concept is not limited to the particular embodiment shown.

A 3D display window 242 can be included to show graphical elements in a three-dimensional (3D) space, such as a heart or heart chamber. The images and information rendered in the 3D display window 242 can change based on the user task being performed, e.g., based on the task being done in a main application window 250. The 3D display window 242 can also exist within the main application window 250, in some embodiments. The 3D display window 242 can be user interactive, and can change in response to the user interaction therewith.

A two-dimensional (2D) display window 244 can be included to show graphical elements in a two-dimensional space. The images and information rendered in the 2D window 244 can change based on the user task being performed, e.g., based on the task being done in the main application window 250. The 2D display window 244 can also exist within the main application window 250, in some embodiments. The 2D display window 244 can be user interactive, and change in response to the user interaction therewith.

The main application window 250 can include a primary workflow interface to create 3D maps. An acquisition window 252 provides tools, e.g., user interface tools, necessary to view and record biopotential signals, localization signals, and/or ultrasound signals. One tool of the acquisition window 252 allows ultrasound and localization data to be combined to reconstruct a chamber anatomy (i.e. build a digital model of a surface that represents the chamber anatomy). This representation of the anatomy can be displayed in a surface building window 254. Additionally, previously reconstructed chamber anatomies (e.g. of the patient and/or a surrogate) can be loaded from one or more data repositories, such as files, databases, or memory and displayed in the surface building window 254 to be used with live data. Configuration settings are available from this window 254 to properly register/orient a chamber reconstruction to the live data.

A waveform processing window 256 can be provided and used to allow recorded and/or real-time data to be reviewed, filtered, and/or analyzed. The user can use these tools to identify a time segment of data to be mapped. Segments can be from 1 sample in length to a full recorded data length. Segment selection can also take the form of passing data directly, e.g., time sample by time sample, to a mapping algorithm, such that maps can be made "on the fly" (e.g. in real-time, near real-time, or pseudo real-time, "real-time" herein), without manual segment selection. In various embodiments, the waveforms being processed can be shown in the 2D display window 244, e.g., in the form of an electrogram (EGM) or electrocardiogram (ECG or EKG). In various embodiments, the 3D display window 242 can show any or all of the following: the voltage signals on the basket electrodes rendered onto a three-dimensional surface of the size and shape of the basket or representative size and shape of the basket; a colored topographic surface showing the electrode signals (color and "Z-height" of the topography corresponding to voltage amplitude), with electrodes oriented in relative neighbor relationship; the spatial position of the basket in relation to the reconstructed surface to show the basket position within the chamber of interest; the surface voltage across the surfaces of the anatomy; the surface source signal (charge density or dipole density) across surfaces of the anatomy; derived calculations or quantities arising from the surface source signal across surfaces of the anatomy; and/or a wave front of cardiac activity propagating across surfaces of the anatomy.

A mapping window 258 can be provided and used to allow configuration and execution of the mapping algorithms, including selection of a surface source model. The resulting 3D maps can be rendered in the 3D display window 242 with corresponding waveforms shown in the 2D display window 244. A time cursor or window can be included to provide a time index between both of the 2D and 3D display windows. The time cursor or window can be configured to slide or move across the waveforms in the 2D window in synch with a dynamically changing display rendered in the 3D window.

A system configuration and diagnostic window 246 can be provided and used to show live signals from the catheters (e.g., processed through electronics module 200)—biopotential, localization, and/or ultrasound, as examples. This window 246 can be used for verification of operation of such systems or subsystems.

A surface editing window 248 can be provided and used to allow the user to edit and process the reconstructed anatomy. Tools provided can include, but are not limited to: selection (individual vertices/polygons, rectangular, elliptical, free-form shape, automatic isolated component selection and/or sharp feature selection), trimming (through-cut, front-surface cut), smoothing, re-meshing, hole-filling, subdivision, and surface deformation, such as push-pull, tools.

These tools can include shape identification, component identification, isolation, extraction, appending and/or merging tools. These tools can be configured to operate manually, semi-automatically and/or automatically. These tools can comprise user interactive surface editing tools. In some embodiments, the user interactive surface editing tools may include the ability to generate additional elements to be merged with the surface. The generation can include one or more of the following: manual or algorithmic identification of a cross-section which is extended and/or extruded along an axis vector a defined distance; pushing and/or pulling or otherwise general deformation of the surface at a location and along one or more directions as determined by the user or an algorithm; attaching and/or connecting an adjacent structure; growing the original structure based on acquired data, such as ultrasound or localization data; and/or combinations of one or more of these.

A user input module 260 can include human interface devices, such as mouse, keyboard, touchscreen, digital pen, and/or other devices that can be used to provide user input to and/or control of the system and its renderings. In various embodiments, such user input devices can enable an operator/user to change the orientation of the anatomy in the 3D window, e.g., rotate, zoom in/out in the 2D and/or 3D windows, start, stop, pause, rewind, fast forward and/or replay videos or image sequences in the 2D and/or 3D window. In various embodiments, such user input devices can enable an operator/user to change the graphical parameters or characteristics of the 2D and/or 3D windows, such as color assignment, brightness, contrast and so on. In various embodiments, such user input devices can enable an operator/user to control parameters and/or characteristics of the dynamic display of node activation representing cardiac activity, such as activation window width and activation display step (see FIG. 9).

Figure 7:
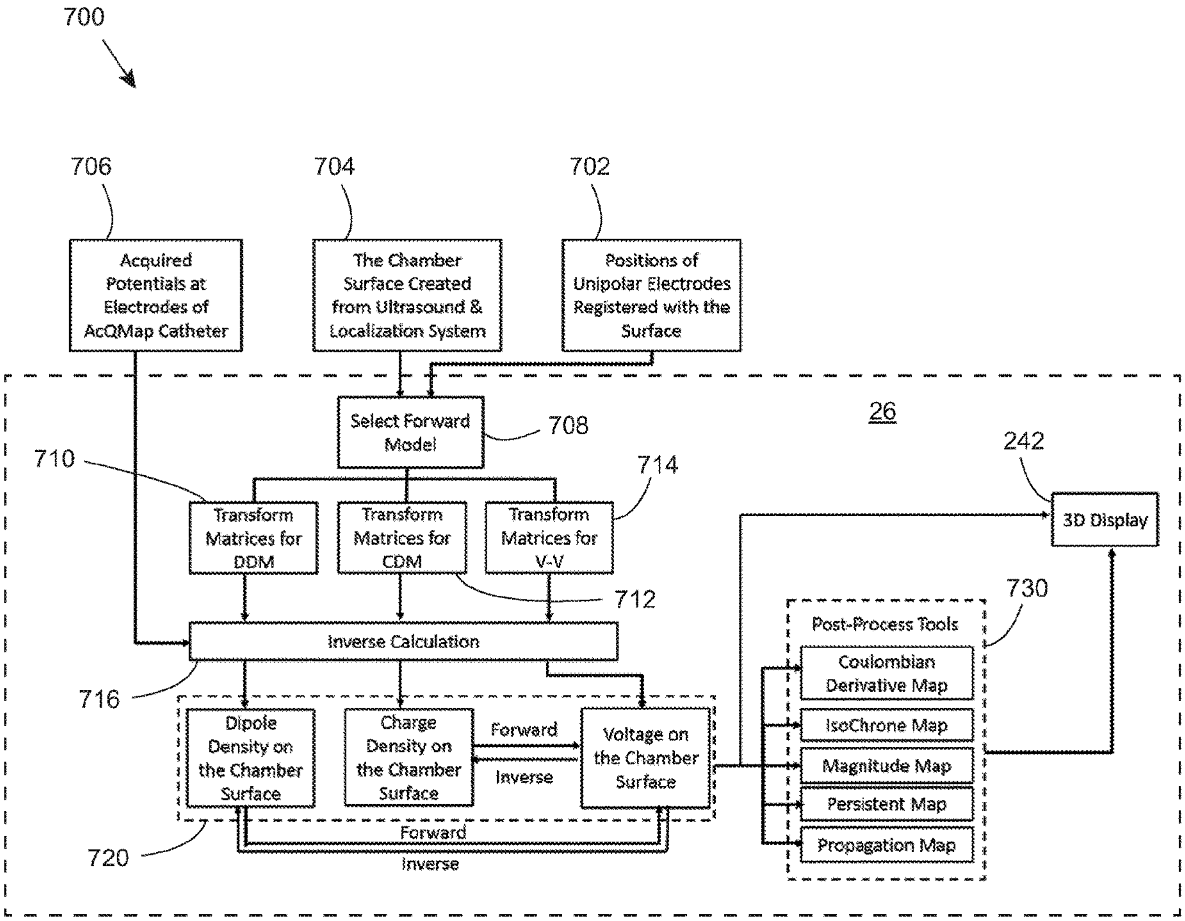
FIG. 7 provides a functional block diagram of an embodiment of a cardiac information processing system, in accordance with the present inventive concept.

FIG. 7 provides an embodiment of a functional block diagram of a cardiac information processing system 700, in accordance with aspects of the present inventive concept.

Using the system 700 of FIG. 7, a user can choose what to calculate and/or what to display, e.g., the user can display Dipole Density (DDM), Charge Density (CDM), and/or Voltage (V-V). This information is calculated based on information represented in the top three boxes 702, 704, 706, e.g., the position of the electrodes 702, the shape and location of the chamber (surface) 704, and the potentials recorded at the electrodes 706. The system 700 can also be configured to support and enable changes back and forth between the different display modes, and with post-processing tools, can change how that information is displayed.

The dashed box around portions of system 700 can represent a detailed portion of processor 26 of cardiac information console 20 of FIG. 1. The processing includes selecting a forward model 708. Based thereon, one or more of the following three operations can be performed: Dipole Density Mapping (DDM) 710, Charge Density Mapping (CDM) 712, and/or Voltage to Voltage Mapping (V-V) 714. In Dipole Density Mapping (DDM), electrical fields that could be measured by electrodes inside and/or outside of the heart chamber are generated from a distribution of dipole sources, having a magnitude and direction, on the surface of the heart chamber, organized and arranged as Dipole Densities (DD). In Charge Density Mapping (CDM), electrical fields that could be measured by electrodes inside or outside of the heart chamber are generated from a distribution of scalar charge sources, having a magnitude only, on the surface of the heart chamber, organized and arranged as Charge Densities (CD). And in Voltage-to-Voltage Mapping (V-V), no source assumption is made, and the voltages measured on electrodes inside or outside of the heart chamber are propagated from the voltages on the heart chamber surface (e.g. using Laplace's equation and/or other methods known to those skilled in electromagnetic field theory).

With the chamber surface and electrodes' positions registered with the surface as the inputs, the transform matrix, which encodes relationships between the DD/CDNoltages on the heart chamber to the measured voltages on electrodes, is the output of the forward calculation.

An Inverse Calculation 716 is performed, with the potentials acquired from the mapping catheter and the transform matrix (the output from the forward calculation) as the inputs, the DD/CDNoltages on the surface can be obtained by solving a linear system using a regularization method, for example the Tikhonov regularization method.

The DD/CD/Voltages on the surface, box 720, are outputs from the inverse calculation 716. The surface voltages can be forwardly computed from the derived surface DD/CD for DDM/CDM, and surface voltages from V-V can be used to derive the surface DD/CD using the transform matrix specified by the heart chamber surface.

In some embodiments, cardiac information processing system 700 comprises post-process tools 730. Using the same, DD/CD/Voltages can be post-processed to produce a Coulombian map (an adaptation of the discrete Laplacian, or spatial second derivative of the DDM, CDM and/or Voltage maps), Isochrone map (activation timings), Magnitude map (peak to peak magnitude or negative peak magnitude), Persistence map (active and resting status), Propagation map (e.g., a wavefront), spectral maps (e.g. dominant frequency maps), state-space maps, conduction velocity maps (both magnitude and direction of propagation) and/or phase-maps, as examples. In some embodiments, post-processing can include identification of patterns or characteristics of cardiac information for different regions. Regions can comprise an area of the surface as small as a single vertex (i.e. a node of the digital model of the anatomy) and as large as the entire chamber. For example, processing can include identification of patterns of propagation such as rotational patterns, radial expansion from a point, and/or multi-directional activation through a confined zone. In some embodiments, a quantitative index may be calculated using one or more of the post-processed data, for example an index of the complexity of the patterns otherwise called "dispersion", that incorporates the pattern of activation and the amplitude and frequency components of cardiac signals at different locations. In some embodiments, the post-process tools can include a quantitative and/or qualitative measure of consistency or lack of consistency over a duration of time for one or more post-processing outputs. The time duration may be over one or more orders of magnitude of time, such as: 1-500 msec (e.g. a single "cycle" of activation across a region or the whole chamber); 50 msec-5 sec (e.g. multiple cycles of activation or a single cardiac 'beat' across multiple heart chambers); 1 sec-30 sec (e.g. multiple cycles of activation or multiple cardiac beats); 30 sec-15 min (e.g. within a duration of one or more discrete therapeutic or interventional actions, such as a set of spot ablations or delivery of a pharmacological agent); 15 min-1 hr (e.g. across a duration spanning multiple therapeutic or interventional actions, such as ablation in more than one region or through active and dissipative phases of a pharmacological agent); 1 hr-6 hs (e.g. across portions of a procedure); greater than 6 hours (e.g. between multiple procedures, for example within a day or over a patient's lifetime); and combinations of one or more of these. Similar information can be assessed over durations of different orders of magnitude to determine consistency and/or persistence of the complexity. For example, cardiac information, such as rotational or focal activation or an index of complexity, can be identified for a set of activations within a 4 sec time window. The same cardiac information can also be assessed over multiple such time windows within several minutes to demonstrate consistency of the pattern over the several minutes. The same cardiac information can also be assessed before and after a set of ablations to determine the effectiveness of ablation in the targeted region in reducing the presence of the rotational or focal activation or complexity.

With the anatomy represented by a plurality of nodes, and activation state at a given time determined for each node, the Coulombian map can be determined by using $1^{st}$, $2^{nd}$, and/or $3^{rd}$ (or more) neighbors of each node. A broader spatial range can be considered when computing the Coulombian map using more neighbors in the computation. This Coulombian map can be displayed and/or further processed to show and/or determine the active wave front. In some embodiments, the Processor 26 can be configured to smooth the activation wavefront by using a smoothing filter and/or a noise reduction filter. One example of such a filter is a median filter or other nonlinear filter used to remove noise from a node based set of data. A filter such as this can be implemented by replacing the value at each node with the median value of the node along with its neighbors. The number of neighbors can be user defined, pre-determined, and/or a time varying value.

The 3D Display 242 can be used to display the outputs from the post-processing tools 730. That is, for example, surface DD/CDNoltages, as well as post-processing maps, can be rendered by selecting options on the display panel of UI system 230. The 3D maps can be rotated to different viewing angles and a color map can be adjusted by a user, as examples. The post-processing tools can be configured to support determination and display of node activation statuses, as discussed herein.

Figure 8A:
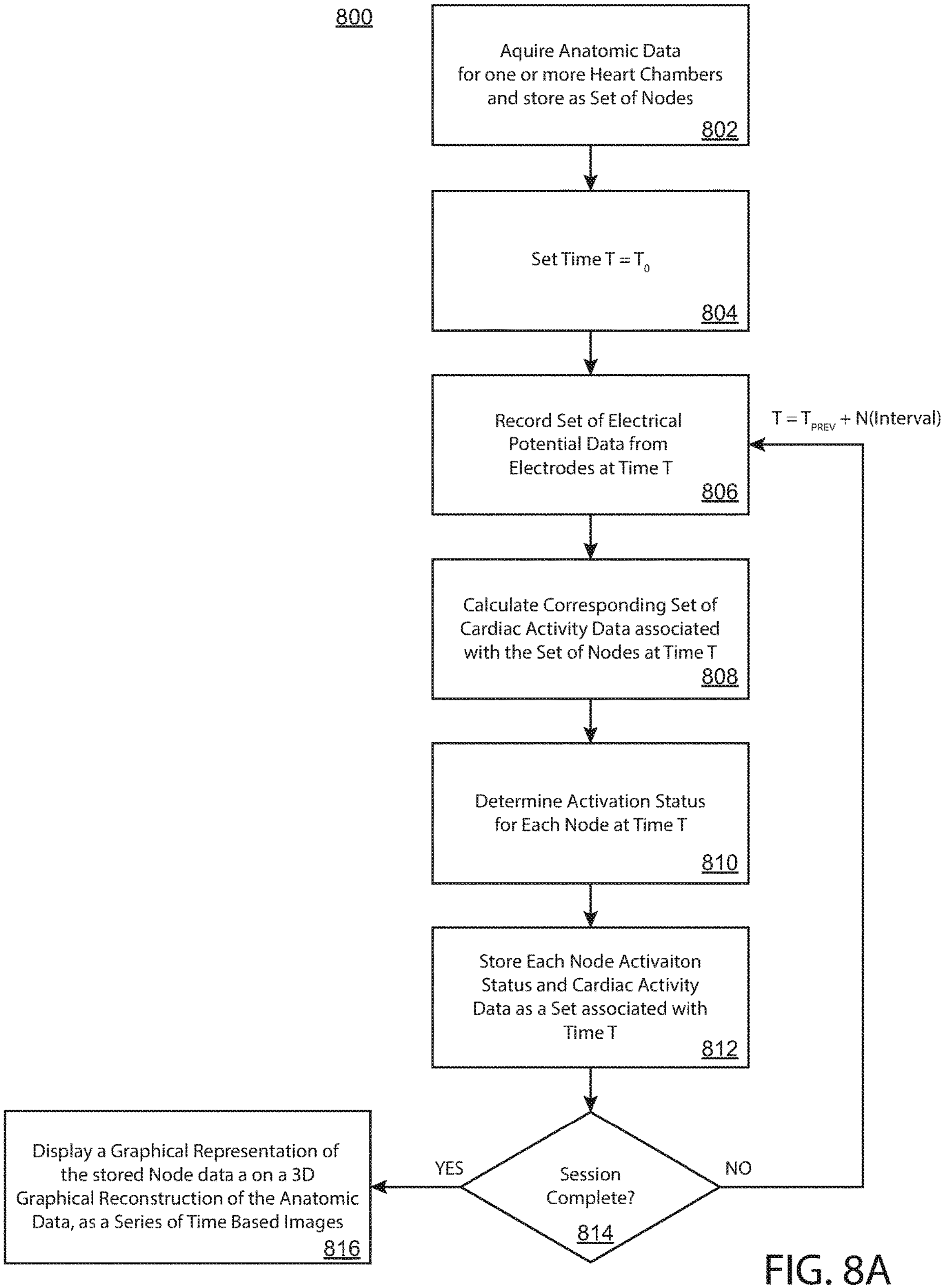
FIG. 8A is a flow chart of an embodiment of a cardiac information dynamic display method, in accordance with aspects of the inventive concept.

FIG. 8A is an embodiment of a cardiac information dynamic display method, in accordance with aspects of the inventive concept. The method 800 of FIG. 8A can be implemented by the various systems described herein. The method 800 may be carried out by the system 100 of FIG. 1, including the UI system 230 of FIG. 6 and the processing system 700 of FIG. 7.

In step 802, anatomical data corresponding to one or more heart chambers is acquired, and stored as a set of interconnected nodes representing surfaces of the heart chambers (e.g., a point cloud or surface mesh). For example, in some embodiments, the anatomy (heart chamber) can be represented in memory by 3-10 thousand nodes. This anatomical data could be acquired by the US transducers 12*b* and signal processing elements discussed above, such as US signal path 60 and US processor 66. In other embodiments, the anatomical data can be acquired by other types of technologies and system, such as magnetic resonance imaging (MRI).

In step 804, a time T is set as $T_0$, as an initial reference time. To can indicate the beginning of a cardiac data acquisition session, where the electrodes 12*a* can sense and/or record biopotentials from cardiac activity during the session. In some embodiments, To can indicate the beginning of a time period of recorded cardiac data. In some embodiments, the session duration can be preset. In other embodiments, the session can end in response to a user action with the cardiac information processing system 100 or the cardiac information console 20.

Within the session, biopotentials can be recorded or read from recordings at multiple intervals (N), where each new time T is the previous T plus N. As examples, a session for recording biopotentials can be in a range of 100 ms to 30 s (seconds), or several minutes (such as 2, 5, 10, or more minutes), and an interval N could be 0.3 ms. Acquiring or reading biopotentials for each electrode at every interval N, e.g., 0.3 ms, provides a measure of cardiac activity at time T. The inventive concept is not necessarily limited to such session durations and/or intervals. It is preferable that the session includes a plurality of intervals. The inventive concept is also not necessarily limited to separate steps of recording and processing of biopotentials, they may be simultaneously performed.

In step 806, a set of electrical potential data is recorded or read for the time T, initially $T_0$, e.g., using electrodes 12*a*. The electrical potential data for all electrodes can be stored in a data storage device 25 of the cardiac information console 20 in FIG. 1. In step 808, cardiac activity data is calculated from the electrical potential data and associated with the set of nodes representing the anatomy of the one or more heart chambers, e.g., in 3D space. The cardiac activity data can take the form of or include at least one or more biopotentials, such as those recorded by the electrodes 12*a*, surface charge densities calculated from the biopotential data, surface dipole densities calculated from the biopotential data, surface voltage calculated from the biopotential data, and/or the surface Coulombian data calculated from the charge density, dipole density, or voltage, e.g., see FIG. 7. The cardiac activity data can also take the form of and/or incorporate the spatial and/or temporal $1^{st}$ or $2^{nd}$ derivatives of any of these.

In step 810, from the cardiac activity data, an activation status is determined for each node in the set of nodes. The activation status for each node can be stored for time T. Therefore, for each time T in the session, a set of node-specific activation statuses can be determined and stored. In some embodiments, it is preferable for the cardiac information console 20 to determine the activation status of all nodes in the set of nodes within a single interval. Thus, a set of node-specific activations statuses can be stored for each time T in the session. The activation status of all nodes in a set of nodes for a time T can be determined without cardiac activity data, e.g., dipole densities, from other times T. In this sense, the determination of activation statuses for all nodes in a set of nodes for a time T can be considered discrete. Thus, the activation statuses for all nodes at a time T provides a snapshot of cardiac activation for the time T, without aggregating data from previous times.

Referring to steps 810-812, in various embodiments, the node activation determination method can employ one or more thresholds applied to one or more forms of the cardiac activity data, beyond which (above or below) the node can be considered activated and within which (below or above) the node is considered not activated. The method can be carried out by the cardiac information console 20, which can be configured to determine activation status at each node at a given time T with reference or respect to the threshold value.

In various embodiments, the threshold value can be a non-dynamic value, i.e., a value that does not change over time. In some embodiments, the non-dynamic value can be set as a percentage of a max range below zero for the cardiac activation parameter under analysis, e.g., voltage biopotential, surface charge density, or dipole density. In various embodiments, the threshold level can be set to 1% of the maximum range below zero=activated, which works well for healthy tissue. Thus, once the dipole density, as an example, drops below the threshold level, the node is considered "activated". In non-healthy, ablated tissue, and/or other areas of poor conduction, 1% of max may not be an effective value for non-dynamic thresholding.

In other embodiments, the threshold value can be a time-dependent dynamic value, referred to as dynamic thresholding. The time-dependent dynamic threshold value can be variable to account for temporal, spatial, global, regional, and/or local differences in tissue. Thus, the time-dependent dynamic threshold value can be different at different points in time for some or all of the nodes. In some embodiments, the time-dependent dynamic threshold value at different points and/or different nodes can be determined by analysis of or mathematical operation on one or more of the cardiac activation parameters, e.g., voltage biopotential, surface charge density, or dipole density. Mathematical operations may include, but are not limited to: first or second time derivatives, spatial or temporal filters, and/or quantitative comparisons, such as thresholds.

Dynamic-thresholding may be preferable to non-dynamic thresholding. Cardiac signals (e.g., charge density, dipole density, voltage, etc.) vary across the endocardial surface in magnitude. The magnitude of these signals is dependent on several factors, including local tissue characteristics, e.g., healthy vs. disease/scar/fibrosis/lesion, and regional activation characteristics, "electrical mass" of activated tissue prior to activation of the local cells. One common practice could be to assign a single threshold for all signals at all times across the surface, such as with non-dynamic thresholding discussed above. The use of a single threshold can cause low-amplitude activation to be missed or cause high-amplitude activation to dominate/saturate, leading to degraded accuracy and ambiguity in interpretation of the map. Failure to properly detect activation can lead to imprecise identification of regions of interest for therapy delivery or incomplete characterization of ablation efficacy.

With dynamic-thresholding, the threshold for detection of activation can be calculated for each location, node or group of nodes, on the surface, independently. The algorithm can take into account, as an example, one or more of the following:

a) The time-history of local activation, b) The chamber-wide area of activated tissue prior to local activation, c) The present, local surface signal magnitude, and/or d) The historical surface signal magnitude of neighbors.

In some embodiments, system 100 is configured to utilize multiple dynamic and/or non-dynamic thresholds to determine activation for a single node for a given time T. For example, a first dynamic or non-dynamic threshold may exist for the biopotential data, and a second dynamic or non-dynamic threshold may exist for the Coloumbian of the biopotential data, or any other mathematical operation on the biopotential signal.

The method, e.g., step 810 from FIG. 8A, is carried out for each T within a time window, with indicia of activation status stored in memory for each T. A processor (e.g., processor 26) determines if the cardiac activity data (e.g., biopotential value, surface charge density value, or dipole density value) at each node is above the threshold value for the node. If the cardiac activity data has a value that exceeds a threshold value, then the node is indicated in memory as "activated," for the time T. Otherwise, the node is indicated as not activated for time T.

In various embodiments, one or more of steps 808, 810, and 812 can be performed after the biopotentials from two or more times T are recorded as post-processing of the biopotential data.

Referring to step 810, the process for determining activation of a node in step 810 may include determining the Coulombian at this node, as mentioned above. The Coulombian can be determined as a distance weighted spatial Laplacian.

The Laplacian, defined as the divergence of the electrical field, is a means of finding the sources and the activations. Let Φ denote the electrical potential field. According to the electrostatics, the Laplacian ($\nabla^2$) of Φ is then correlated to electric charges ρ, and can be determined as follows:

$$\Delta\Phi = -\rho/\varepsilon \tag{1}$$

where ε is the dielectric permittivity of the blood.

One way to estimate the Laplacian on a triangular surface was proposed by Oostemdorp in 1989 via computing the Laplacian of each vertex among its direct neighbored vertices numerically. (see Oostendorp T F, van Oosterom A and Huiskamp G. (1989). Interpolation on a triangulated 3D surface. *Journal of Computational Physics,* 80, 331-343). In accordance with aspects of the inventive concept, the Laplacian is extended to determine the Coulombian, considering a wider area to compute ΔΦ at each node.

According to the method, the endocardial surface is represented by a triangular surface in a three-dimensional (3D) space. The surface voltages can be treated as functions defined on each vertex, denoted $\varphi_i$ for vertex $v_i$. Different from the numerical Laplacian defined on a surface by Oostemdorp, which only considers the direct neighbors, the calculation of Coulombian extends to involve more neighbors, e.g., $2^{nd}$, $3^{rd}$ or more neighbors and weights them by distance.

The indices of neighbored vertices surrounding a vertex $v_i$ can be defined iteratively, as follows:

$$1^{st}\text{ neighbor:} \quad I_i^1 = \{j \mid v_j, v_i \text{ are sharing the same edge, } j \neq i\} \tag{2}$$

$$2^{nd}\text{ neighbor:} \quad I_i^2 = \left(\bigcup_{j \in I_i^1} I_j^1\right) \Big/ \{i\} \tag{3}$$

$$\ldots$$

$$K^{th}\text{ neighbor:} \quad I_i^k = \left(\bigcup_{j \in I_i^{k-1}} I_j^1\right) \Big/ \{i\} \tag{4}$$

Figure 8B:
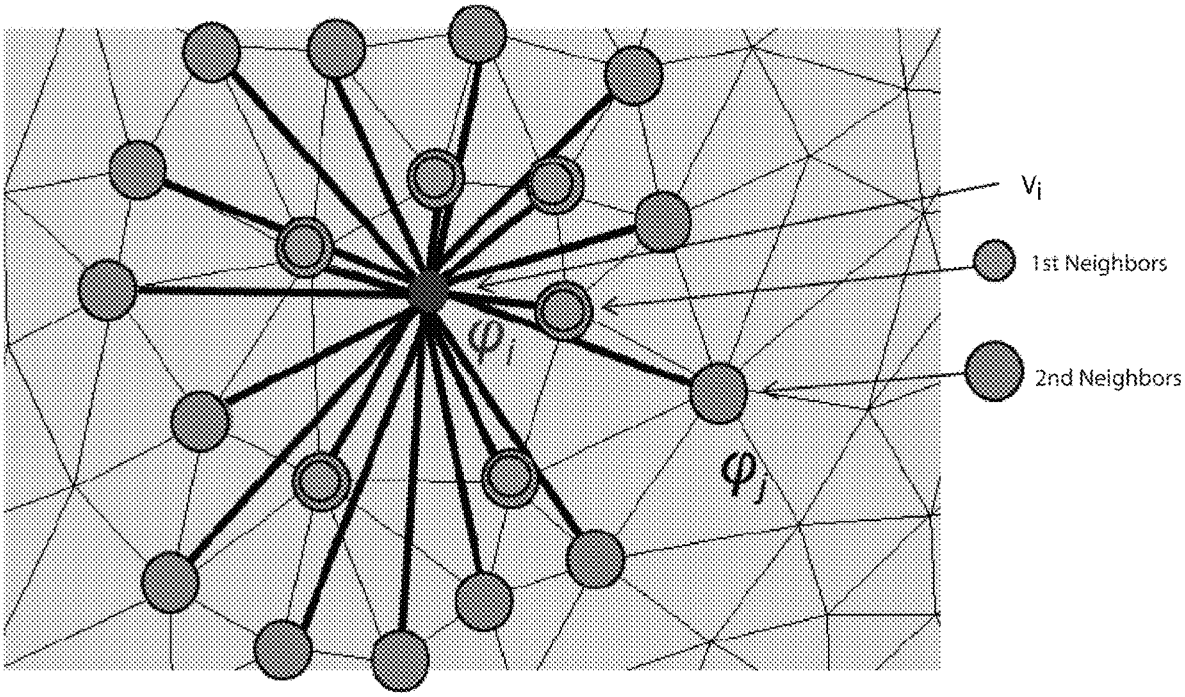
FIG. 8B is a drawing of a set of nodes of a reconstructed anatomy, in accordance with aspects of the inventive concept.

FIG. 8B shows a partial representation of the anatomy, e.g., heart chamber, represented as a set of nodes. Here, the nodes are the vertices of a geometric representation, e.g., triangular meshes covering portions of the anatomy. As an example, FIG. 8B shows the $1^{st}$ neighbor nodes (smaller dots) and $2^{nd}$ neighbor nodes (larger dots) of a vertex $v_i$ at a node under analysis, with surface voltage pi illustrated.

The Coulombian of voltage on vertex $v_i$ is defined as:

$$\Delta\varphi_i \approx \frac{4}{\bar{h}_i^2}\left(\frac{1}{n_i}\sum_{j\in I_i^k}\tilde{\varphi}_j - \varphi_i\right) \tag{5}$$

$\tilde{\varphi}_j$ is estimated voltages on $k^{th}$ neighbored vertices v by the Taylor expansion:

$$\tilde{\varphi}_j \approx \varphi_i + \frac{\bar{h}_i}{h_{ij}}(\varphi_j - \varphi_i) \quad j \in I_i^k \tag{6}$$

where $h_{ij}$ is the Euclidean distance from vertex $v_i$ to vertex $v_j$. And $$\bar{h}_i = \frac{1}{n_i}\sum_{j\in I_i^k} h_{ij}$$

is the mean distance between vertex $v_i$ and its $k^{th}$ neighbored vertices. And $n_i$ is the number of $k^{th}$ neighbored vertices of $v_i$, in other words, the number of elements in the index set $$I_i^k.$$

Rewrite Equation (5) with matrix notations:

$$\Delta\Phi = L\Phi \tag{7}$$

where matrix L is called the Coulombian operator, defined as:

$$L = (l_{ij})_{n\times n}, \tag{8}$$

where $$l_{ij} = \begin{cases} -\frac{4}{\bar{h}_i^2} & j = i \\ \frac{4}{\bar{h}_i}\frac{1}{n_i}\frac{1}{h_{ij}} & j \in I_i^k \\ 0 & \text{others} \end{cases}$$

The Laplacian can be treated as a specific case of the Coulombian when only the direct neighbors are considered.

The determination of activation of a node in step 810 may also incorporate one or more surface signals, eg. surface voltage, charge density, dipole density, the Coulombian of surface voltage, charge density or dipole density, as well as any mathematical operations, such as first or second time derivatives, spatial or temporal filters, or quantitative comparisons, such as thresholds, on the surface signals.

Figure 9:
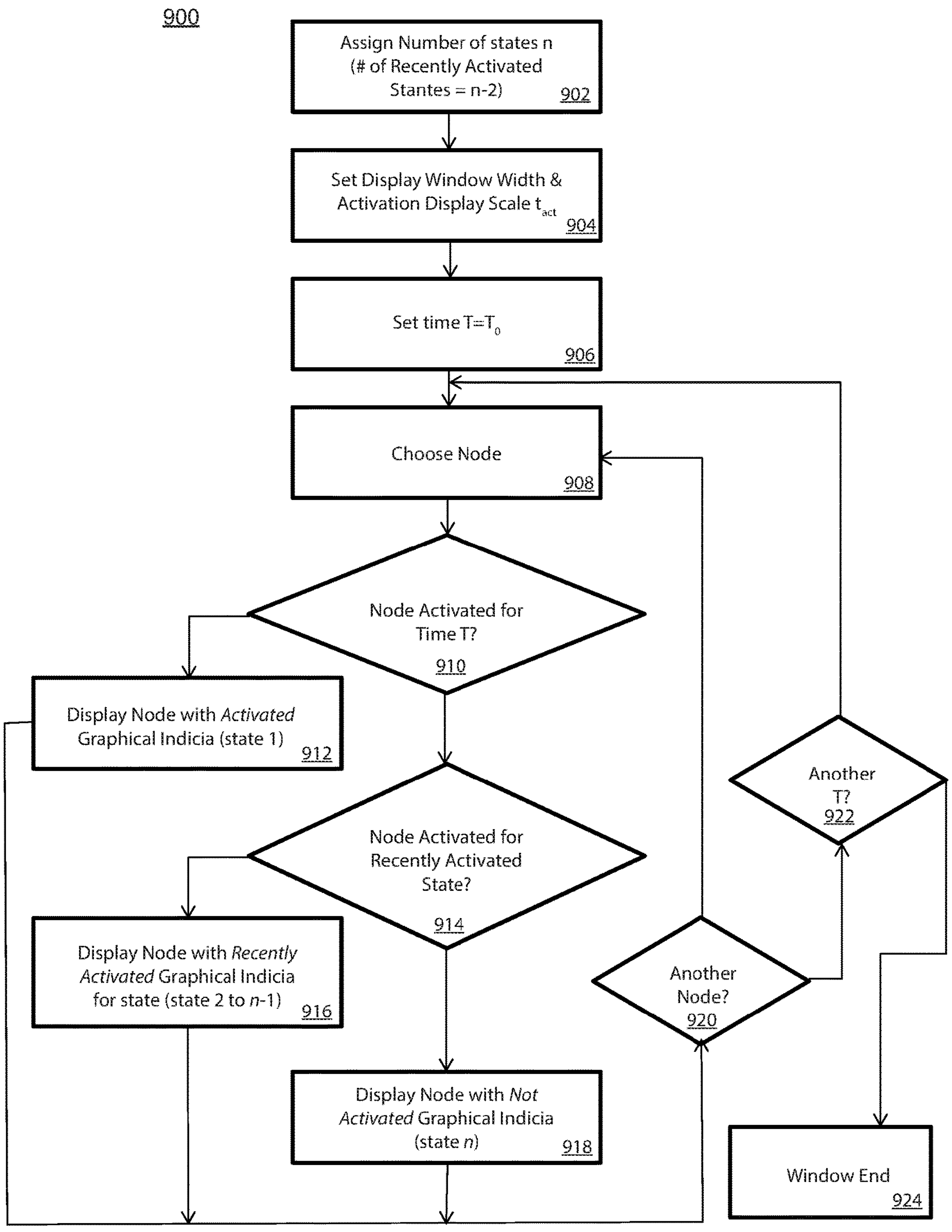
FIG. 9 is an embodiment of an activation display method, in accordance with aspects of the inventive concept.

FIG. 9 is an embodiment of a node activation display method, in accordance with aspects of the inventive concept. In particular, the method 900 of FIG. 9 may be considered an embodiment of step 816 of the cardiac information dynamic display method 800 of FIG. 8A. The method 900 provides an example of computer-based steps that could be used to display a plurality of nodes representing the anatomy of one or more heart chambers (HC) with graphical indicia that indicate whether or not a node is considered activated and, if not, whether or not it was recently activated or is not activated.

In step 902, a plurality of activation states n are determined. The activation states can be or include time-dependent states. A time-dependent state is a state that indicates node activation for a specific time or duration of time. The number of activation states will include an activated state and a not activated state. The not activated state can be a default state that is only changed if the node is indicated as activated or recently activated. The number of activation states preferably includes one or more recently activated states. For example, if 11 activation states are defined, there can be an activated state, a not activated state, and 9 recently activated states.

For each activation state, a different color, pattern, symbol, opacity, stippling, hue, or other graphical indicia can be applied to a node. For example, if n=11, there would be 11 different graphical indicia that can be associated with a node based on the node's activation state, i.e., activated, recently activated, or not activated. Recently activated nodes can have different graphical indicia, e.g., a different graphical indicium for each recently activated state. Using the example above where n=11, there would be 9 different graphical indicia for 9 different recently activated states, e.g., 9 different colors, representing 9 different recently activated states.

In step 904, a display window width can be defined, as well as an activation display step $t_{act}$. The display window width is a defined duration of time of cardiac activity displayed at a particular point in time. It can act as a sliding window in a dynamic display of cardiac activity. The activation display step is the time duration of each of the activated and recently activated states. In step 906, a time T can be set to $T_0$, as a starting point for the dynamic display of the activation status of the nodes. $T_0$ can indicate the starting point of the cardiac activity data session referred to in FIG. 8A.

For example, if the activation display step is 3 ms, a node stored as activated at time T or up to 3 ms before time T will be displayed as activated. Similarly, each of the recently activated states after the activated state can also have a 3 ms duration. In such a case, the first recently activated state will apply to a node that was activated more than 3 ms, but not more than 6 ms after T. The second recently activated state will apply to a node that was activated more than 6 ms, but not more than 9 ms after T. This pattern will continue for the remaining recently activated states. When a node is no longer indicated as activated or recently activated, it can default back to a not activated state.

In step 908, the processor chooses a node for analysis from the set of nodes. In step 910, a determination is made of whether or not the node is activated for a duration of time from T to T-$t_{act}$, as discussed above. If the node is activated in step 910, the process continues to step 912, where a graphical indicium associated with the activated state is assigned to the node for display, e.g., a particular color can be assigned to the node.

If the determination in step 910 is that the node was not activated at time T to T-$t_{act}$, then the process moves to step 914. In step 914, a determination is made of whether the node was recently activated, as discussed above. Assuming there are a plurality of recently activated states, the processor looks back in time to increments having the duration of $t_{act}$ to determine whether the node was activated in any of those intervals and, if so, a specific graphical indicium (e.g., specific color) is assigned to the node associated with the appropriate interval for display, in step 916.

If the determination in step 914 was that the node was not recently activated, the node remains or changes to a not activated state, and a graphical indicium (e.g., color) associated with the not activated state is assigned to the node for display, in step 918.

The process continues from either one of steps 912, 916, or 918 to step 920. In step 920, a determination is made of whether there is another node in the set of nodes for the time T. If there is another node for analysis, the process continues to step 908 where another node is chosen and the process repeats for the chosen node. This can continue until all nodes for analysis from the set of nodes are assigned a graphical indicium for an associated activation status or state.

If, in step 920, there are no other nodes to be analyzed, the method continues to step 922. In step 922, there is a determination of whether there is another time T to be displayed. If more cardiac activity data remains for display, then T can be incremented to a next T, and the process can continue to step 908. If there are no other times T to be displayed, the process can end, in step 924.

Figure 10:
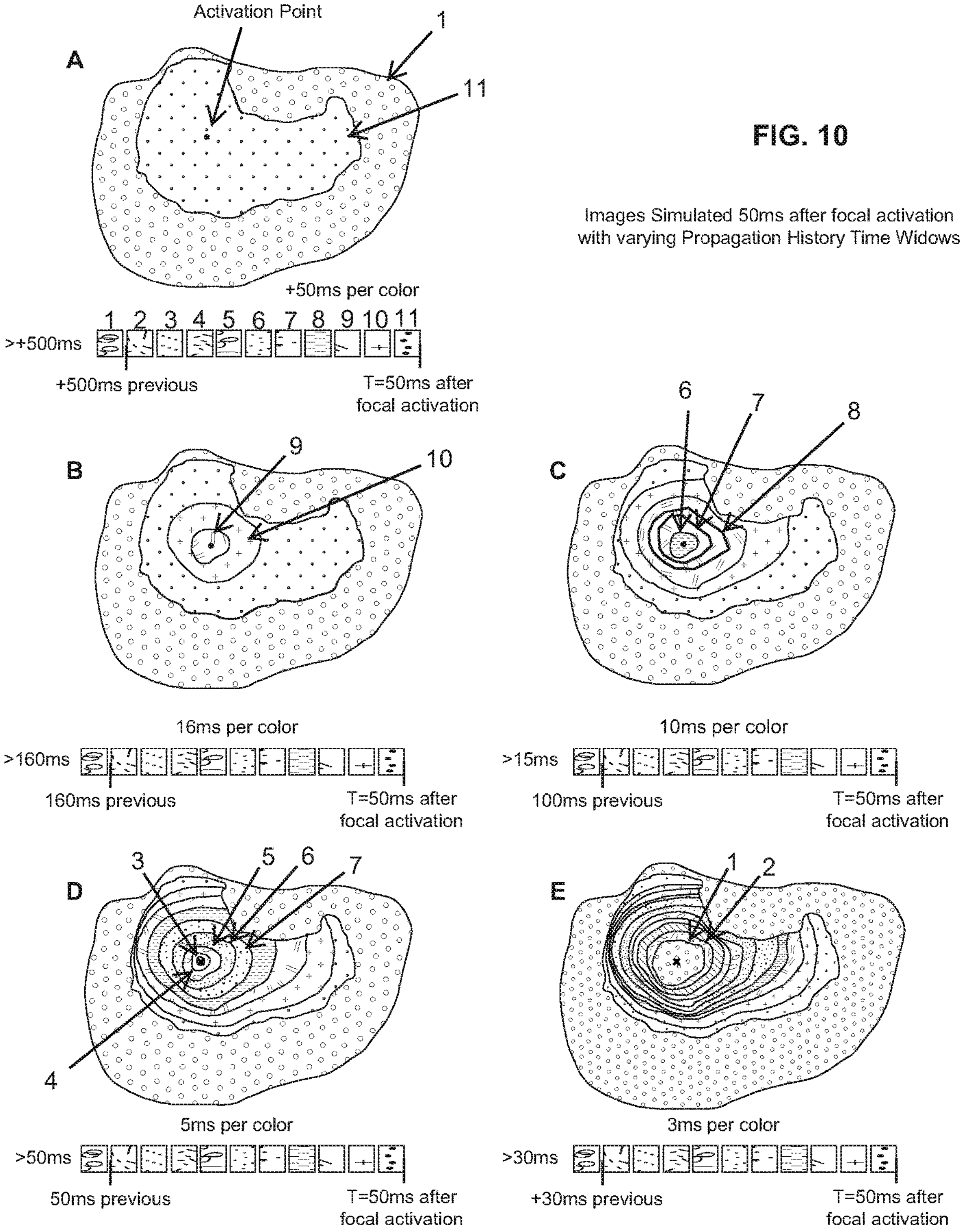
FIG. 10 is a set of views of an embodiment of cardiac activation data rendered on a digital model of cardiac anatomy, in accordance with aspects of the inventive concept.

FIG. 10 is an embodiment of a set of views of cardiac activation data rendered on a reconstructed heart, in accordance with aspects of the inventive concept. Views (a) through (e) show examples of five displays of activation superimposed on a representation of a heart. As described herein, any collection of colors, shades, hues or other visually differentiable features can be employed by system 100, such as a user-selectable collection of differentiable features. The heart is electronically reconstructed as a large number of nodes, and an activation status or state for each node is represented by a color. In this embodiment, there are 11 states, including an activated state, a not activated state, and 9 recently activated states. Each state, which can be depicted by a different color on a computer display, is depicted by a different pattern in FIGS. 10, 11, and 12A-O. In FIG. 10A, a legend of the different patterns is provided, numbered 1 through 11, indicating the different display colors. In each of views (a) through (e) 50 ms of data are shown.

In view (a), the heart is initially indicated as not activated with the color purple (pattern 1) associated with all nodes, prior to initiating the dynamic display at ">+500 ms." The heart is shown, however, at T=50 ms. The activation display step is set at 50 ms, which is the duration associated with each state. Therefore, from $T_0$ to T=50 ms, the display has only had enough time to display the first state, which is the activated state, in addition to the default not activated state. The activated state is distinguished by a specific color, e.g., red (pattern 11). The activated region has propagated outward from the "Activation Point," i.e., the cardiac "point of origin" of the activation in this example.

In view (b), the heart is initially indicated as not activated with the color purple (pattern 1) associated with all nodes, prior to initiating the dynamic display at ">160 ms." The heart is shown, however, at T=50 ms. The activation display step is set at 16 ms, which is the duration associated with each state. Therefore, from $T_0$ to T=50 ms, the display has had enough time to display the first state, which is the activated state, and two recently activated states, in addition to the default not activated state. The activated state and each recently activated state are distinguished by different colors (here patterns 9 and 10 are added). The activated region has propagated outward from the "Activation Point," the cardiac point of origin of the activation. The closer a recently activated state band is to the activated state band, the closer in time the activation was to the activated state.

In view (c), the heart is initially indicated as not activated with the color purple (pattern 1) associated with all nodes, prior to initiating the dynamic display at ">15 ms." The heart is shown, however, at T=50 ms. The activation display step is set at 10 ms, which is the duration associated with each state. Therefore, from $T_0$ to T=50 ms, the display has had enough time to display the first state, which is the activated state (pattern 11), and four recently activated states (patterns 6-10), in addition to the default not activated state (pattern 1). The activated state and each of the recently activated states are distinguished by different colors (patterns 6-11). The activated region has propagated outward from the "Activation Point," the point of origin of the activation. The closer a recently activated state band is to the activated state band, the closer in time the activation was to the activated state.

In view (d), the heart is initially indicated as not activated with the color purple (pattern 1) associated with all nodes, prior to initiating the dynamic display at ">50 ms." The heart is shown, however, at T=50 ms. The activation display step is set at 5 ms, which is the duration associated with each state. Therefore, from $T_0$ to T=50 ms, the display has had enough time to display the first state, which is the activated state (pattern 11), and nine recently activated states, in addition to the default not activated state (pattern 1). The first activated state and each of the recently activated states distinguished by different colors. Here, activated states represented by patterns 3-11 are shown. The activated region has propagated outward from the "Activation Point," the cardiac point of origin of the activation. The closer a recently activated state band is to the activated state band, the closer in time the activation was to the activated state.

In view (e), the heart is initially indicated as not activated with the color purple (pattern 1) associated with all nodes, prior to initiating the dynamic display at ">30 ms." The heart is shown, however, at T=50 ms. The activation display step is set at 3 ms, which is the duration associated with each state. Therefore, from $T_0$ to T=50 ms, the display has had enough time to display the first state, which is the activated state (pattern 11), and all nine recently activated states, in addition to the default not activated state (pattern 1). The activated state and each of the recently activated states are distinguished by different colors, here patterns 2-10. The activated region has propagated outward from the "Activation Point," the cardiac point of origin of the activation. The closer a recently activated state band is to the activated state band, the closer in time the activation was to the activated state.

Figure 11:
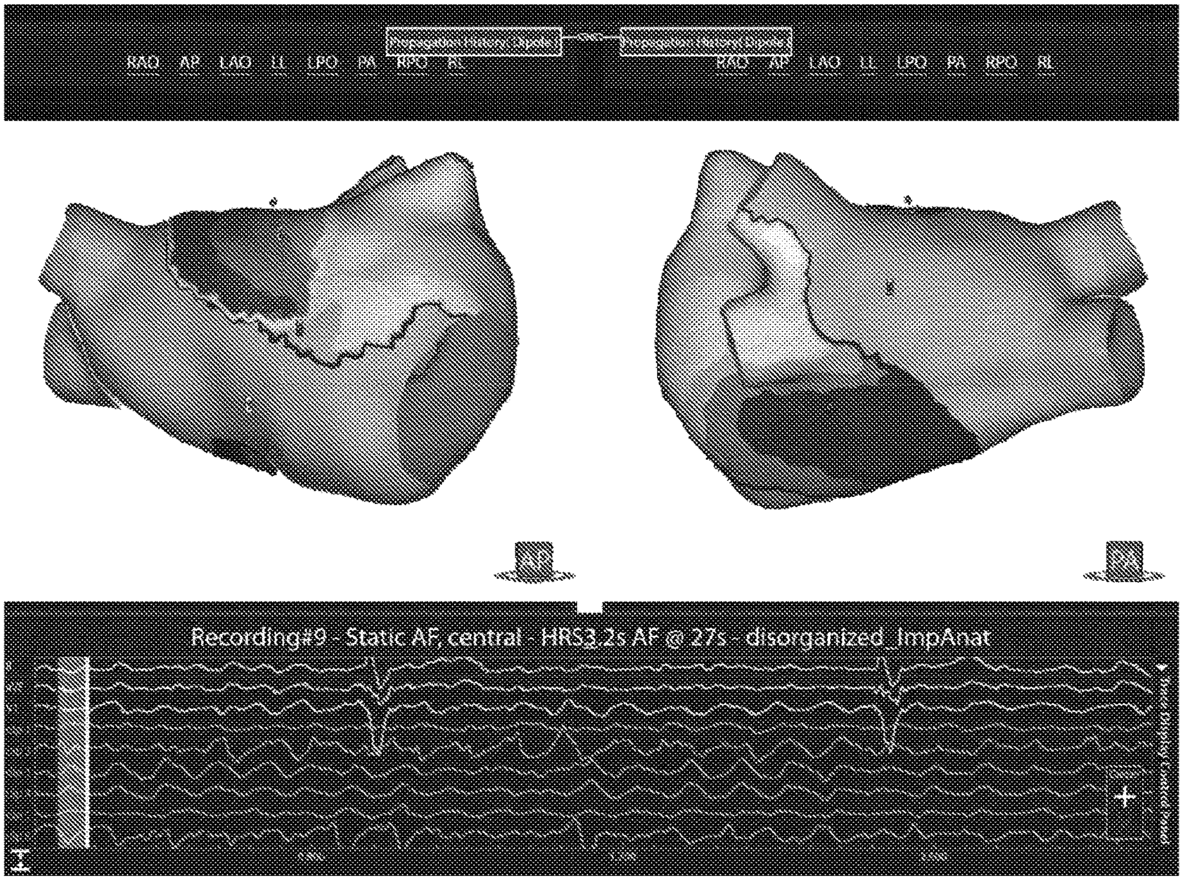
FIG. 11 is a set of views of an embodiment of cardiac activation data rendered in 3D on a digital model of cardiac anatomy, in accordance with aspects of the inventive concept.

FIG. 11 is an embodiment of a display of views of cardiac activation data rendered in 3D on a reconstructed heart, in accordance with aspects of the inventive concept. The display shows an EGM region, which is a 2D region, below the side-by-side 3D renderings.

In the right side view, the heart is shown from a first perspective with various bands of activation shown. The outermost band is the activated node band. The subsequent bands represent recently activated states, as described above. The activation statuses relate to the time indicated by the sliding window overlaid on the EGM, which has a horizontal time axis. The width of the sliding window reflects the 50 ms window width, referred to as "Propagation History" in FIG. 11. The duration of the activation display step $t_{act}$ is not indicated, but is about 5 ms.

In the left side view, a different perspective of the same heart is shown. This view shows that the activation wave has propagated around the heart. Various user-interactive devices may be provided in the display for manipulating the 3D images of the heart, e.g., rotating the images, adding labels to the images, and so on.

In various embodiments, the cardiac information dynamic display system can include video display control tools that enable a user to play, replay, rewind, fast forward, pause, and/or control the playback speed of the dynamic activation wave propagating over the heart.

Figure 12A:
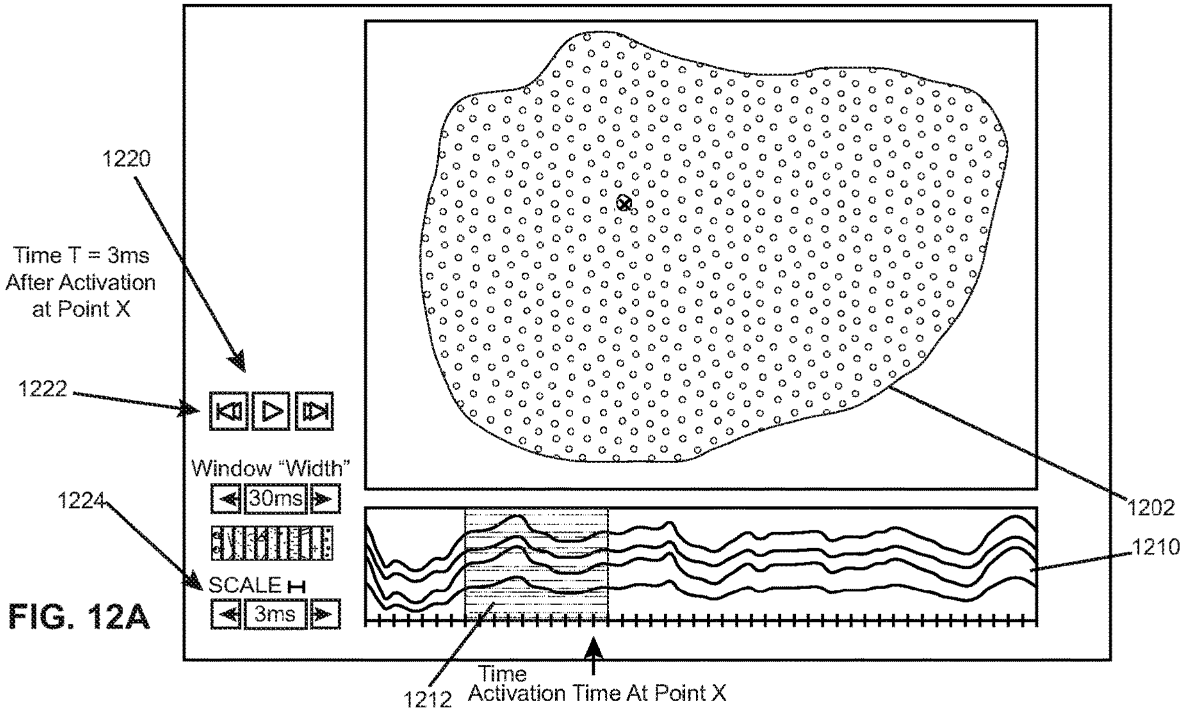
FIGS. 12A-12O are a set of views showing various embodiments of cardiac activation data rendered on a digital model of cardiac anatomy, in accordance with aspects of the inventive concept.
Figure 12B:
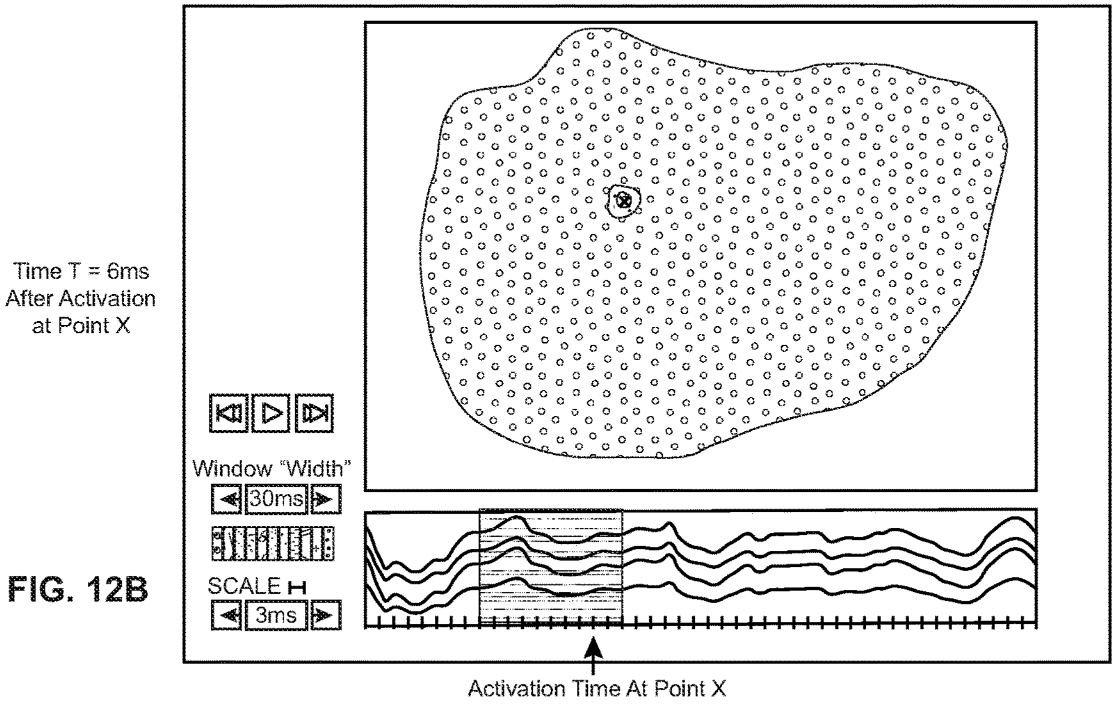
Figure 12C:
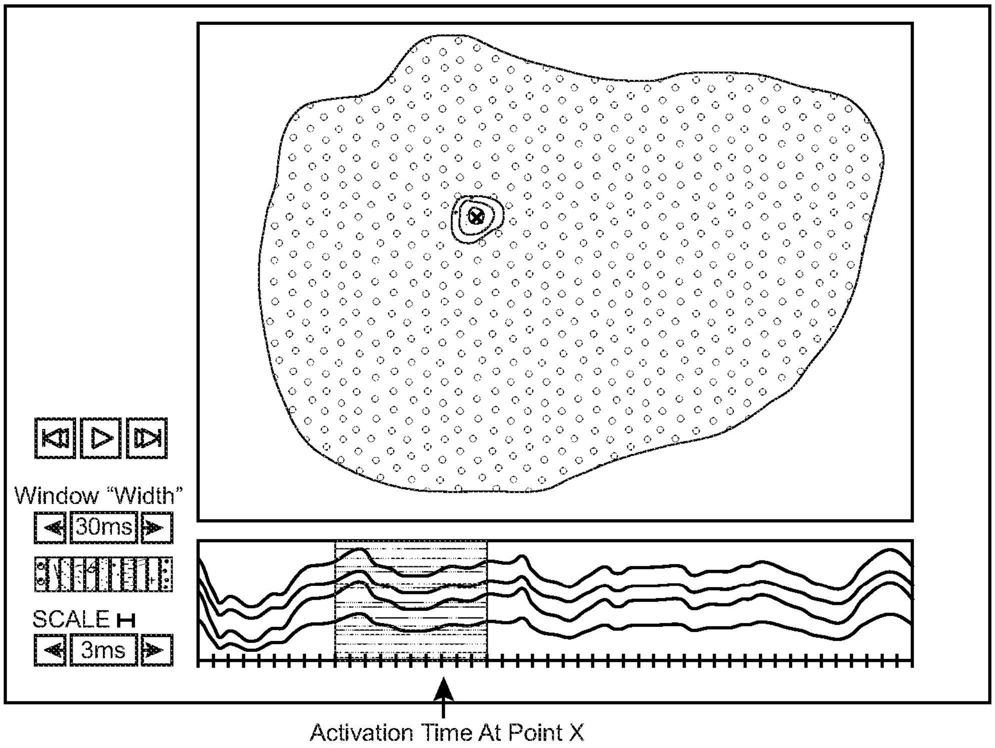
Figure 12D:
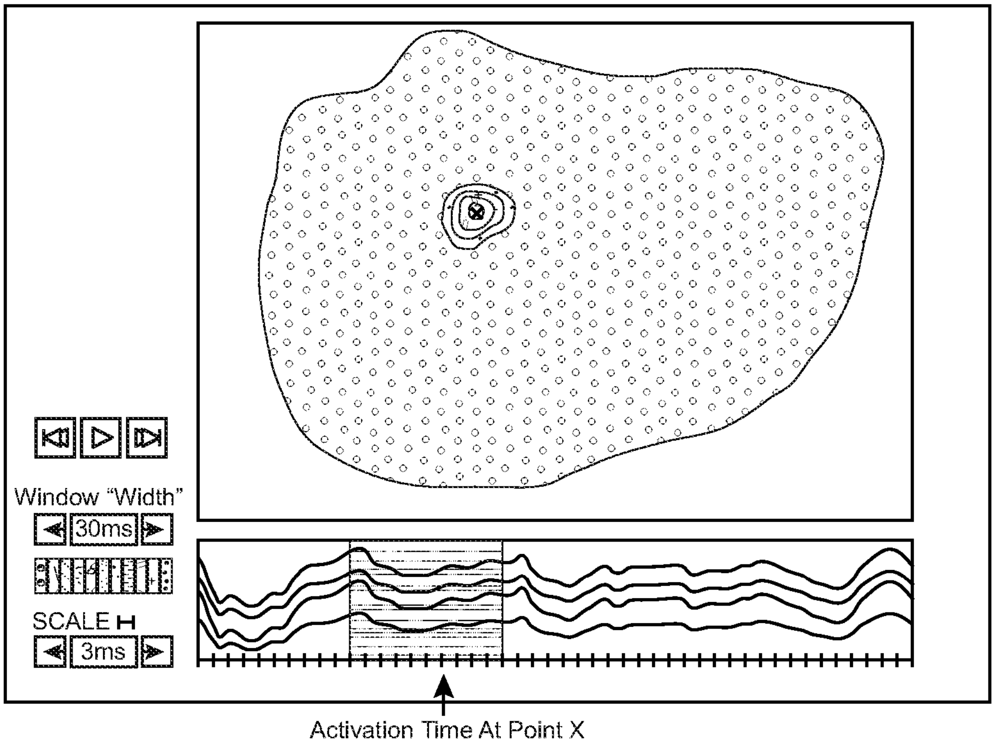
Figure 12E:
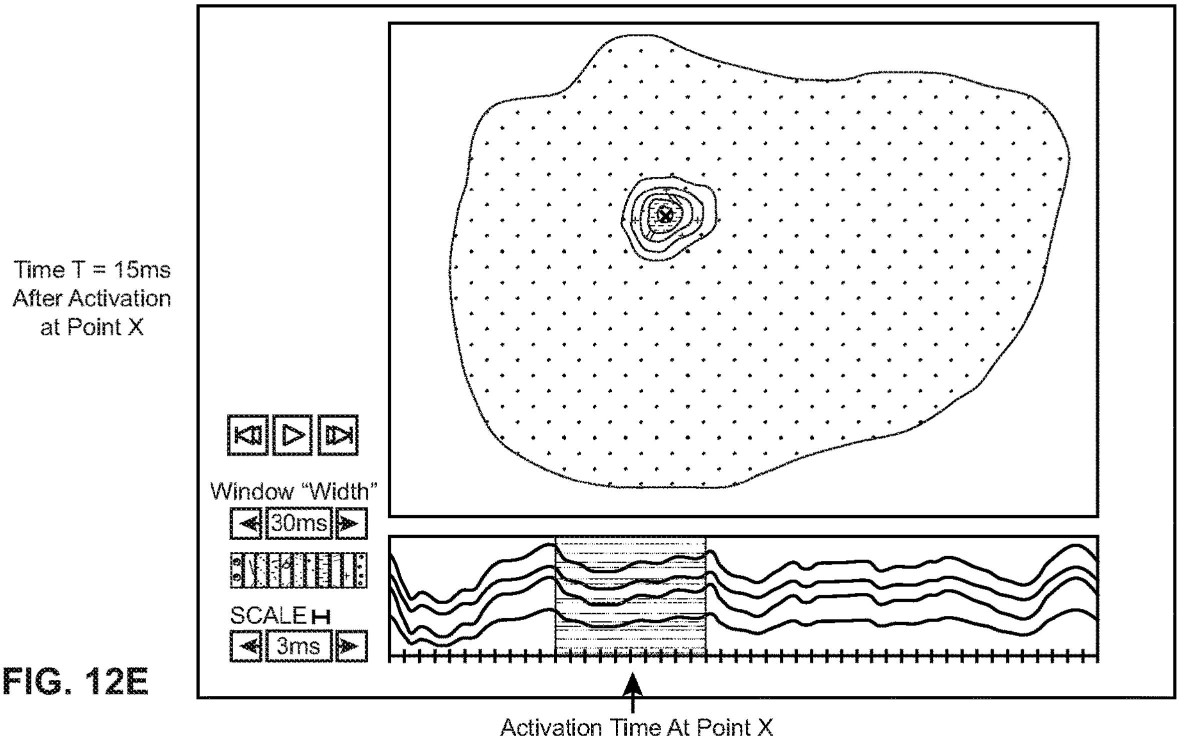
Figure 12F:
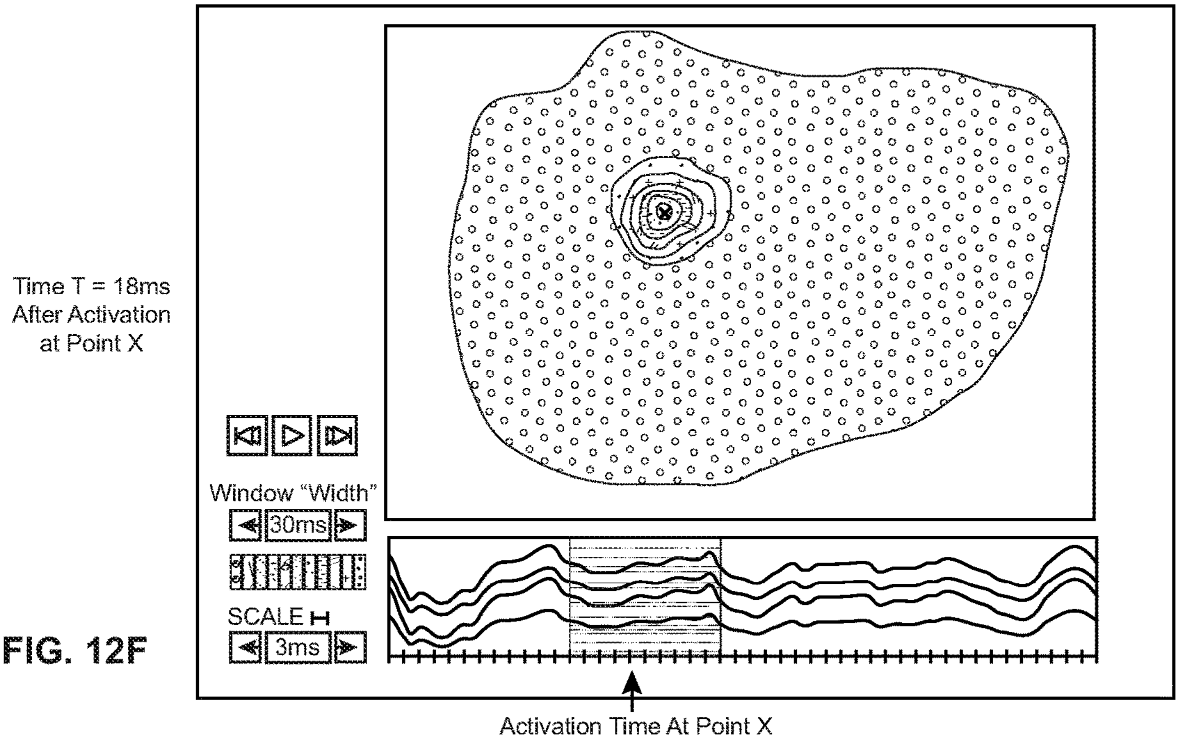
Figure 12G:
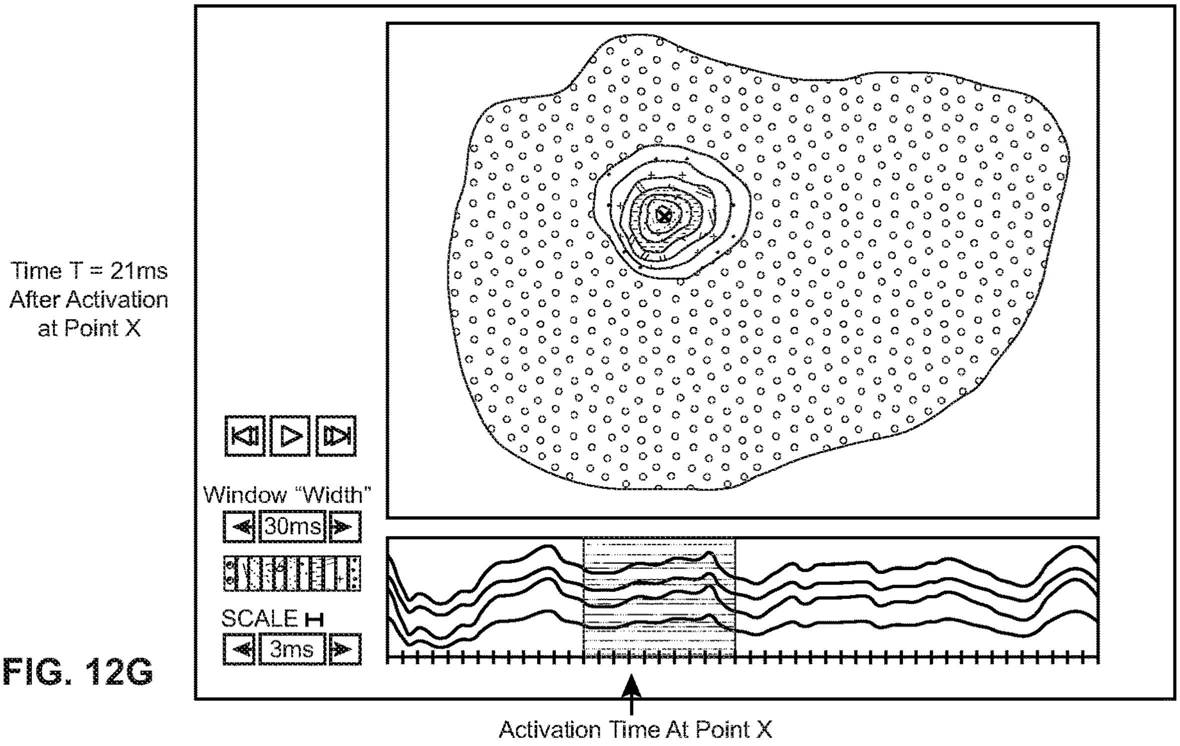
Figure 12H:
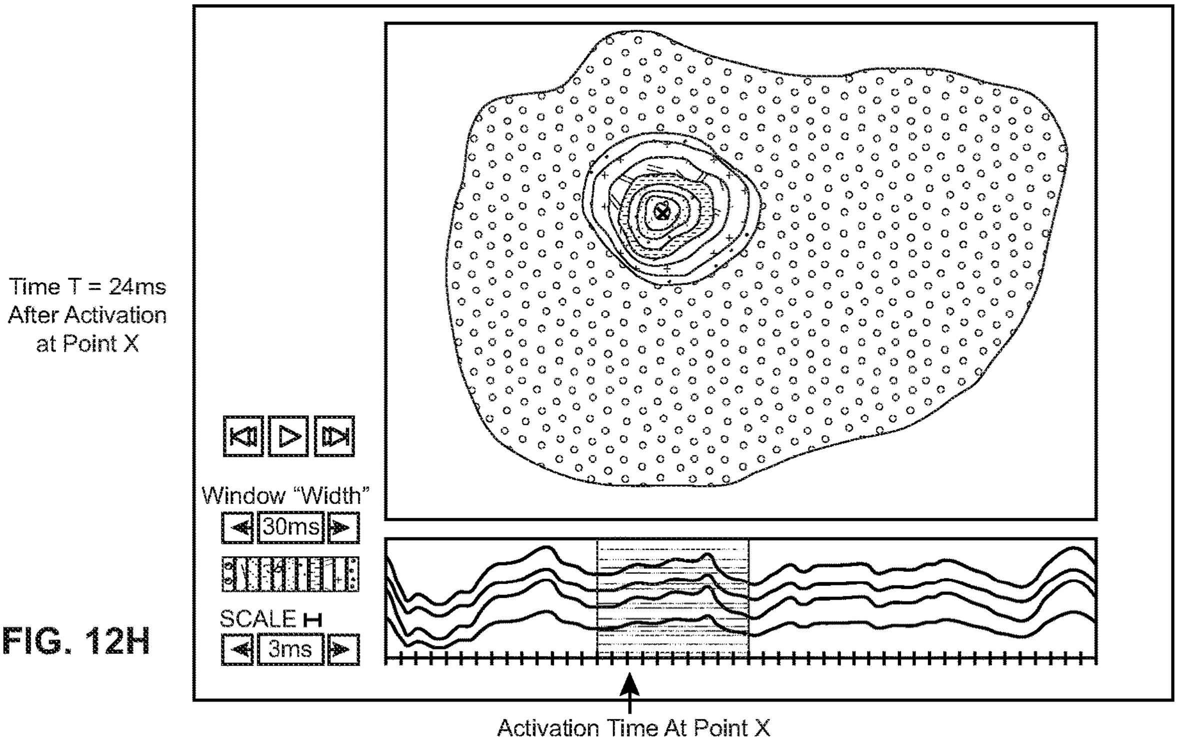
Figure 12I:
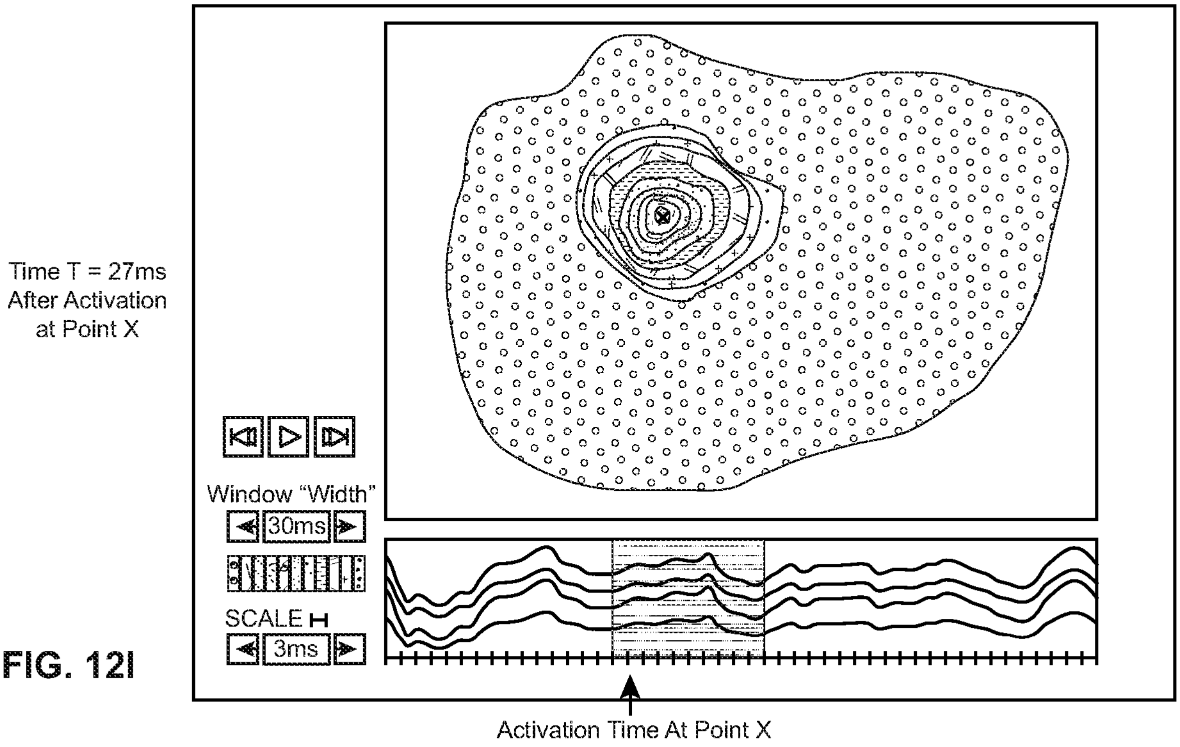
Figure 12J:
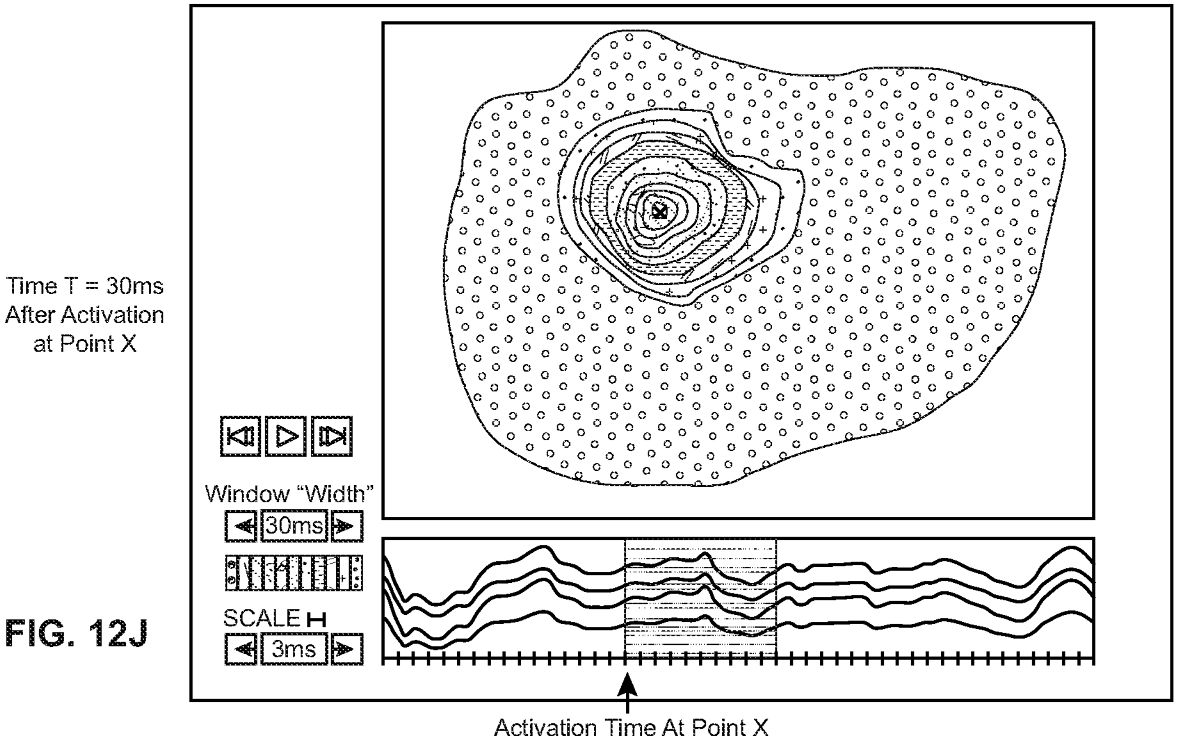
Figure 12K:
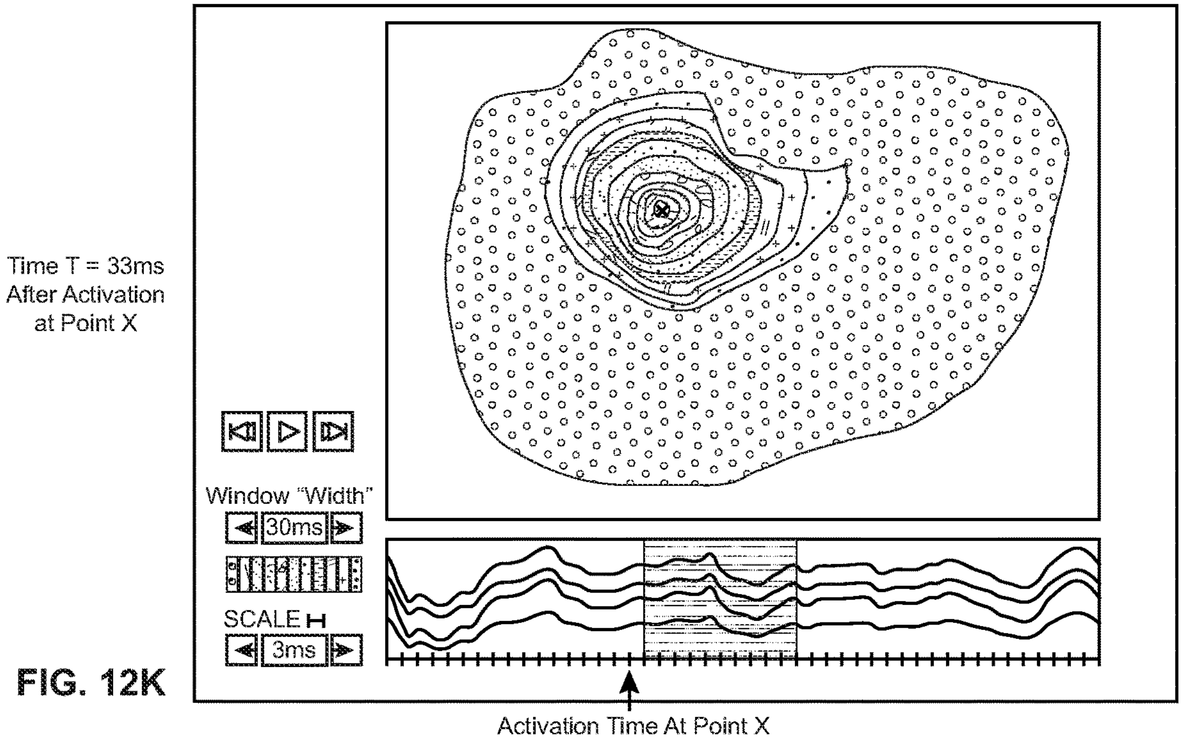
Figure 12L:
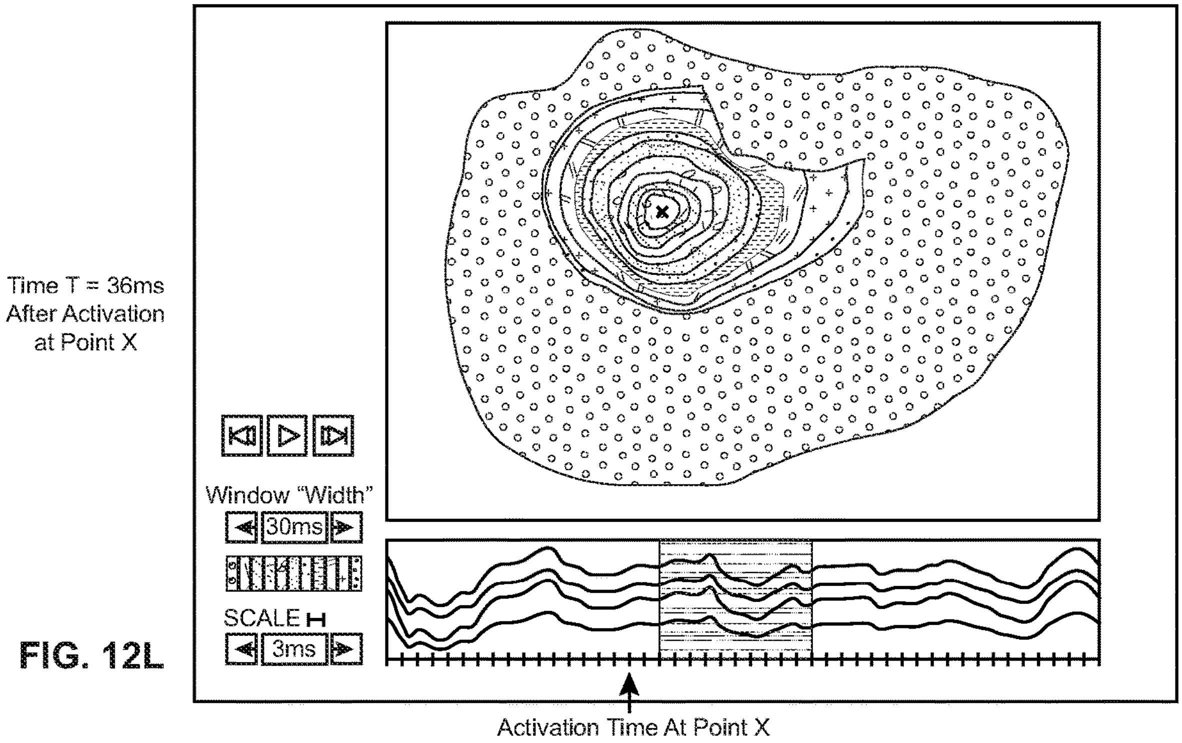
Figure 12M:
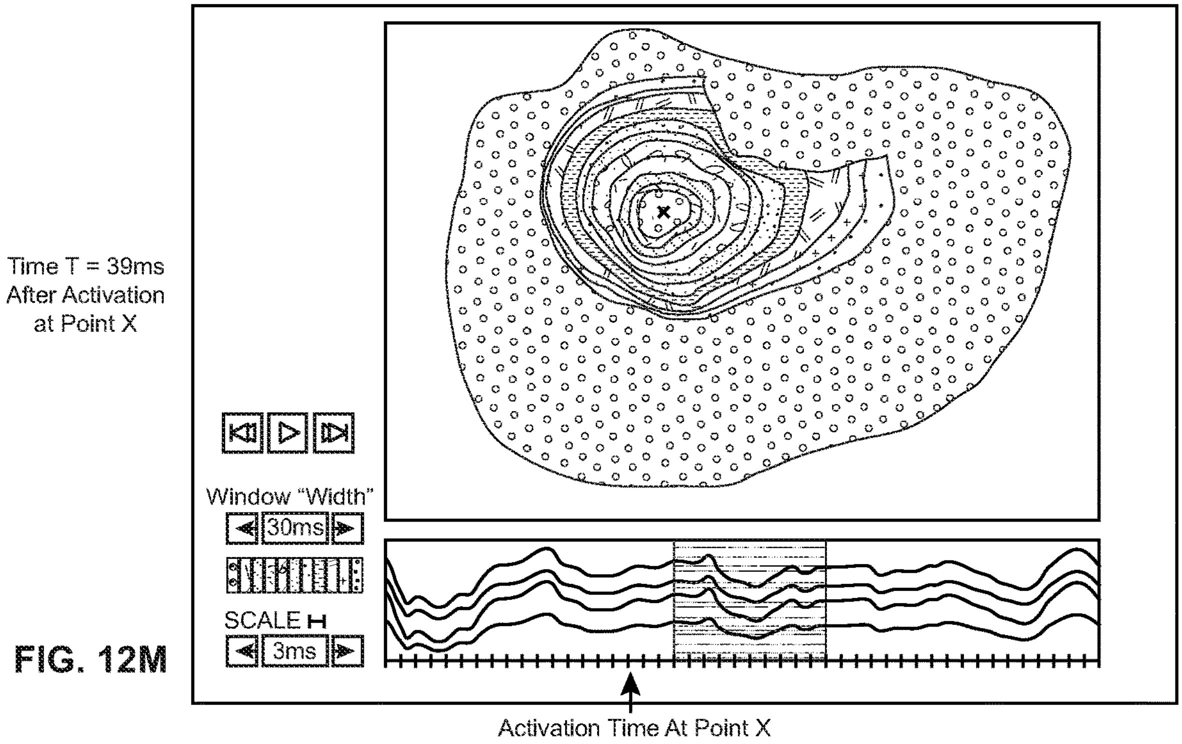
Figure 12N:
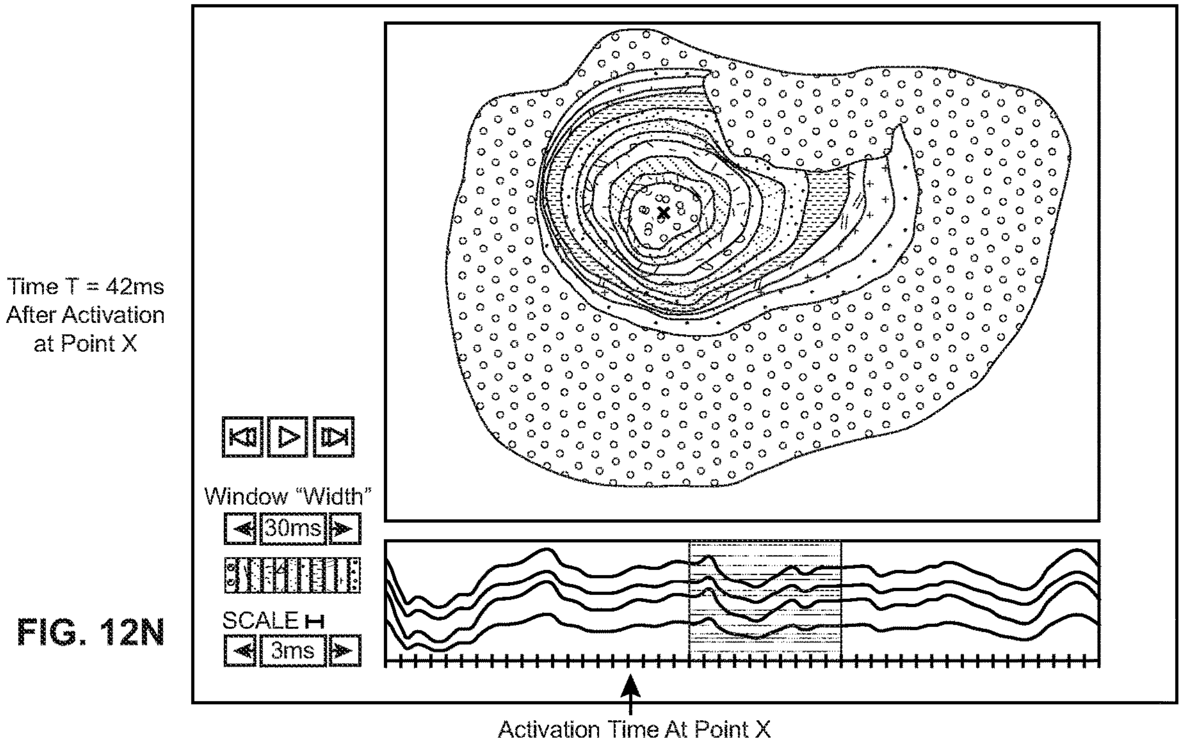
Figure 12O:
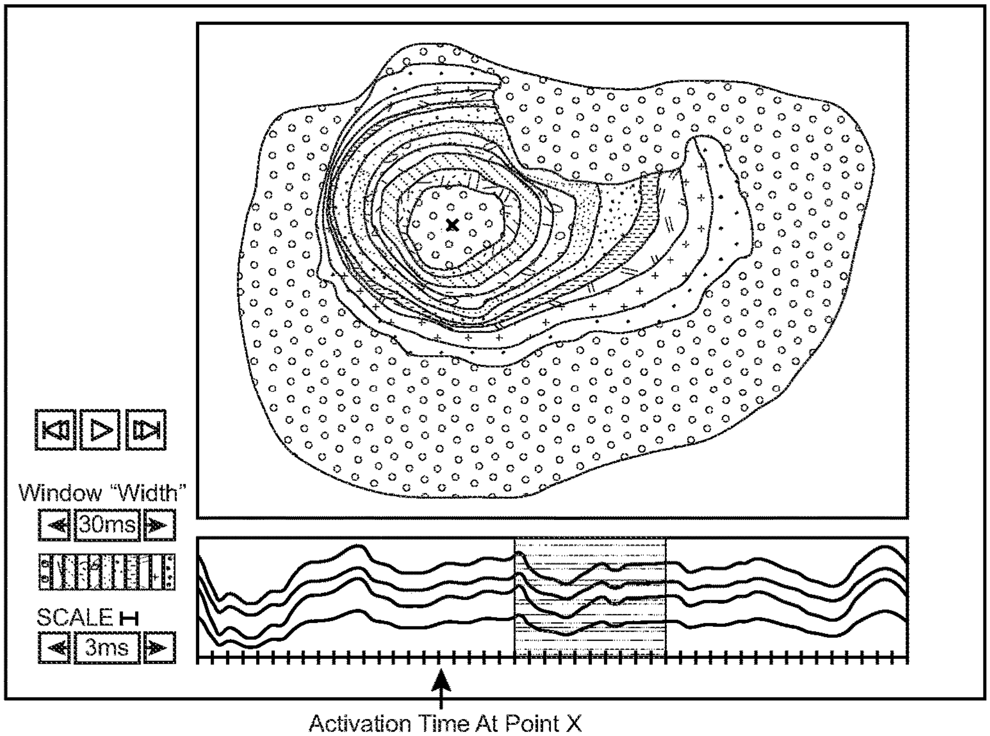

FIGS. 12A-12O show various embodiments of screens of cardiac activation data rendered on a reconstructed heart 1202, in accordance with aspects of the inventive concept. Like FIG. 11, an EGM 1210 is presented below a cardiac information display window that displays the reconstructed heart 1202 with activation status of a plurality of nodes superimposed thereon. Each screen includes a user-selectable window width scale and activation display step for setting $t_{act}$ 1220. Play, rewind, and fast forward controls are also shown.

The window width selector 1222, for setting a time duration for display, here set at 30 ms, e.g., by a clinician, is indicated in the semitransparent sliding window 1212 superimposed over the EGM. The activation display step selector 1224 for setting $t_{act}$ is set at 3 ms, e.g., by a clinician. Thus, each state n will have an interval of 3 ms, and 10 activation states can fit within one window, i.e., 30 ms/3 ms=10. As with FIG. 10, the displays show 11 total states, including 1 activated state, 1 not activated state, and 9 recently activated states. Each state is represented by a different pattern, such as patterns 1-11 in FIG. 10. On a display, each pattern can have a different color or other representation.

In FIG. 12A, 3 ms have elapsed since the node represented by point X became activated, time $T_0$ used herebelow. Thus, only a first state, the activated node state, is shown against the heart 1202. The heart is otherwise shown in the initial state of not activated with a specific graphical indicium, here the color purple (pattern 1). The activated node state is shown with its own specific graphical indicium, here the color red (pattern 11).

In FIG. 12B, 6 ms have elapsed since $T_0$. Thus, only two states are shown, the activated node state and a first recently activated node state. The recently activated node state is shown with a unique color (pattern 10, e.g. a lighter shade of the initial color, and/or the "next" color in a gradient, such as a RGB gradient), different from the other states.

In FIGS. 12C through 12O, the time T is incremented by 3 ms, showing an additional recently activated band for each interval, until all bands are shown in FIG. 12K, with T=33 ms. Collectively, FIGS. 12A through 12O show how an activation wave can propagate over a heart over time. User input devices for starting, stopping, rewinding, fast forwarding, and pausing the dynamic display are provided in this embodiment.

In various embodiments, the display settings, such as number of states, window width, and the activation display step can be user set to display the same set of cardiac activation information with different display parameters. The number of states can range between 2 and 64, such as 15 states. The window width can range from 1-500 ms, such as 50 ms or 100-300 ms. The activation display step can range from 1-200 ms, such as 6 ms or 10 ms.

Figure 13:
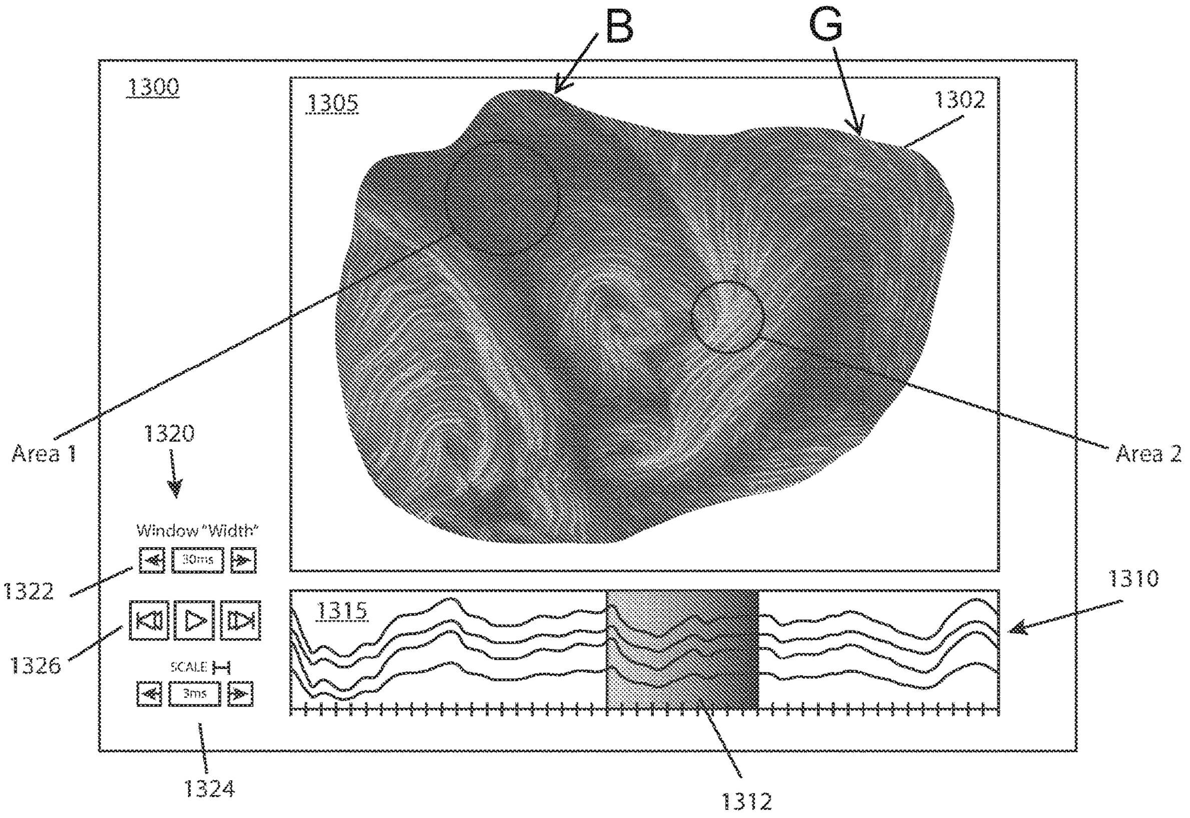
FIG. 13 is a view of an embodiment of cardiac activation data rendered in 3D on a digital model of cardiac anatomy, in accordance with aspects of the inventive concept.

FIG. 13 shows an embodiment of a display screen 1300 comprising multiple regions within which cardiac activation data can be rendered and user-interactive controls can be provided, in accordance with aspects of the inventive concept. The cardiac activation data is time series data, e.g., a duration of cardiac activity, that can be dynamically displayed as a function of time. A duration of cardiac activity data can be processed to calculate and display characteristics of the pattern of activation and/or conduction across nodes of a digital model of cardiac anatomy. In some embodiments, the characteristics of the pattern of activation and/or conduction that are calculated and displayed can include direction, velocity, acceleration, curi, angular velocity, vorticity, rotational angle, mean amplitude, max peak-to-peak amplitude, max negative peak amplitude, minimum re-activation time, mean re-activation time, and/or other characteristics that describe a pattern of flow and/or obstructions to it. In some embodiments, post processing can include processing as described hereabove. Displays described with respect to FIG. 13 can be generated using the same processors, modules, and databases described above for rendering other displays.

The characteristics of the pattern of activation and/or conduction can also be quantitatively combined with weighting to calculate and display a cardiac state index, "state index" herein. The number, regularity, and/or rate of occurrence of any characteristics of the pattern of activation and/or conduction during the duration of cardiac activity data can also be quantitatively calculated and displayed as a state index. The state index can also be compared against one or more thresholds, such as to form a separate, discrete state index. In some embodiments, a quantitative index may be calculated as described hereabove in reference to FIG. 7 and otherwise herein.

Also, as described herein, the data can be processed over extended periods of time, and the consistency (e.g. the consistency of an activation) can be displayed as a side-by-side comparison or can be displayed as a difference, highlighting either regions that stayed the same or regions that changed, with graphical indicia corresponding to the quantitative degree of consistency or change in consistency, respectively.

In some embodiments, a duration of cardiac activity data is processed to calculate and display the progression of cardiac activation through time, over the surface of a digital model of cardiac anatomy. Lines tracing the path of propagation of the active wave front can be drawn or otherwise shown on the display along the surface, parallel to the direction of propagation. The trace lines can be continuous and/or semi-continuous.

In some embodiments, at an initial activation time, To, a number of "seed points" can be calculated along the active wave front, with the number and location of seed points determined to uniformly distribute them along the active wave front. At each additional time sample in the cardiac activity data, the seed points are advanced with the advancement of the active wave front across the surface, and a line connecting the new location of the seed points to the previous location of the seed points can be drawn. After all time samples during the duration of cardiac activity has been included, a set of continuous and/or semi-continuous lines can be traced across the surface, providing the user with advanced information about regions of convergence and regions of divergence, regions of reentry or repetition, as well as regions of block that inhibit advancement of the active wave front.

Within a main cardiac information display window or area 1305, a digital model of cardiac anatomy 1302 is shown with cardiac activation data superimposed or overlaid thereon. In this embodiment, the cardiac activation data represents conduction velocity which can be displayed with a magnitude and direction using "streamlines", e.g., characteristics resembling "grain" or "flow" in a single frame of video, superimposed on the digital model of cardiac anatomy 1302. Dynamic motion can be applied to visually accentuate the magnitude in the direction of motion.

As with previously described embodiments, an EKG 1310 is presented in an auxiliary cardiac information display window or area 1315 below the main cardiac information display window 1305 displaying the cardiac anatomy 1302. Area 1315 can display one or more signals, such as a signal selected from the group consisting of: a biopotential signal such as an EGM; surface charge density signal; surface dipole density signal; surface voltage signal; an EKG; and combinations of these.

A set of user-interactive controls 1320 can include a window width device 1322 configured to enable a user to set a time duration for display, e.g. a time duration for which the calculated data displayed represents, in the main cardiac information display window 1305, here shown set at 30 ms. The window width is indicated in the semitransparent sliding window 1312 superimposed over the EKG 1310. A user-selectable and/or settable display scale 1324 is also provided, which can be used for setting $t_{SCALE}$. Here, $t_{SCALE}$ is set at 3 ms. Accordingly, the horizontal axis of the EKG includes 3 ms increments. Play, rewind, and fast forward controls 1326 are also shown.

The semitransparent sliding window 1312 is in sync with the cardiac activation data shown overlaid on the cardiac anatomy 1302. Therefore, the semitransparent sliding window 1312 and the cardiac activation data overlaid on the cardiac anatomy 1302 can dynamically change with respect to a common time scale. The displays are linked in time and change together, since their outputs are based on the same time-dependent data.

As described above, In FIG. 13, a display mode is depicted that graphically represents a propagation pattern direction and velocity using streamlines that give the appearance of a grain superimposed on the heart. In this embodiment, as an example, data aggregated over a period of time ranging from, e.g., 100 ms to 10 min, such as is, 4 s, 10 s, or 30 s), can be processed to determine consistency of conduction characteristics, such as the characteristics described above that can be derived from the raw surface data (e.g., charge density data or voltage data).

Both depolarization and repolarization patterns can be displayed as described hereabove. Overlapping the two, while displaying each with a differentiating characteristic, such as color, texture and/or pattern, can be graphically provided. For example, in FIG. 13 the cardiac surface is depicted with a first color, here the color blue (B). Cardiac activation data, such as conduction and its characteristics are represented with other colors, here the colors yellow and green, depicted as various shades of grey (G), superimposed on the surface of the heart, here shown in blue (B).

The grainy streamlines in FIG. 13 depict not only cardiac activation, but its direction. In FIG. 13, only a few conductive "paths" (events) are shown in Area 1 during the period indicated by the sliding window 1312. In contrast, many conductive paths are shown in Area 2 during the same period. This increased density of conductive paths in Area 2 correlates to greater cardiac activity in Area 2 as compared to Area 1. The increased density of conductive paths in Area 2 may alternatively correlate to greater consistency or repetition of cardiac activity, or another characteristic of the pattern of activation or conduction, as described above.

Figure 14:
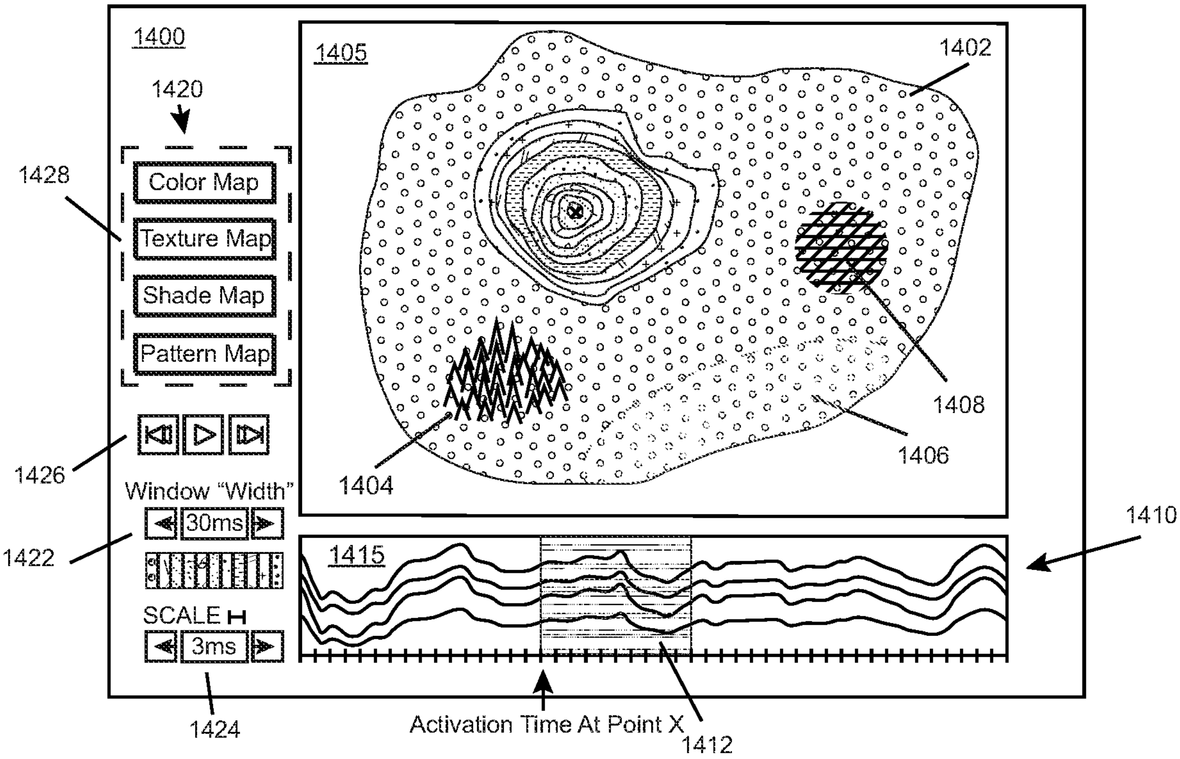
FIG. 14 is a view of an embodiment of cardiac activation data rendered on a digital model of cardiac anatomy, in accordance with aspects of the inventive concept.

FIG. 14 shows an embodiment of a display screen 1400 comprising multiple regions within which cardiac activation data can be rendered, and user-interactive controls can be provided, in accordance with aspects of the inventive concept. The cardiac activation data is time series data that can be dynamically displayed as a function of time. Displays described with respect to FIG. 14 can be generated using the same processors, modules, and databases described above for rendering other displays.

Display 1400 can comprise a display similar to those described above with respect to FIGS. 10 and 12A-O. Similar to FIGS. 10 and 12A-O, a plurality of different displays can be provided to represent the propagation of cardiac activity over the surface of the cardiac chamber. However, since that concept has been described, it will not be repeated here.

Within a main cardiac information display window or area 1405, a digital model of cardiac anatomy 1402 is shown with cardiac activation data superimposed or overlaid thereon. In this embodiment, the cardiac activation data is rendered with an activation status indicated by a series of colors (represented as patterns 1-11) superimposed on the reconstructed heart 1402.

Display 1400 can simultaneously display two or more unique graphical indicia representing different physiological parameters of one or more portions of the heart as represented by the digital cardiac model 1402 being displayed. The various graphical indicia used to represent these physiologic parameters can be selected from the group consisting of: a color range; a pattern; a symbol; a shape; an opacity level; stippling; hue; geometry of a 2D or 3D object; and combinations of these. The graphical indicia used to represent the physiological characteristics can be static or dynamic.

The simultaneous display of multiple physiologic characteristics, e.g., as differentiated via the various graphical indicia, can be overlaid on one or more digital models of cardiac anatomy in one or more combinations. Various physiologic parameters, such as minimum re-activation time, conduction velocity, number of occurrences the vorticity threshold was crossed during a time period and/or other physiologic parameters can each be represented by a unique graphical indicia. In some embodiments, e.g., a continuing example of the streamlines overlaid on the digital model described above in reference to FIG. 13, the minimum re-activation time at each node can be shown in different colors, such as colors selected within a gradient color space. A cross-hatch pattern with discrete levels of hatch density or line thickness can be overlaid on the digital model, such as to identify regions falling into different categories of conduction velocity. Surface spheroids can be overlaid, centered on nodes with vorticity greater than a threshold, with the diameter of the spheroids displayed proportional to the number of occurrences the vorticity threshold was crossed during the duration of cardiac activity.

As with previously described embodiments, an EGM 1410 can be presented in an auxiliary cardiac information display window or area 1415 below the main cardiac information display window 1405 displaying the reconstructed heart 1402.

A set of user-interactive controls 1420 can include a window width device 1422 configured to enable a user to set a time duration for display, e.g. a time duration for which the calculated data displayed represents, in the main cardiac information display window 1405, here set at 30 ms. The window width is indicated in the semitransparent sliding window 1412 superimposed over the EGM 1410. A user-selectable or settable display scale 1424 is also provided, which can be used for setting $t_{SCALE}$. Here, $t_{SCALE}$ is set at 3 ms. Accordingly, the horizontal axis of the EGM includes 3 ms increments. Play, rewind, and fast forward controls 1426 are also shown.

The semitransparent sliding window 1412 is in sync with the cardiac activation data shown overlaid on the reconstructed heart 1402. Therefore, the semitransparent sliding window 1412 and the cardiac activation data overlaid on the reconstructed heart 1402 can dynamically change with respect to a common time scale. The displays are linked in time and change together, since their outputs are based on the same time-dependent date.

A set of display mode or layer devices 1428 can be provided to enable a user to control at least portions of the display in main window 1405, in particular to control at least portions of the display of cardiac activation data on reconstructed heart 1402. In this embodiment, separate "buttons" (or other user-interactive controls) are provided as devices 1428 for selecting "Color Map," Texture Map," "Shade Map," and "Pattern Map" graphical options. In some embodiments, one or more of such devices can be provided. Not all such devices need be provided in every embodiment. In some embodiments, none of the devices 1428 need be provided.

In FIG. 14, the reconstructed cardiac chamber 1402 is shown with cardiac activation data represented as varying colors, i.e., responsive to the Color Map button. For illustration purposes, portions of the reconstructed cardiac chamber 1402 are shown with a texture map 1404 responsive to the Texture Map button, a shade map 1406 responsive to the Shade Map button, and a pattern map 1408 responsive to the Pattern Map button. That is, in some embodiments, such buttons (or similar controls) can be used to selectively turn on their respective maps.

For example, textures, e.g., roughness, which can be uniform, and grain, which can be directional, can be overlaid on the surface anatomy to visualize conduction or substrate characteristics, as in FIG. 14. A z-height 'roughness' of the texture can be increased or decreased proportionally with the degree of the variable. For example, directional block could be shown with a texture comprising a direction, similar to a wood grain or spikes, see texture map 1404.

Continuing the above example, shading and/or the use of a distinct fixed color palette or gradient (distinct from any other color palette used), such as grayscale, can be used to identify varying degrees of block, such as fixed block, directional block, and/or functional block.

A multi-directional region of activation can be shown with overlays of different unidirectional textures or lines, producing a 'hatch' pattern, see pattern 1408. A calculation of an index of fibrosis and/or other state index characterizing the surface/substrate can be displayed with a uniform texture, such as a fine pattern similar in appearance to cement or a coarser pattern similar in appearance to pebbles. An index of fibrosis or other state indices that present an obstruction or obstacle to the conduction pattern can be determined by a combination of velocity, directional uniformity, and/or other conduction pattern characteristics.

Incorporating textures, patterns, shading and the like on the surface of the cardiac chamber 1402 provides a way to show more information in coordination with other types of cardiac activity information. This configuration is an extended implementation of visual 'layers' in the map display that can be used individually or in any combination to look at multiple variables simultaneously, such as through the use of user-interactive devices 1428.

Figure 15:
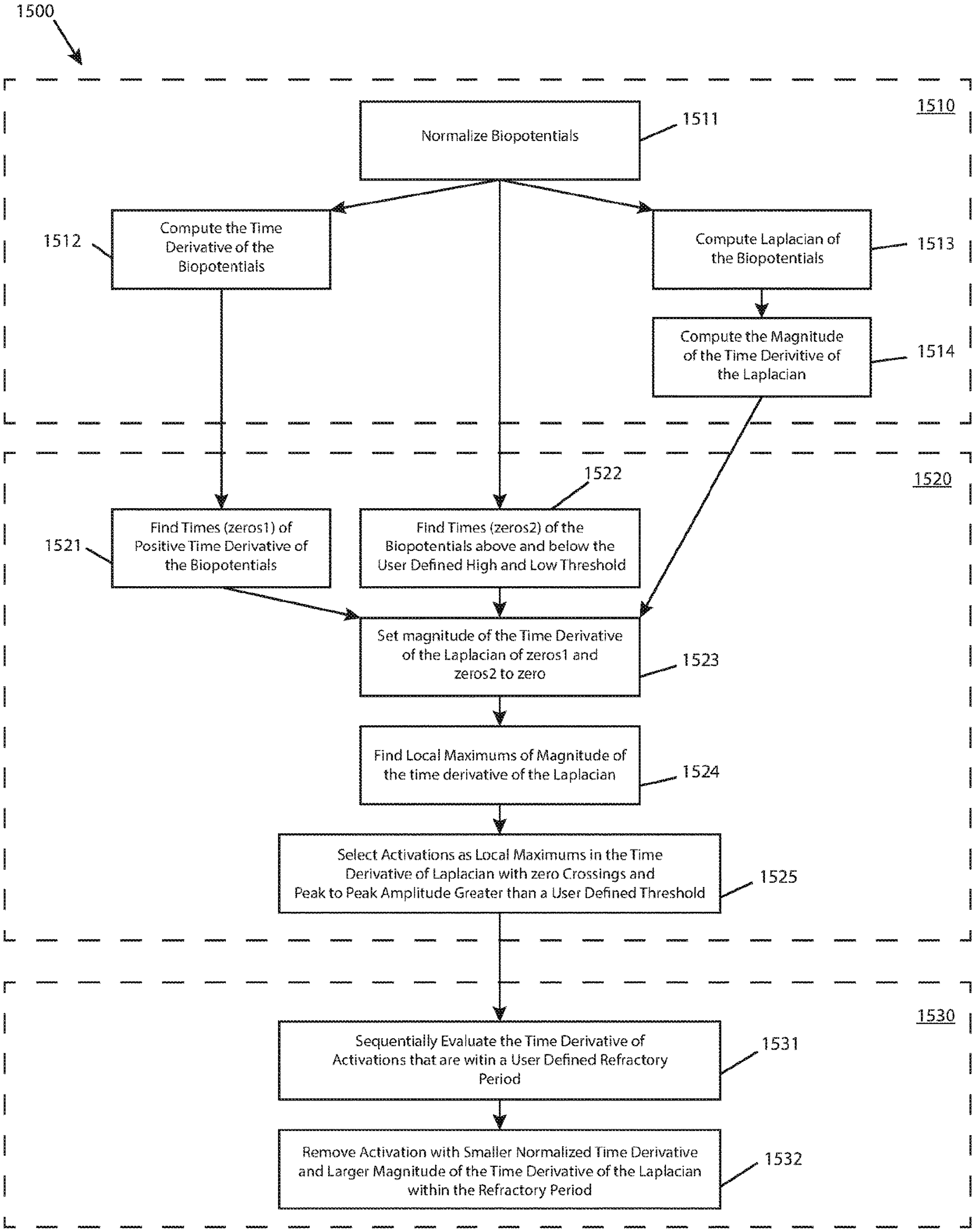
FIG. 15 is an embodiment of a method of determining cardiac information, in accordance with aspects of the inventive concept.

Referring now to FIG. 15, a flow chart for determining cardiac information is shown. FIG. 15 depicts a non-limiting example of an algorithm for determining activation at a point on the cardiac surface, e.g. a point represented by a node in a digital cardiac model of system 100. Biopotential signals at each node, e.g., as recorded by system 100 as described hereabove, can be subject to an algorithm used to determine when the node is transitioning from a resting state to a depolarized state, which is known as activation. As shown in process 1500 of FIG. 15, in stage 1510, a preprocessing stage, the biopotential signals can be normalized between the values of −1 and 1. From these normalized signals, several additional signals can be computed, including the time derivative, the Laplacian, and/or the magnitude of the time derivative of the Laplacian. As described herein, a biopotential signal can comprise a signal at a single node, at a single instance in time, and/or a set of signals at a set of nodes, during a time period. Throughout process 1500, and other processes described herein, calculated values can be stored in memory, such as a memory circuit of system 100, and used by a processor in subsequent calculations, whose output can also be stored in memory, and/or used to generate a display. In Step 1511 of stage 1510, the biopotential signals are normalized. In Step 1512, the time derivatives of the biopotentials are calculated. In step 1513, the Laplacian of the biopotentials are calculated. In step 1514, the magnitude of the time derivative of the Laplacian calculations are calculated.

The activation status of each node can then be determined through a heuristic approach involving two additional stages, stage 1520 and 1530. The first stage, stage 1520, sets all time points as a point of activation that meet characteristics of an activation as determined by the biopotential signal, the time derivative of the signal and the magnitude of the time derivative of the Laplacian. In step 1521, the times (zeros1) are calculated, corresponding to the positive time derivative of the biopotentials. In step 1522, the times (zeros2) are calculated, corresponding to biopotentials which fall above a high threshold and below a low threshold. The high and/or low thresholds can be predetermined or user definable. e.g., adjustable. In step 1523, the magnitude of the time derivative of the Laplacian of the zeros found in steps 1521 and 1522 (zeros1 and zeros2) are set to zero. In step 1524, the local maximums of magnitude of the time derivative of the Laplacian are calculated. In step 1525, activations are determined as local maximums in the time derivative of Laplacian with zero crossings and peak to peak amplitudes greater than a threshold. The threshold can be predetermined or a user definable threshold.

The second stage, stage 1530, includes refining the activation selection. In this stage, each activation is sequentially evaluated, by characteristics of the biopotential signal and its derived signals, against its temporal neighbors, until there is at most one activation within a user defined time window. In step 1531, the time derivative of the activations that are with a "refractory period" are sequentially evaluated. The refractory period can be predetermined or user definable. In step 1532, activations are removed for nodes with a smaller normalized time derivative and a larger magnitude of the time derivative of the Laplacian than previous activations within the refractory period.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

We claim:

1. A cardiac information dynamic display system, comprising:

one or more electrodes configured to discretely sample and record sets of electric potential data representing cardiac activity at a plurality of time intervals;

a cardiac information console, comprising a signal processor configured to: represent one or more cardiac chambers as a plurality of nodes; wherein the plurality of nodes comprises at least about 3,000 nodes;

calculate sets of cardiac activity data at the plurality of time intervals for each node using the recorded sets of electric potential data, wherein the calculated cardiac activity data includes at least one from: charge densities or dipole densities at surface locations of one or more cardiac chambers;

calculate a discrete set of cardiac activity data from the electric potential data for each time interval from the plurality of time intervals without aggregation of cardiac activity data or electric potential data from previous time intervals, and wherein each time interval is less than or equal to one cardiac cycle;

from the sets of cardiac activity data, calculate node data comprising an activation state for each node from the plurality of nodes at each time interval, the activation state is chosen from a plurality of different time-based activation states and the activation state choosing employs dynamic thresholding, which compares time-dependent threshold values to the calculated cardiac activity data, to determine activation states at corresponding nodes;

post-process the node data to identify one or more patterns of propagation of activation across the plurality of nodes for the plurality of time intervals, the one or more patterns of propagation including rotational activation, radial expansion from a point, or multi-directional activation through a confined zone; and determine, based on the identified one or more patterns of propagation, one or more regions of interest within the one or more cardiac chambers for therapy delivery; and a user interface module configured to dynamically display a graphical representation of the node data as a series of discrete time-based images that form a moving propagation of one or more activation wavefronts across surfaces of the one or more cardiac chambers for a given time window comprising a series of time intervals, wherein each activation wavefront is a graphical representation of nodes having the same activation state at a time interval within the time window;

wherein the user interface module is configured to display at least one of:

characteristics of the identified one or more patterns of propagation; or the one or more regions of interest.

2. The system according to claim 1, wherein the one or more electrodes comprise a three-dimensional (3D) array of electrodes that is insertable into the one or more cardiac chambers.

3. The system according to claim 2, wherein the 3D array is a basket array, a spiral array, a balloon, radially deployable arms, and/or other expandable and compactible structures.

4. The system according to claim 1, wherein the signal processor is further configured to:

define a plurality of node activation states, including the activated state;

define an activation display scale as a set of time increments measured from a reference time, wherein each time increment is associated with a different node activation state; and based on the cardiac activity data and the activation display scale, associate one of the plurality of node activation states with one or more nodes from the plurality of nodes relative to the reference time.

5. The system according to claim 4, wherein the plurality of node activation states includes the activated state and one or more recently activated states, wherein the plurality of node activation states is a predefined number of node activation states.

6. The system according to claim 5, wherein the one or more recently activated states is a plurality of recently activated states.

7. The system according to claim 5, wherein the activated state and each recently activated state is associated with a different time increment of the activation display scale.

8. The system according to claim 4, wherein the cardiac information console is configured to associate one of a plurality of graphical indicia with each activation state.

9. The system according to claim 8, wherein the plurality of graphical indicia includes one or more of different colors, different hues, different lines, different line patterns, different sizes or forms of dots or stippling, different opacities, and/or different textures.

10. The system according to claim 8, wherein the user interface module is configured to display the plurality of graphical indicia as a graphical key in conjunction with the graphical representation of the propagation of the one or more activation wavefronts.

11. The system according to claim 8, wherein the user interface module is configured to display each image in the series of images to include the plurality of graphical indicia selectively associated with one or more of the plurality of nodes, wherein the graphical indicia associated with a node is chosen as a function of an activation state of the node.

12. The system according to claim 4, wherein the user interface module is configured to display each image in the series of images to include a color from a plurality of colors selectively associated with each one or more of the plurality of nodes, wherein each color represents a different activation state, and wherein the color associated with a node is chosen as a function of an activation state of the node.

13. The system according to claim 4, wherein the user interface module is configured to color code each node as a function of an activation state associated with the node, wherein each activation state is represented by a different color, hue, and/or opacity.

14. The system according to claim 4, wherein the user interface module is configured to present at least one user input device configured to enable a user to select the activation display scale.

15. The system according to claim 1, wherein the user interface module is configured to display at least a portion of the sets of cardiac activity data in conjunction with the graphical representation of the propagation of the one or more activation wavefronts.

16. The system according to claim 15, wherein the user interface module is configured to display the at least a portion of the sets of cardiac activity data in the form of an electrocardiogram and/or electrogram.

17. The system according to claim 16, wherein the user interface module is configured to display the time window as a time window image in the form of a window superimposed over at least a portion of the electrocardiogram and/or electrogram.

18. The system according to claim 15, wherein the user interface module is configured to display the time window in conjunction with the at least a portion of the sets of cardiac activity data.

19. The system according to claim 18, wherein the user interface module is configured to display the time window as an image moving relative to and/or over the electrocardiogram and/or electrogram in synchronization with the graphical representation of the propagation of the one or more activation wavefronts.

20. The system according to claim 1, wherein the user interface module is configured to present at least one user input device configured to enable a user to select a width of the time window.

21. The system according to claim 1, wherein the user interface module is responsive to a user input to pause, rewind, and play the series of images within the time window.

22. The system according to claim 1, wherein the user interface module is responsive to a user input to adjust the display speed of the series of images within the time window.

23. The system according to claim 1, wherein the user interface module is configured to display an origin of activation on the graphical representation of surfaces of the one or more cardiac chambers.

24. The system according to claim 1, wherein the user interface module is configured to display at least a portion of the propagation of the one or more activation wavefronts in real-time.

25. The system according to claim 1, wherein:

the one or more electrodes includes a plurality of electrodes arranged on a patient's torso to be non-orthogonal to a natural axis of the body, the cardiac information console is configured to define a coordinate system comprising a plurality of axes from the plurality of electrodes, and the cardiac information console is configured to determine the cardiac activity data relative to the plurality of axes.

26. The system according to claim 25, wherein the cardiac information console is configured to transform of the coordinate system from a first orientation to a second orientation.

27. The system of claim 26, wherein the transformation of the coordinate system comprises rotating the coordinate system.

28. The system of claim 26, wherein the transformation of the coordinate system comprises scaling at least one of the axes.

29. The system of claim 1, wherein the one or more activation wavefronts is a plurality of activation wavefronts propagating across surfaces of the one or more cardiac chambers for the given time window.

* * * * *